(12) United States Patent
Hoekman et al.

(10) Patent No.: US 11,752,100 B2
(45) Date of Patent: *Sep. 12, 2023

(54) INTRANASAL DELIVERY OF OLANZAPINE BY PRECISION OLFACTORY DEVICE

(71) Applicant: Impel Pharmaceuticals Inc., Seattle, WA (US)

(72) Inventors: John D. Hoekman, Seattle, WA (US); Kelsey H. Satterly, Seattle, WA (US); Inna Dashevsky, Seattle, WA (US); Aditya R. Das, Foster City, CA (US)

(73) Assignee: Impel Pharmaceuticals Inc., Seattle, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/574,511

(22) Filed: Jan. 12, 2022

(65) Prior Publication Data

US 2022/0183965 A1 Jun. 16, 2022

Related U.S. Application Data

(63) Continuation of application No. 16/240,653, filed on Jan. 4, 2019, now Pat. No. 11,278,492.
(Continued)

(51) Int. Cl.
*A61K 9/00* (2006.01)
*A61K 31/5513* (2006.01)
(Continued)

(52) U.S. Cl.
CPC ............ *A61K 9/0043* (2013.01); *A61K 9/16* (2013.01); *A61K 9/1617* (2013.01);
(Continued)

(58) Field of Classification Search
None
See application file for complete search history.

(56) References Cited

U.S. PATENT DOCUMENTS 2,933,259 A 4/1960 Raskin
3,425,414 A 2/1969 La Roche
(Continued)

FOREIGN PATENT DOCUMENTS

BR 102013019136 A2 11/2015
CN 1726037 A 1/2006
(Continued)

OTHER PUBLICATIONS

"Symbyax (olanzapine and fluoxetine) capsules for oral use," US Prescribing Information, Revised Mar. 2018, 49 pages, [Online] [Retrieved Mar. 13, 2019], Retrieved from the internet <URL:https://www.accessdata.fda.gov/drugsatfda_docs/label/2018/021520s050lbl.pdf>.

(Continued)

*Primary Examiner* — Kyung S Chang
(74) *Attorney, Agent, or Firm* — Fenwick & West LLP

(57) ABSTRACT

Methods are provided for acute treatment of agitation, including agitation in patients with schizophrenia or bipolar disorder, comprising administering to a subject with agitation an effective dose of a dry pharmaceutical composition comprising olanzapine, wherein the dose is administered by an intranasal delivery device that provides, following intranasal administration, (a) a mean peak plasma olanzapine concentration ($C_{max}$) of at least 30 ng/mL, with (b) a mean time to $C_{max}$ ($T_{max}$) of olanzapine of less than 0.5 hours. Dry pharmaceutical compositions and devices suitable for intranasal delivery of olanzapine are provided.

33 Claims, 46 Drawing Sheets

Related U.S. Application Data

(60) Provisional application No. 62/776,414, filed on Dec. 6, 2018, provisional application No. 62/774,088, filed on Nov. 30, 2018, provisional application No. 62/614,324, filed on Jan. 5, 2018.

(51) Int. Cl.
*A61M 15/00* (2006.01)
*A61K 9/16* (2006.01)
*A61P 25/18* (2006.01)
*A61K 31/00* (2006.01)

(52) U.S. Cl.
CPC .......... *A61K 9/1623* (2013.01); *A61K 9/1652* (2013.01); *A61K 31/00* (2013.01); *A61K 31/5513* (2013.01); *A61M 15/003* (2014.02); *A61P 25/18* (2018.01)

(56) References Cited

U.S. PATENT DOCUMENTS

| | | |
|---|---|---|
| 3,888,253 A | 6/1975 | Watt et al. |
| 3,906,950 A | 9/1975 | Cocozza |
| 3,908,654 A | 9/1975 | Lhoest et al. |
| 3,971,377 A | 7/1976 | Damani |
| 4,095,596 A | 6/1978 | Grayson |
| 4,187,985 A | 2/1980 | Goth |
| 4,227,522 A | 10/1980 | Cams |
| 4,353,365 A | 10/1982 | Hallworth et al. |
| 4,412,573 A | 11/1983 | Zdeb |
| 4,620,670 A | 11/1986 | Hughes |
| 4,702,415 A | 10/1987 | Hughes |
| 4,896,832 A | 1/1990 | Howlett |
| 4,995,385 A | 2/1991 | Valentini et al. |
| 5,224,471 A | 7/1993 | Marelli et al. |
| 5,307,953 A | 5/1994 | Regan |
| 5,331,954 A | 7/1994 | Rex et al. |
| 5,349,947 A | 9/1994 | Newhouse et al. |
| 5,382,236 A | 1/1995 | Otto et al. |
| 5,398,850 A | 3/1995 | Sancoff et al. |
| 5,435,282 A | 7/1995 | Haber et al. |
| 5,505,193 A | 4/1996 | Ballini et al. |
| 5,516,006 A | 5/1996 | Meshberg |
| 5,711,488 A | 1/1998 | Lund |
| 5,715,811 A | 2/1998 | Ohki et al. |
| 5,797,390 A | 8/1998 | McSoley |
| 5,814,020 A | 9/1998 | Gross |
| 5,819,730 A | 10/1998 | Stone |
| 5,823,183 A | 10/1998 | Casper et al. |
| 5,881,719 A | 3/1999 | Gottenauer et al. |
| 5,901,703 A | 5/1999 | Ohki et al. |
| 5,906,198 A | 5/1999 | Flickinger |
| 5,910,301 A | 6/1999 | Farr et al. |
| 5,954,696 A | 9/1999 | Ryan |
| 6,062,213 A | 5/2000 | Fuisz et al. |
| 6,092,522 A | 7/2000 | Calvert et al. |
| 6,145,703 A | 11/2000 | Opperman |
| 6,158,676 A | 12/2000 | Hughes |
| 6,169,084 B1 | 1/2001 | Bunnell et al. |
| 6,180,603 B1 | 1/2001 | Frey |
| 6,186,141 B1 | 2/2001 | Pike et al. |
| 6,189,739 B1 | 2/2001 | von Schuckmann |
| 6,294,153 B1 | 9/2001 | Modi |
| 6,302,101 B1 | 10/2001 | Py |
| 6,313,093 B1 | 11/2001 | Frey |
| 6,347,789 B1 | 2/2002 | Rock |
| 6,367,471 B1 | 4/2002 | Genosar et al. |
| 6,367,473 B1 | 4/2002 | Käfer |
| 6,382,465 B1 | 5/2002 | Greiner-Perth |
| 6,410,046 B1 | 6/2002 | Lerner |
| 6,491,940 B1 | 12/2002 | Levin |
| 6,540,983 B1 | 4/2003 | Adjei et al. |
| 6,569,463 B2 | 5/2003 | Patel et al. |
| 6,585,172 B2 | 7/2003 | Arghyris |
| 6,585,957 B1 | 7/2003 | Adjei et al. |
| 6,585,958 B1 | 7/2003 | Keller et al. |
| 6,595,202 B2 | 7/2003 | Gañán-Calvo |
| 6,617,321 B2 | 9/2003 | Allen et al. |
| 6,622,721 B2 | 9/2003 | Vedrine et al. |
| 6,644,305 B2 | 11/2003 | MacRae et al. |
| 6,644,309 B2 | 11/2003 | Casper et al. |
| 6,645,528 B1 | 11/2003 | Straub et al. |
| 6,647,980 B1 | 11/2003 | Gizurarson |
| 6,681,767 B1 | 1/2004 | Patton et al. |
| 6,684,879 B1 | 2/2004 | Coffee et al. |
| 6,701,916 B2 | 3/2004 | Mezzoli |
| 6,715,485 B1 | 4/2004 | Djupesland |
| 6,716,416 B2 | 4/2004 | Rabinowitz et al. |
| 6,734,162 B2 | 5/2004 | Van Antwerp et al. |
| 6,810,872 B1 | 11/2004 | Ohki et al. |
| 6,923,988 B2 | 8/2005 | Patel et al. |
| 6,932,983 B1 | 8/2005 | Straub et al. |
| 7,033,598 B2 | 4/2006 | Lerner |
| 7,051,734 B2 | 5/2006 | Casper et al. |
| 7,052,679 B2 | 5/2006 | Rabinowitz et al. |
| 7,078,020 B2 | 7/2006 | Rabinowitz et al. |
| 7,163,013 B2 | 1/2007 | Harrison |
| 7,182,277 B2 | 2/2007 | Vedrine et al. |
| 7,200,432 B2 | 4/2007 | Lerner et al. |
| 7,214,209 B2 | 5/2007 | Mazzoni |
| 7,231,919 B2 | 6/2007 | Giroux |
| 7,258,119 B2 | 8/2007 | Mazzoni |
| 7,296,566 B2 | 11/2007 | Alchas |
| 7,303,764 B2 | 12/2007 | Allen et al. |
| 7,347,201 B2 | 3/2008 | Djupesland |
| 7,377,901 B2 | 5/2008 | Djupesland et al. |
| 7,476,689 B2 | 1/2009 | Santus et al. |
| 7,481,218 B2 | 1/2009 | Djupesland |
| 7,543,581 B2 | 6/2009 | Djupesland |
| 7,601,337 B2 | 10/2009 | Rabinowitz et al. |
| 7,655,619 B2 | 2/2010 | During et al. |
| 7,740,014 B2 | 6/2010 | Djupesland |
| 7,784,460 B2 | 8/2010 | Djupesland et al. |
| 7,799,337 B2 | 9/2010 | Levin |
| 7,832,394 B2 | 11/2010 | Schechter et al. |
| 7,841,337 B2 | 11/2010 | Djupesland |
| 7,841,338 B2 | 11/2010 | Dunne et al. |
| 7,854,227 B2 | 12/2010 | Djupesland |
| 7,866,316 B2 | 1/2011 | Giroux |
| 7,905,229 B2 | 3/2011 | Giroux et al. |
| 7,932,249 B2 | 4/2011 | Bush |
| 7,934,503 B2 | 5/2011 | Djupesland et al. |
| 7,975,690 B2 | 7/2011 | Djupesland |
| 7,994,197 B2 | 8/2011 | Cook et al. |
| 8,001,963 B2 | 8/2011 | Giroux |
| 8,047,202 B2 | 11/2011 | Djupesland |
| 8,119,639 B2 | 2/2012 | Cook et al. |
| 8,122,881 B2 | 2/2012 | Giroux |
| 8,146,589 B2 | 4/2012 | Djupesland |
| 8,171,929 B2 | 5/2012 | Djupesland et al. |
| 8,327,844 B2 | 12/2012 | Djupesland |
| 8,408,427 B2 | 4/2013 | Wong |
| 8,448,637 B2 | 5/2013 | Giroux |
| 8,511,303 B2 | 8/2013 | Djupesland |
| 8,517,026 B2 | 8/2013 | Amon |
| 8,522,778 B2 | 9/2013 | Djupesland |
| 8,530,463 B2 | 9/2013 | Cartt et al. |
| 8,550,073 B2 | 10/2013 | Djupesland |
| 8,555,877 B2 | 10/2013 | Djupesland |
| 8,555,878 B2 | 10/2013 | Djupesland |
| 8,596,278 B2 | 12/2013 | Djupesland |
| 8,609,651 B2 | 12/2013 | Jamieson et al. |
| 8,710,028 B2 | 4/2014 | Watts et al. |
| 8,733,342 B2 | 5/2014 | Giroux et al. |
| 8,757,146 B2 | 6/2014 | Hoekman et al. |
| 8,800,555 B2 | 8/2014 | Djupesland |
| 8,839,790 B2 | 9/2014 | Beck Arnon |
| 8,875,794 B2 | 11/2014 | Carlsen et al. |
| 8,899,229 B2 | 12/2014 | Djupesland et al. |
| 8,899,230 B2 | 12/2014 | Immel |
| 8,910,629 B2 | 12/2014 | Djupesland et al. |
| 8,925,544 B2 | 1/2015 | Flickinger |
| 8,946,208 B2 | 2/2015 | Castile et al. |
| 8,978,647 B2 | 3/2015 | Djupesland et al. |

(56) References Cited

U.S. PATENT DOCUMENTS

| | | | |
|---|---|---|---|
| 8,987,199 B2 | 3/2015 | Abdel Maksoud et al. | |
| 9,010,325 B2 | 4/2015 | Djupesland et al. | |
| 9,038,630 B2 | 5/2015 | Djupesland et al. | |
| 9,067,034 B2 | 6/2015 | Djupesland et al. | |
| 9,072,857 B2 | 7/2015 | Djupesland | |
| 9,101,539 B2 | 8/2015 | Nagata et al. | |
| 9,119,932 B2 | 9/2015 | Djupesland | |
| 9,138,407 B2 | 9/2015 | Caponetti et al. | |
| 9,180,264 B2 | 11/2015 | Young et al. | |
| 9,272,104 B2 | 3/2016 | Djupesland | |
| 9,446,207 B2 | 9/2016 | Jung | |
| 9,550,036 B2 | 1/2017 | Hoekman et al. | |
| 2002/0017294 A1 | 2/2002 | Py | |
| 2002/0054856 A1 | 5/2002 | Jones | |
| 2002/0092520 A1 | 7/2002 | Casper et al. | |
| 2003/0017118 A1 | 1/2003 | Rabinowitz et al. | |
| 2003/0017119 A1 | 1/2003 | Rabinowitz et al. | |
| 2003/0129250 A1 | 7/2003 | Batycky et al. | |
| 2003/0158527 A1 | 8/2003 | Mezzoli | |
| 2003/0217748 A1 | 11/2003 | Giroux | |
| 2004/0068222 A1 | 4/2004 | Brian | |
| 2004/0176357 A1 | 9/2004 | Dekemper et al. | |
| 2004/0238574 A1 | 12/2004 | Merk et al. | |
| 2005/0023376 A1 | 2/2005 | Anderson | |
| 2005/0028812 A1 | 2/2005 | Djupesland | |
| 2005/0036985 A1 | 2/2005 | Ensoli | |
| 2005/0098172 A1 | 5/2005 | Anderson | |
| 2005/0118272 A1 | 6/2005 | Besse et al. | |
| 2005/0142072 A1 | 6/2005 | Birch et al. | |
| 2005/0274378 A1 | 12/2005 | Bonney et al. | |
| 2005/0281751 A1 | 12/2005 | Levin | |
| 2006/0039869 A1 | 2/2006 | Wermeling et al. | |
| 2006/0107957 A1 | 5/2006 | Djupesland | |
| 2006/0219813 A1 | 10/2006 | Morrison | |
| 2006/0223794 A1 | 10/2006 | Bourghol Hickey et al. | |
| 2006/0240092 A1 | 10/2006 | Breitenkamp et al. | |
| 2006/0240101 A1 | 10/2006 | Chungi et al. | |
| 2007/0043021 A1 | 2/2007 | Solomon | |
| 2007/0056585 A1 | 3/2007 | Davies et al. | |
| 2007/0068514 A1 | 3/2007 | Giroux | |
| 2007/0074722 A1 | 4/2007 | Giroux et al. | |
| 2007/0119451 A1 | 5/2007 | Wang et al. | |
| 2007/0131224 A1 | 6/2007 | Giroux | |
| 2007/0172517 A1 | 7/2007 | Sasson et al. | |
| 2007/0202051 A1 | 8/2007 | Schuschnig | |
| 2008/0054099 A1 | 3/2008 | Giroux et al. | |
| 2008/0096871 A1 | 4/2008 | Bush | |
| 2008/0163874 A1 | 7/2008 | Djupesland | |
| 2008/0178871 A1 | 7/2008 | Genova et al. | |
| 2008/0305077 A1 | 12/2008 | Frey et al. | |
| 2009/0028948 A1 | 1/2009 | Payne et al. | |
| 2009/0130216 A1 | 5/2009 | Cartt et al. | |
| 2009/0320832 A1 | 12/2009 | Djupestand | |
| 2011/0039806 A1 | 2/2011 | Mendlovic et al. | |
| 2011/0053859 A1 | 3/2011 | Deadwyler et al. | |
| 2012/0195959 A1 | 8/2012 | Ishii | |
| 2014/0083424 A1 | 3/2014 | Hoekman et al. | |
| 2014/0100249 A1 | 4/2014 | Sears et al. | |
| 2014/0170220 A1 | 6/2014 | Cartt et al. | |
| 2014/0343494 A1 | 11/2014 | Hoekman et al. | |
| 2015/0057287 A1 | 2/2015 | Cook et al. | |
| 2015/0216823 A1 | 8/2015 | Chatterjee | |
| 2015/0258097 A1 | 9/2015 | Conour | |
| 2015/0258178 A1 | 9/2015 | Gong | |
| 2016/0101245 A1 | 4/2016 | Hoekman et al. | |
| 2016/0228433 A1 | 8/2016 | Haruta et al. | |
| 2016/0324773 A1 | 11/2016 | Paiement et al. | |
| 2017/0143627 A1 | 5/2017 | Misra | |
| 2017/0151258 A1 | 6/2017 | Bream et al. | |

FOREIGN PATENT DOCUMENTS

| | | | |
|---|---|---|---|
| CN | 1791430 A | 6/2006 | |
| CN | 1802158 A | 7/2006 | |
| CN | 103156860 A | 6/2013 | |
| CN | 103417492 A | 12/2013 | |
| DE | 19518580 A1 | 11/1996 | |
| DE | 102013100473 A1 | 7/2014 | |
| EP | 0139098 | 5/1985 | |
| EP | 1165044 A2 | 1/2002 | |
| EP | 1180020 | 2/2002 | |
| EP | 1423124 | 6/2004 | |
| EP | 1468689 | 10/2004 | |
| EP | 1830824 | 9/2007 | |
| EP | 1838716 | 10/2007 | |
| EP | 1937229 | 7/2008 | |
| EP | 2194965 | 6/2010 | |
| EP | 2691100 | 2/2014 | |
| EP | 2694076 | 2/2014 | |
| EP | 2949317 | 12/2015 | |
| GB | 806284 A | 12/1958 | |
| GB | 1517642 A | 7/1978 | |
| JP | H08322934 A | 12/1996 | |
| JP | 2004537546 A | 12/2004 | |
| JP | 2016520378 A | 7/2016 | |
| JP | 2017523142 A | 8/2017 | |
| WO | WO 1986/001731 A1 | 3/1986 | |
| WO | WO 1999/013930 A1 | 3/1999 | |
| WO | WO 2000/054887 A1 | 9/2000 | |
| WO | WO 2001/036033 A2 | 5/2001 | |
| WO | WO 2002/009707 A1 | 2/2002 | |
| WO | WO 2006/076124 A2 | 7/2006 | |
| WO | WO 2007/012853 A1 | 2/2007 | |
| WO | WO 2008/059385 A2 | 5/2008 | |
| WO | WO 2016/058807 A1 | 4/2016 | |
| WO | WO 2017/053346 A1 | 3/2017 | |

OTHER PUBLICATIONS

"Zyprexa (olanzapine) oral and intramuscular U.S. Prescribing information," Eli Lilly and Company, Revised Oct. 2016, 41 pages, [Online] [Retrieved Mar. 13, 2019], Retrieved from the internet <URL:https://www.accessdata.fda.gov/drugsatfda_docs/label/2018/020592s071,021086s046,021253s059lbl.pdf>.

"Zyprexa IntraMuscular (olanzapine) Injection, Powder, For Solution for Intramuscular use package insert," Eli Lilly and Company, Revised Jan. 19, 2018, 35 pages, Indianapolis.

"Zyprexa NDA 205920," US Food and Drug Administration Summary Basis of Approval, 1996, 726 pages, [Online] [Retrieved Mar. 13, 2019], Retrieved from <URL:https://www.accessdata.fda.gov/drugsatfda_docs/nda96/020592_Original_Approval_Pkg%20.pdf>.

"Zyprexa Relprew (olanzapine) for Extended Release Injectable Suspension," US Prescribing Information, Revised Mar. 2018, 32 pages, [Online] [Retrieved Mar. 13, 2019], Retrieved from <URL:https://www.accessdata.fda.gov/drugsatfda_docs/label/2018/022173s029lbl.pdf>.

Abdelbary, G.A. et al., "Brain targeting of olanzapine via intranasal delivery of core shell difunctional block copolymer mixed nanomicellar carriers. In vitro characterization, ex vivo estimation of nasal toxicity and in vivo biodistribution studies," International Journal of Pharmaceutics, 2013, vol. 452, No. 1-2, pp. 300-310.

Adasuve (loxapine) Presecribing Information, Galen US Inc., 2017, 8 pages.

Appasaheb, et al., "Review on Intranasal Drug Delilvery System", Journal of Advanced Pharmacy Education and Research, vol. 3, Issue 4, Oct. 2013, 14 pages.

Atkins, S. et al., "A pooled analysis of injection site-related adverse events in patients with schizophrenia treated with olanzapine long-acting injection," BMC Psychiatry, 2014, vol. 14, No. 1, pp. 7.

Baltzley, S. et al., "Intranasal drug delivery of olanzapine-loaded chitosan nanoparticles," AAPS PharmSciTech, 2014, vol. 15, No. 6, pp. 1598-1602.

Baron, "Orally Inhaled Dihydroergotamine; Reviving and Improving a Classic", Future Neurology, May 2011, 11 pages.

Batail, J.M., et al., "Use of very-high-dose olanzapine in treatment-resistant schizophrenia," Schizophrenia Research, 2014, vol. 159, No. 2-3, pp. 411-414.

Battaglia, J. et al., "Calming versus sedative effects of intramuscular olanzapine in agitated patients," The American Journal of Emergency Medicine, 2003, vol. 21, No. 3, pp. 192-198.

(56) References Cited

OTHER PUBLICATIONS

Bhana, N. et al., "Olanzapine: an updated review of its use in the management of schizophrenia," Drugs, 2001,vol. 61, No. 1, 53 pages.

Bigos, K.L. et al., "Genetic variation in CYP3A43 explains racial difference in olanzapine clearance," Molecular psychiatry, 2011, vol. 16, No. 6, 13 pages.

Bigos, K.L. et al., "Sex, race, and smoking impact olanzapine exposure," The Journal of Clinical Pharmacology, 2008, vol. 48, No. 2, pp. 157-165.

Bymaster, F.P. et al., "Antagonism by olanzapine of dopamine D1, serotonin 2, muscarinic, histamine H1 and α1-adrenergic receptors in vitro," Schizophrenia research, 1999, vol. 37, No. 1, pp. 107-122.

Callaghan, J.T. et al., "Olanzapine pharmacokinetic and pharmacodynamic profile," Clinical Pharmacokinetics, 1999, vol. 37, No. 3, pp. 177-193.

Constantino, et al., "Intranasal administration of acetylcholinesterase inhibitors", BMC Neuroscience, Dec. 10, 2008, 3 pages.

Driver, D.I. et al., "Childhood onset schizophrenia and early onset schizophrenia spectrum disorders," Cgukd and Adolexcent Psychiatric Clinics, 2013, vol. 22, No. 4, pp. 539-555.

Duong, S. et al., "Intramuscular Olanzapine in the Management of Behavioral and Psychological Symptoms in Hospitalized Older Adults: A retrospective Descriptive Study," Journal of Aging Research, 2015, vol. 2015, 7 pages.

European Patent Office, EP Office Action for 14727320.5, dated Nov. 9, 2016, 6 pages.

European Patent Office, EP Search Report for 09707800.0 dated Jul. 1, 2015, 12 pages.

European Patent Office, EP Search Report for 11818832.5 dated Sep. 24, 2014, 6 pages.

European Patent Office, Extended European Search Report, European Patent Application No. 19735694.2, dated Sep. 15, 2021, 11 pages.

Fasiolo, L. T. et al. "Opportunity and Challenges of Nasal Powders: Drug Formulation and Delivery." European Journal of Pharmaceutical Sciences, vol. 113, Feb. 15, 2018, pp. 2-17.

Fitzgerald, P. "Long-acting antipsychotic medication, restraint and treatment in the management of acute psychosis," Australian and New Zealand Journal of Psychiatry, 1999, vol. 33, No. 5, pp. 660-666.

Fonseca, F.N. et al., "Mucoadhesive Amphiphilic Methacrylic Copolymer-Functionalized Poly(ε-caprolactone) Nanocapsules for Nose-to-Brain Delivery of Olanzapine," Journal of Biomedical Nanotechnology, 2015, vol. 11, No. 8, pp. 1472-1481.

Galletly, C. et al., "Royal Australian and New Zealand College of Psychiatrists clinical practice guidelines for the management of schizophrenia and related disorders," Australian & New Zealand Journal of Psychiatry, 2016, vol. 50, No. 5, pp. 410-472.

Gizurarson, S., "Anatomical and histological factors affecting intranasal drug and vaccine delivery," Current Drug Delivery, 2012, vol. 9, No. 6, pp. 566-582.

Gross, E.A. et al., "Comparative morphometry of the nasal cavity in rats and mice," Journal of Anatomy, 1982, vol. 135, No. 1, pp. 83-88.

Hanson, et al., "Intranasal delivery of growth differentiation factor 5 to the central nervous system", Drug Delivery, 19(3):149-54, Feb. 2012, 7 pages.

Harkema, J.R. et al., "The nose revisited: A brief review of the comparative structure, function and toxicological pathology of the nasal epithelium," Toxicologic Pathology, 2006, vol. 34, No. 3, pp. 252-269.

Harris, A.J. et al., "Determination of surface areas, volumes, and lengths of cynomolgus monkey nasal cavities by ex vivo magnetic resonance imaging," Journal of Aerosol Medicine, 2003, vol. 16, No. 2, pp. 99-105.

Hoekman, J.D., "The Impact of Enhanced Olfactory Deposition and Retention on Direct Nose-to-Brain Drug Delivery", UMI Dissertation Publishing, Apr. 11, 2011, 181 pages.

Holloman, G.H.J. et al., "Overview of Project BETA: Best practices in Evaluation and Treatment of Agitation," Western Journal of Emergency Medicine, 2012, vol. 13, No. 1, pp. 1-2.

International Search Report for PCT/US/2009/033468 dated Dec. 2, 2009, 5 pages.

Katare, Y.K. et al., "Intranasal delivery of antipsychotic drugs," Schizophrenia Research, 2016, vol. 184, pp. 2-13.

Kishi, T. et al., "Intramuscular olanzapine for agitated patients: A systematic review and meta-analysis of Yandomized controlled trials," Journal of Psychiatric Research, 2015, vol. 68, pp. 198-209.

Kumar, "Mucoadhesive nanoemulsion-based intranasal drug delivery system of olanzapine for brain targeting," Journal of Drug Targeting, Dec. 2008, vol. 16, No. 10, pp. 806-814.

Kumar, et al., "Nasal Drug Delivery: A Potential Route for Brain Targeting" The Pharma Innovation Journal, vol. 2, No. 1, Mar. 2013. 9 pages.

Lachman, A., "New developments in diagnosis and treatment update: Schizophrenia/first episode psychosis in children and adolescents,"Journal of child and adolescent mental health, 2014, vol. 26, No. 2, pp. 109-124.

Liu, Y. et al., "Creation of a standardized geometry of the human nasal cavity," Journal of Applied Physiology, 2009, vol. 106, pp. 784-795.

McCormack, P.L. et al., "Olanzapine: a review of its use in the management of bipolar I disorder," Drugs, 2004, vol. 64, No. 23, pp. 2709-2726.

Nordstrom, K. et al., "Alternative delivery systems for agents to treat acute agitation: Progress to date," Drugs, 2013, vol. 73, No. 16, pp. 1783-1792.

Nordstrom, K. et al., "Medical evaluation and triage of the agitated patient: consensus statement of the American Association for Emergency Psychiatry Project BETA Medical Evaluation workgroup," Western Journal of Emergency Medicine, 2012, vol. 13, No. 1, pp. 3-10.

Ozsoy, et al., "Nasal Delivery of High Molecular Weight Drugs", Molecules Journal, Sep. 23, 2009, 26 pages.

Parvathi, "Intranasal Drug Delivery to Brain: An Overview," published in the International Journal of Research in Pharmacy and Chemistry 2012, 2(3), 7 pages.

Patel, R.B. et al., "Evaluation of brain targeting efficiency of intranasal microemulsion containing olanzapine: pharmacodynamic and pharmacokinetic consideration," Drug Delivery, 2016, vol. 23, No. 1,10 pages.

Patel, R.B. et al., "Formulation and Evaluation of Microemulsions-Based Drug Delivery System for Intranasal Administation of Olanzapine," International Journal of Biomedical and Pharmaceutical Sciences, 2013, vol. 7, No. 1, pp. 20-27.

PCT International Search Report and Written Opinion, PCT Application No. PCT/US2019/012426, dated Mar. 5, 2019, fourteen pages.

PCT Search Report and Written Opinion dated Mar. 27, 2012 for PCT application No. PCT/US2011/048435, 14 pages.

Raga, J.M. et al., "1st International Experts' Meeting on Agitation: Conclusions Regarding the Current and Ideal management Paradigm of Agitation," Fronteirs in Psychiatry, Feb. 27, 2018, vol. 9, No. 54, pp. 1-9.

Real, J.D. et al., "A naturalistic comparison study of effectiveness of intramuscular olanzapine and intramuscular haloperidol in acute agitated patients with schizophrenia," Neuropsychiatry, 2016, vol. 6, No. 5, pp. 229-235.

Renner, et al., "Intranasal delivery of growth differentiation factor 5 to the central nervous system," Drug Delivery, Feb. 2012, 7 pages.

Ruby, J.J. et al., "Formulation and evaluation of olanzapine loaded chitosan nanoparticles for nose to brain targeting an in vitro and ex vivo toxicity study," Journal of Applied Pharmaceutical Science, Sep. 2016, vol. 6, No. 9, pp. 034-040.

Ryles, F. et al., "A systematic review of the frequency and severity of manic symptoms reported in studies that compare phenomenology across children, adolescents and adults with bipolar disorders," International journal of bipolar disorders, 2017, vol. 5, No. 4, pp. 1-11.

(56) References Cited

OTHER PUBLICATIONS

Salama, H.A. et al., "Brain delivery of olanzapine by intranasal administration of transfersomal vesicles," Journal of Liposome Research, 2012, vol. 22, No. 4, pp. 336-345.
Seju, U. et al., "Development and evaluation of olanzapine-loaded PLGA nanoparticles for nose-to-brain delivery: In vitro and in vivo studies," Acta biomaterialia, 2011, vol. 7, No. 12, pp. 4169-4176.
Serra, G. et al., "Pediatric Mania. The Controversy between Euphoria and Irritability," Current neuropharmacology, 2017, vol. 15, No. 3, pp. 386-393.
Stevens, et al., "Systemic and Direct Nose-to-Brain Transport Pharmacokinetic Model for Remoxipride after Intravenous and Intranasal Administration", in "Drug Metabolism and Disposition", The American Society for Pharmacology and Experimental Therapeutics, 2011, vol. 39, No. 12, 8 pages.
Swanson, J.W. et al., "A national study of violent behavior in persons with schizophrenia," Archives of general psychiatry, May 2006, vol. 63, No. 5, pp. 490-499.
Talegaonkar, et al., "Intranasal delivery: an approach to bypass the blook brain barrier", Indian J Pharmacol, Jun. 2004, vol. 36, Issue 3, 8 pages.
Tardiff, K., "The current state of psychiatry in the treatment of violent patients," Archives of general psychiatry, 1992, vol. 49, No. 6, pp. 493-499.
The Department of Health. "5.2 Speed of Drug Effect: Methods of Drug Administration in Order of Fastest to Slowest CNS Response." Australian Government Department of Health, 2004, 2 pages.
Wagstaff, A.J. et al., "Intramuscular olanzapine: a review of its use in the management of acute agitation," CNS Drugs, 2005, vol. 19, No. 2, pp. 147-164.
Westin et al., "Direct Nose to Brain Transfer of Morphine After Nasal Administration to Rats", Pharmaceutical Research, vol. 23, No. 3, Mar. 2006, 8 pgs.
Westin, "Olfactory Tranfser of Analgesic Drugs After Nasal Administration", Digital Comprehensive Summaries of Uppsala Dissertations from the Faculty of Pharmacy 55, May 11, 2007, 66 pages.
Wink, L.K. et al., "Multiple antipsychotic medication use in autism spectrum disorder," Journal of Child and Adolexcent Psychopharmacology, 2017, vol. 27, No. 1, pp. 91-94.
Wright, P. et al., "Antipsychotic drugs: atypical advantages and typical disadvantages," Irish Journal of Psychological Medicine, 2003, vol. 20, No. 1, pp. 24-27.
Wright, P., et al., "Double-blind, placebo-controlled comparison of intramuscular olanzapine and intramuscular haloperidol in the treatment of acute agitation in schizophrenia," American Journal of Psychiatry, 2001, vol. 158, No. 7, pp. 1149-1151.
Yamada, et al., "Nose-to-brain delivery of TS-002, prostaglandin D2 analogue", Journal of Drug Targeting, Jan. 2007, 9 pages.
Yildiz, A., et al., "Pharmacological management of agitation in emergency settings," Emergency medicine journal, 2003, Emergency Medicine Journal, 2003, vol. 20, No. 4, pp. 339-346.
Yimam, et al., "Effects of lipid association on lomustine (CCNU) administered intracerebrally to syngeneic 36B-10 rat brain tumors", Cancer Letters 244(2), Dec. 2006, 9 pages.
Ying, "The nose may help the brain: intranasal drug delivery for treating neurological diseases" Future Medicine, 3(1), Jan. 2008, 4 pages.
Zhang, et al., "The brain targeting efficiency following nasally applied MPEG-PLA nanoparticles in rats", Journal of Drug Targeting, Jun. 2006, 11 pages.
Iwasaki, S. et al. "A Case of Successful Treatment with Olanzapine Intramuscular Injection for Acute Severe Excitement and Refusal of Medication in Manic Phase of Bipolar Disorder." The Hokuriku Journal of Neuropsychiatry, vol. 28, No. 1-2, 2014, pp. 2-8, (with English abstract).
Salama, H. A. et al. "Phospholipid Based Colloidal Poloxamer-Nanocubic Vesicles for Brain Targeting via the Nasal Route." Colloids and Surfaces B: Biointerfaces, vol. 100, Dec. 1, 2012, pp. 146-154.

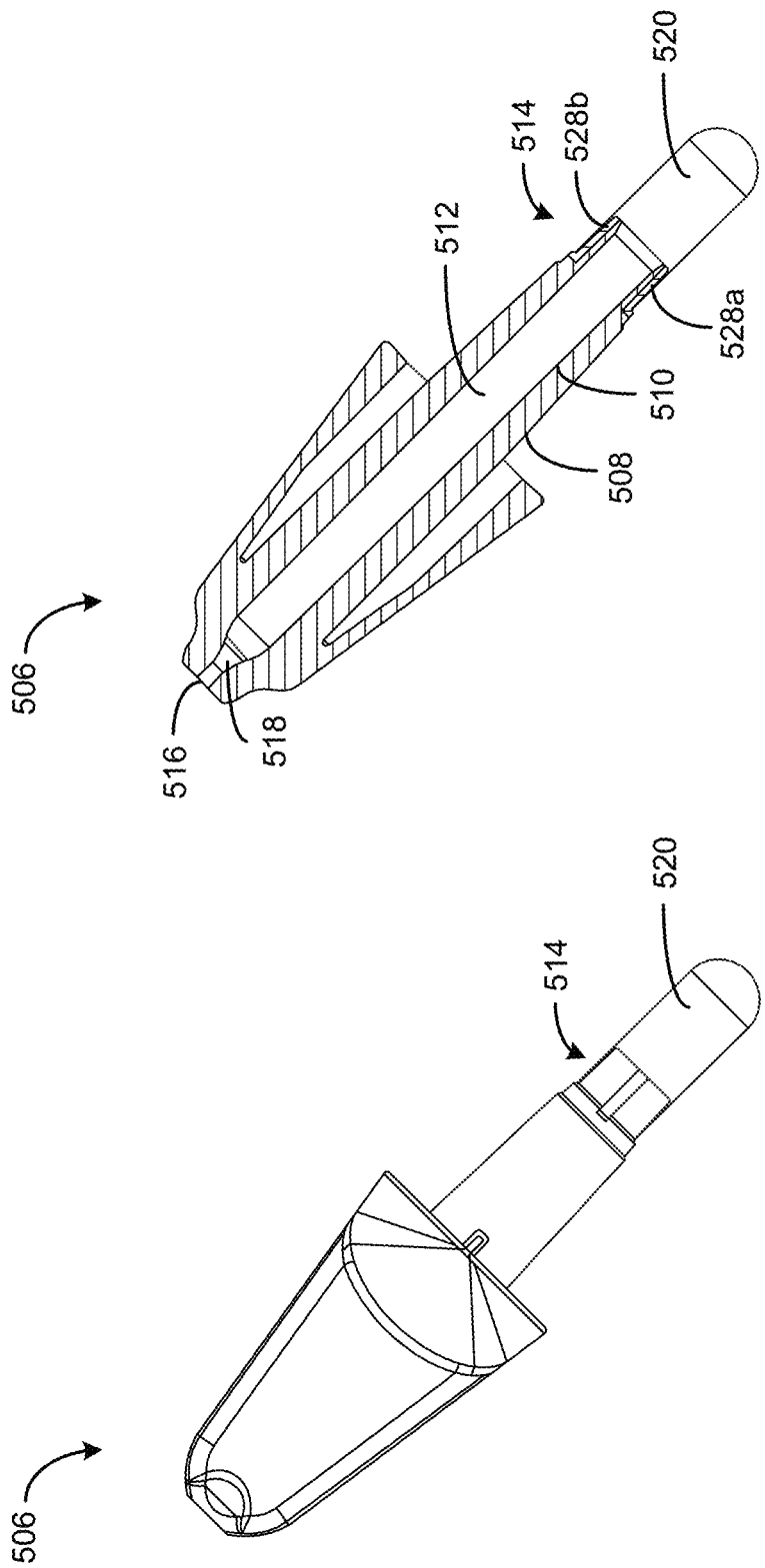

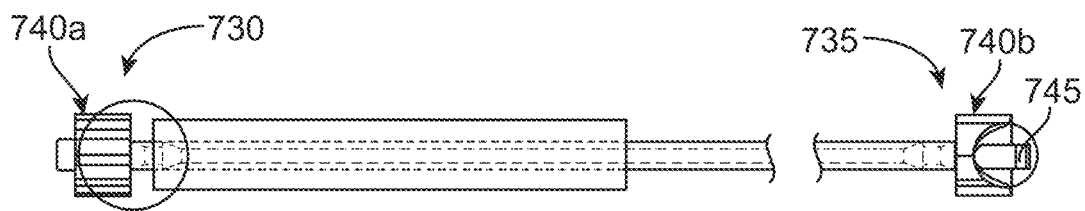
FIG. 7C
FIG. 7D
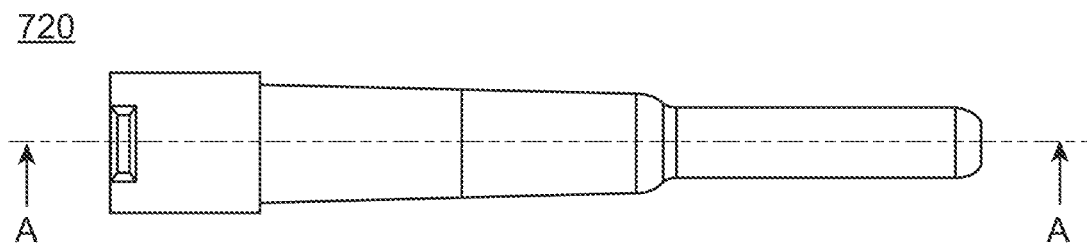
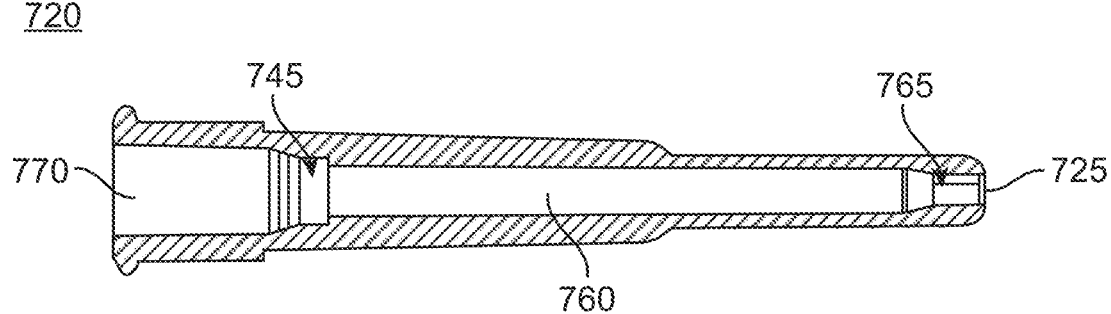
SECTION A-A
FIG. 7E

INTRANASAL DELIVERY OF OLANZAPINE BY PRECISION OLFACTORY DEVICE

1. CROSS-REFERENCE TO RELATED APPLICATIONS

This application is a continuation of co-pending U.S. patent application Ser. No. 16/240,653, filed Jan. 4, 2019, which claims priority to U.S. Provisional Application Nos. 62/776,414, filed Dec. 6, 2018; 62/774,088, filed Nov. 30, 2018; and 62/614,324, filed Jan. 5, 2018, each of which is incorporated herein by reference in its entirety.

2. BACKGROUND

Of 130 million US emergency room visits per year, 1.7 million are estimated to involve agitated patients, including patients whose agitation is a manifestation of schizophrenia or bipolar disorder.

The current standard of care in treating acute and escalating agitation events in schizophrenia or bipolar I mania is to administer 5 mg, 7.5 mg or 10 mg of olanzapine, an atypical antipsychotic, by intramuscular injection (IM). While olanzapine IM is characterized by a rapid onset of action (mean maximum plasma concentration within 15 to 45 minutes), this route of administration is characterized by a number of injection-related acute side-effects, including injection site pain, over sedation, extrapyramidal symptoms, and akathisia (Atkins et al., *BMC Psychiatry* 14, 7 (2014); Battaglia et al., *Am. J. Emerg. Med.* 21:192-198 (2003); Kishi et al., *J. Psychiatr. Res.* 68:198-209 (2015)). Moreover, the invasive intramuscular injection process can lead to emotional trauma for the patient, whether cooperative or uncooperative, and can lead to physical assault on hospital staff attempting to administer the injection. Furthermore, IM injections are contraindicated in patients who are cooperative (Nordstrom et al., *West. J. Emerg. Med.* 13(1):3-10 (2012)).

Oral administration of olanzapine, either as a standard tablet or orally disintegrating tablet, is approved for acute treatment of manic or mixed episodes associated with bipolar 1 disorder and lacks many of the disadvantages of intramuscular injection in this patient population; however, there is significant lag before effective blood levels are achieved and agitation reduced.

Pulmonary delivery of the typical antipsychotic loxapine by oral inhalation was approved in 2017 for acute treatment of agitation associated with schizophrenia or bipolar 1 disorder in adults. However, the product label includes a black box warning that administration can cause bronchospasm that has the potential to lead to respiratory distress and respiratory arrest (ADASUVE FDA product label, August 2017), and the product is available only under a risk evaluation and mitigation strategy (REMS).

An effective non-invasive treatment of acute agitation could shift treatment earlier in the agitation episode from the emergency room into the "community", with significant benefits, including reduction of emergency department visits and health economic burden. There is, accordingly, a need for an acute treatment of agitation, including agitation related to schizophrenia and bipolar disease, with rapid onset of action and that does not require parenteral injection.

3. SUMMARY

We have developed dry powder formulations of olanzapine suitable for intranasal delivery by a handheld, manually actuated, propellant-driven, metered-dose intranasal administration device. Following single dose PK studies in cynomolgus monkeys and in rodents, we conducted a phase I trial in healthy human subjects. In this phase I study, intranasal delivery of the olanzapine formulation resulted in similar or slightly higher plasma exposure (AUC) and maximum $C_{max}$ as compared to the IM administered olanzapine at the same dose. Furthermore, the median $T_{max}$ after intranasal delivery of the formulation—ranging from 0.16-0.17 hrs across three tested doses—was significantly shorter than the median $T_{max}$ measured for both intramuscular and oral administration, demonstrating fast and effective absorption of olanzapine across nasal epithelium.

Pharmacodynamic effects were measured using three standardized behavioral tests. The behavioral tests showed that intranasal administration of olanzapine induces calming effects similar to or better than IM or oral administration of olanzapine. Consistent with the pharmacokinetic data, behavioral effects of olanzapine were observed significantly earlier in the subject groups treated with intranasal olanzapine (INP105) compared to the subject group treated with oral olanzapine (Zyprexa Zydis). These results show that intranasal delivery of olanzapine can be an effective method for acute treatment of agitation.

Accordingly, in a first aspect, methods are presented for acute treatment of agitation. The methods comprise intranasally administering an effective dose of a dry pharmaceutical composition comprising olanzapine to a subject exhibiting agitation.

In typical embodiments, the dry pharmaceutical composition is a powder. In some embodiments, the powder comprises the powder comprises olanzapine in a crystalline or amorphous form. In some embodiments, the olanzapine is an amorphous solid obtained by spray-drying. In some embodiments, the dry pharmaceutical composition comprises olanzapine in a partially crystalline and partially amorphous form.

In some embodiments, the median diameter of the olanzapine particle size distribution (D50) in the powder as measured by laser diffraction particle size analyzer, such as the Malvern Panalytical Mastersizer 3000, is between 1 μm and 100 μm, between 1 μm and 50 μm, or between 1 μm and 15 μm. In some embodiments, the median diameter of the olanzapine particle size distribution (D50) is between 7.5 μm and 15 μm.

In some embodiments, the dose is administered by an intranasal delivery device. In some embodiments, the intranasal delivery device is a handheld, manually actuated, metered-dose intranasal administration device. In some embodiments, the intranasal delivery device is a handheld, manually actuated, propellant-driven, metered-dose intranasal administration device.

In some embodiments, the dry pharmaceutical composition is, prior to device actuation, encapsulated within a capsule positioned within the device. In some embodiments, the dry pharmaceutical composition is, prior to device actuation, stored within a dose container that is removably coupled to the device.

In some embodiments, the intranasal delivery device is capable of delivering the dry pharmaceutical composition to the upper nasal cavity.

In some embodiments, the dry pharmaceutical composition comprises no more than 70 wt %, or no more than 60 wt % olanzapine. In some embodiments, the dry pharmaceutical composition comprises 10-60% wt % olanzapine, 20-60% wt % olanzapine, 25-55 wt % olanzapine, 30-50 wt % olanzapine, or 40-50 wt % olanzapine.

In some embodiments, the dry pharmaceutical composition further comprises a stabilizer, wherein the stabilizer is selected from the group consisting of: hydroxypropylmethylcellulose (HPMC), polyvinyl caprolactam-polyvinyl acetate-polyethylene glycol graft co-polymer (Soluplus), vinyl pyrrolidine-vinyl acetate copolymer (Kollidon VA64), polyvinyl pyrrolidine K30 (Kollidon K30), polyvinyl pyrrolidone K90 (Kollidon K90), hydroxypropylcellulose (HPC), hydroxypropyl betacyclodextrin (HPBCD), mannitol, and lactose monohydrate. In some embodiments, the stabilizer is hydroxypropylmethylcellulose (HPMC).

In some embodiments, the dry pharmaceutical composition further comprises a permeation enhancer, wherein the permeation enhancer is selected from the group consisting of: n-tridecyl-β-D-maltoside, n-dodecyl-β-D-maltoside, 1,2-distearoyl-sn-glycero-3-phosphocholine (DSPC), 1,2-dipalmitoyl-sn-glycero-3-phosphocholine (DPPC), 1,2-dioleoyl-sn-glycero-3-phosphocholine (DOPC), propylene glycol, disodium EDTA, PEG400 monostearate, polysorbate 80, and macrogol (15) hydroxystearate. In some embodiments, the permeation enhancer is 1,2-distearoyl-sn-glycero-3-phosphocholine (DSPC).

In some embodiments, the dry pharmaceutical composition further comprises an antioxidant, wherein the antioxidant is selected from the group consisting of: alpha tocopherol, ascorbic acid, ascorbyl palmitate, bronopol butylated hydroxyanisole (BHA), butylated hydroxytoluene (BHT), citric acid monohydrate, sodium ascorbate, ethylene diainetetraacetic acid, fumaric acid, malic acid, methionine, propionic acid, sodium metabisulfite, sodium sulfite, sodiumthiosulfate, thymol, and vitamin E polyethylene glycol succinate.

In some embodiments, the dry pharmaceutical composition comprises less than 3 wt %, less than 2 wt %, less than 1.5 wt %, less than 1 wt %, or less than 0.5 wt % water.

In some embodiments, the dry pharmaceutical composition consists essentially of: 50 wt % olanzapine; 42 wt % HPMC; and 8 wt % DSPC.

In some embodiments, the effective dose is a dose of olanzapine effective to reduce agitation within 60 minutes. In some embodiments, the effective dose of dry pharmaceutical composition comprises 1-30 mg of olanzapine; 2-20 mg of olanzapine; 5-15 mg of olanzapine; 5 mg of olanzapine; 10 mg of olanzapine; or 15 mg of olanzapine.

In some embodiments, the effective dose is administered as a single undivided dose. In some embodiments, the effective dose is administered as a plurality of equally divided sub-doses.

In some embodiments, the subject has schizophrenia. In some embodiments, the subject has bipolar disorder, optionally bipolar I disorder. In some embodiments, the subject has autism, dementia, PTSD, intoxication, or drug-induced psychotic state.

In some embodiments, the intranasal administration provides: (a) a mean peak plasma olanzapine concentration ($C_{max}$) of at least 20 ng/mL, with (b) a mean time to $C_{max}$ ($T_{max}$) of olanzapine of less than 1.5 hours.

In some embodiments, the intranasal administration provides: a mean time to $C_{max}$ ($T_{max}$) of olanzapine of less than 1.0 hour; a mean time to $C_{max}$ ($T_{max}$) of olanzapine of less than 0.75 hour; a mean time to $C_{max}$ ($T_{max}$) of olanzapine of less than 0.50 hour or a mean time to $C_{max}$ ($T_{max}$) of olanzapine of less than 0.25 hour.

In some embodiments, the intranasal administration provides: a mean peak plasma olanzapine concentration ($C_{max}$) of at least 40 ng/mL; a mean peak plasma olanzapine concentration ($C_{max}$) of at least 50 ng/mL; a mean peak plasma olanzapine concentration ($C_{max}$) of at least 60 ng/mL; a mean peak plasma olanzapine concentration ($C_{max}$) of at least 70 ng/mL; or a mean peak plasma olanzapine concentration ($C_{max}$) of at least 80 ng/mL.

In another aspect, the present invention provides a dry pharmaceutical composition suitable for intranasal administration, comprising: olanzapine, and at least one excipient.

In some embodiments, the composition is a powder. In some embodiments, the composition comprises olanzapine in a crystalline or amorphous form. In some embodiments, the composition comprises olanzapine in amorphous form. In some embodiments, the amorphous olanzapine is obtained by spray-drying. In some embodiments, the composition comprises olanzapine in a partially crystalline and partially amorphous form.

In some embodiments, the median diameter of the olanzapine particle size distribution (D50) in the powder is between 1 μm and 100 μm, between 1 μm and 50 μm, or between 1 μm and 15 μm. In some embodiments, the median diameter of the olanzapine particle size distribution (D50) is between 7.5 μm and 15 μm.

In some embodiments, the dry pharmaceutical composition comprises no more than 70 wt % olanzapine; or no more than 60 wt % olanzapine. In some embodiments, the dry pharmaceutical composition comprises 10-60% wt % olanzapine, 20-60 wt % olanzapine; 25-55 wt % olanzapine; 30-50 wt % olanzapine; 30-40 wt % olanzapine; or 40-50 wt % olanzapine.

In some embodiments, the dry pharmaceutical composition further comprises a stabilizer, wherein the stabilizer is selected from the group consisting of: hydroxypropylmethylcellulose (HPMC), polyvinyl caprolactam-polyvinyl acetate-polyethylene glycol graft co-polymer (Soluplus), vinyl pyrrolinone-vinyl acetate copolymer (Kollidon VA64), polyvinyl pyrrolinone K30 (Kollidon K30), polyvinyl pyrrolidine K90 (Kollidon K90), hydroxypropylcellulose (HPC), hydroxypropyl betacyclodextrin (HPBCD), mannitol, and lactose monohydrate. In some embodiments, the stabilizer is hydroxypropylmethylcellulose (HPMC).

In some embodiments, the dry pharmaceutical composition further comprises a permeation enhancer, wherein the permeation enhancer is selected from the group consisting of n-tridecyl-B-D-maltoside, n-dodecyl-β-D-maltoside, 1,2-distearoyl-sn-glycero-3-phosphocholine (DSPC), 1,2-dipalmitoyl-sn-glycero-3-phosphocholine (DPPC), 1,2-dioleoyl-sn-glycero-3-phosphocholine (DOPC), propylene glycol, disodium EDTA, PEG400 monostearate, polysorbate 80, and macrogol (15) hydroxystearate. In some embodiments, the permeation enhancer is 1,2-distearoyl-sn-glycero-3-phosphocholine (DSPC).

In some embodiments, the dry pharmaceutical composition further comprises an antioxidant, wherein the antioxidant is selected from the group consisting of alpha tocopherol, ascorbic acid, ascorbyl palmitate, bronopol butylated hydroxyanisole (BHA), butylated hydroxytoluene (BHT), citric acid monohydrate, sodium ascorbate, ethylene diainetetraacetic acid, fumaric acid, malic acid, methionine, propionic acid, sodium metabisulfite, sodium sulfite, sodium thiosulfate, thymol, and vitamin E polyethylene glycol succinate.

In some embodiments, the dry pharmaceutical composition comprises less than 3 wt %, less than 2 wt %, less than 1.5 wt %, less than 1 wt %, or less than 0.5 wt % water.

In some embodiments, the dry pharmaceutical composition consists essentially of: 50 wt % olanzapine; 42 wt % HPMC; and 8 wt % DSPC.

In yet another aspect, the present invention provides a unit dose form containing a dry pharmaceutical composition provided herein.

In some embodiments, the unit dosage form contains 1-30 mg of olanzapine; 2-20 mg of olanzapine; 5-15 mg of olanzapine; 5 mg of olanzapine; 10 mg of olanzapine; or 15 mg of olanzapine.

In some embodiments, the unit dosage form is a capsule that encapsulates the dry pharmaceutical composition. In some embodiments, the unit dosage form is a dose container that stores the dry pharmaceutical composition, wherein the dose container is configured to removably couple to an intranasal delivery device.

Other features and advantages of the present disclosure will become apparent from the following detailed description, including the drawings. It should be understood, however, that the detailed description and the specific examples are provided for illustration only, because various changes and modifications within the spirit and scope of the invention will become apparent to those skilled in the art from the detailed description.

4. BRIEF DESCRIPTION OF THE DRAWINGS

FIG. 5F is a perspective view of the tip with the capsule attached, in accordance with one or more embodiments FIG. 5G is a cross-sectional view of the tip with the capsule attached, in accordance with one or more embodiments.

FIG. 5O is a perspective view of the tip, in accordance with one or more embodiments.

FIG. 7C illustrates a side view of an extension tube of the intranasal device of FIG. 7A, in accordance with one or more embodiments.

FIG. 7D illustrates a zoomed-in view of two embodiments of a connecting interface at an end of the extension tube of FIG. 7C, in accordance with one or more embodiments.

FIG. 7E illustrates a side view and a cross-sectional view of a tip of the intranasal device of FIG. 7A, in accordance with one or more embodiments.

Figure 8A:
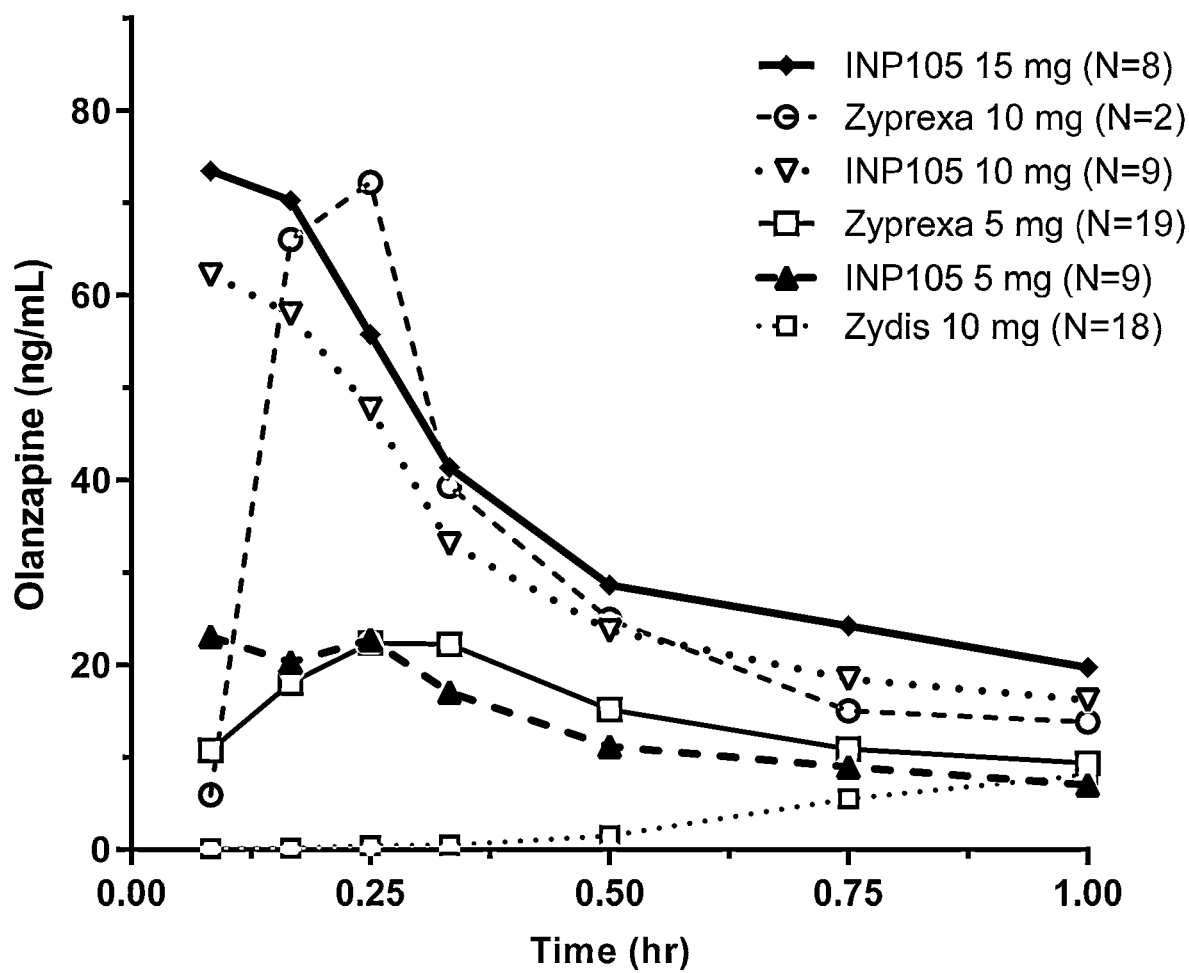
Figure 8B:
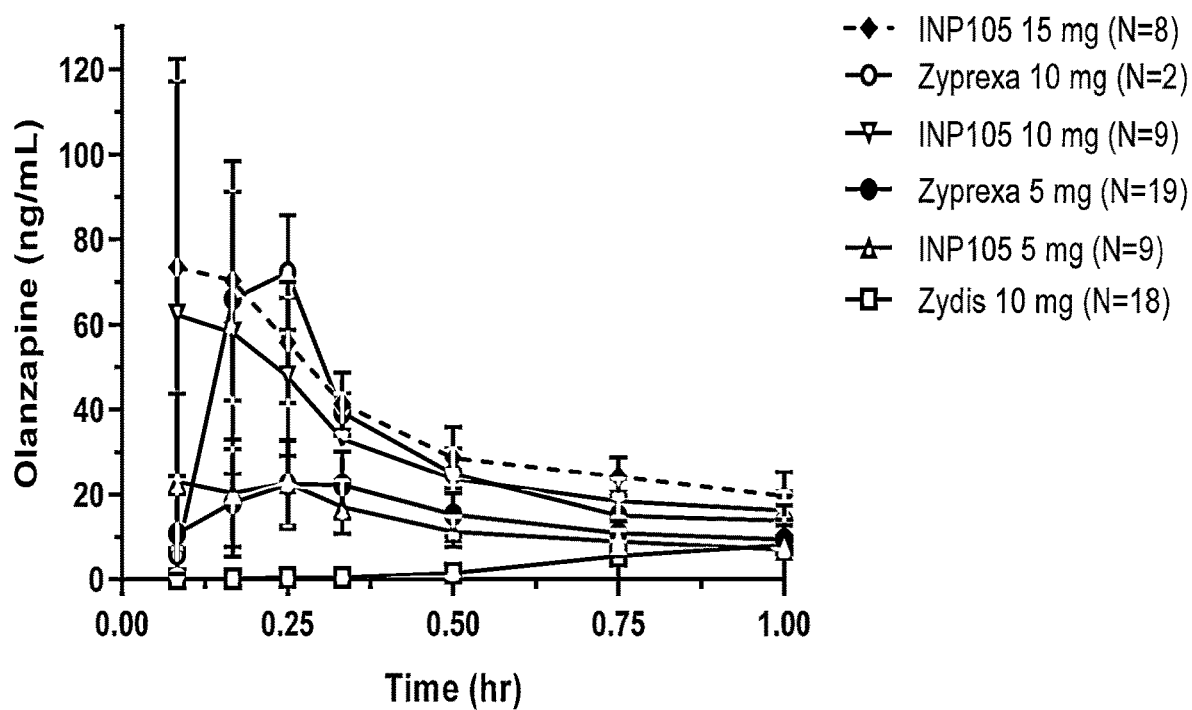
Figure 8C:
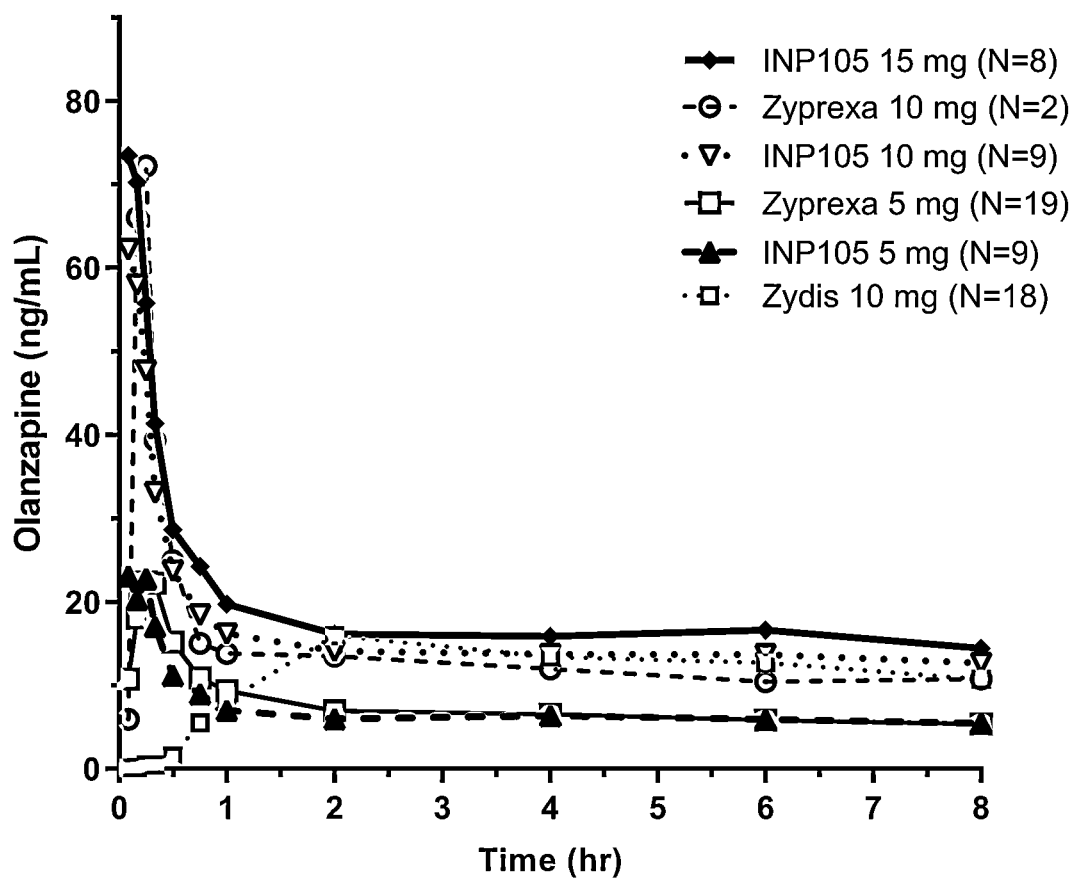

FIGS. 8A-8C show mean Plasma Concentration-Time Curves measured in human subjects following intranasal administration of 5 mg, 10 mg, or 15 mg of olanzapine (INP105); intramuscular administration of 5 mg or 10 mg of olanzapine (Zyprexa IM); or oral administration of 10 mg of olanzapine (Zyprexa Zydis). The data were obtained from the phase 1 clinical trial study described in Example 3, with FIG. 8A plotting the results without error bars, for clarity, FIG. 8B including error bars for shorter PK time points (0-1 hr), and FIG. 8C plotting the results without error bars for longer PK time points (0-8 hrs).

Figure 9:
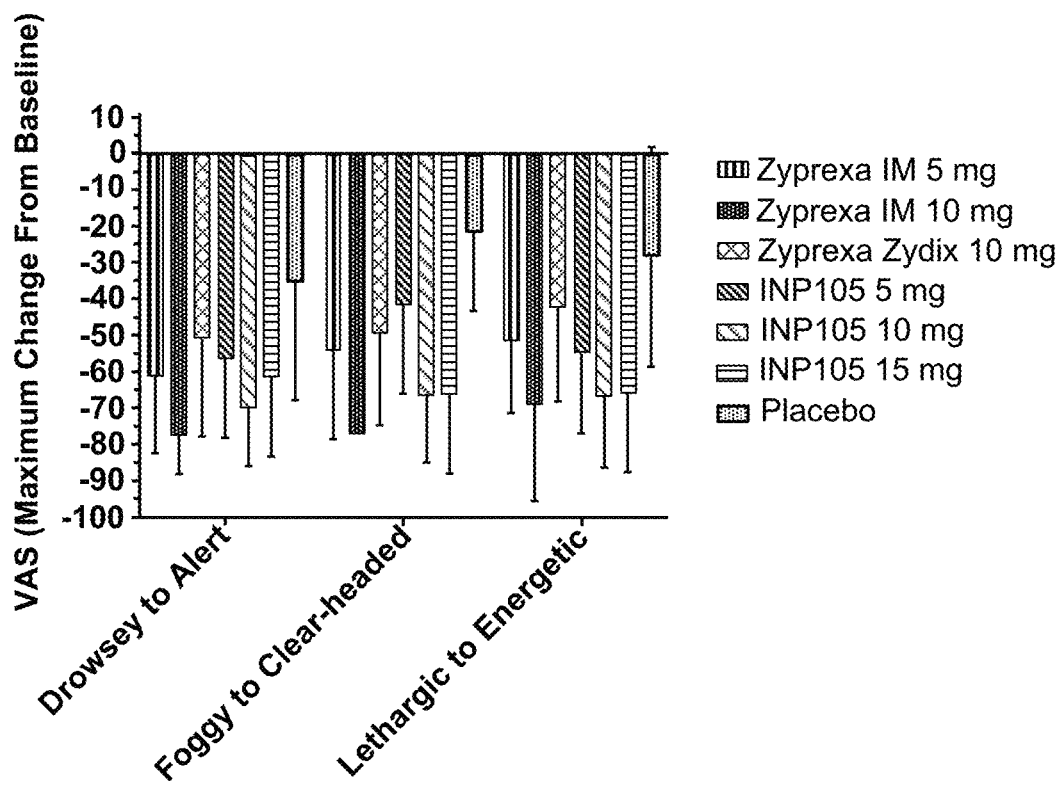

FIG. 9 shows maximum VAS score changes from baseline for three categories: Alert/Drowsy, Foggy/Clear-headed, and Energetic/Lethargic, measured in human subjects following intranasal administration of 5 mg, 10 mg, or 15 mg of olanzapine (INP105); intramuscular administration of 5 mg or 10 mg of olanzapine (Zyprexa IM); or oral administration of 10 mg of olanzapine (Zyprexa Zydis). The data were obtained from the study described in Example 3 and plotted with error bars.

Figure 10:
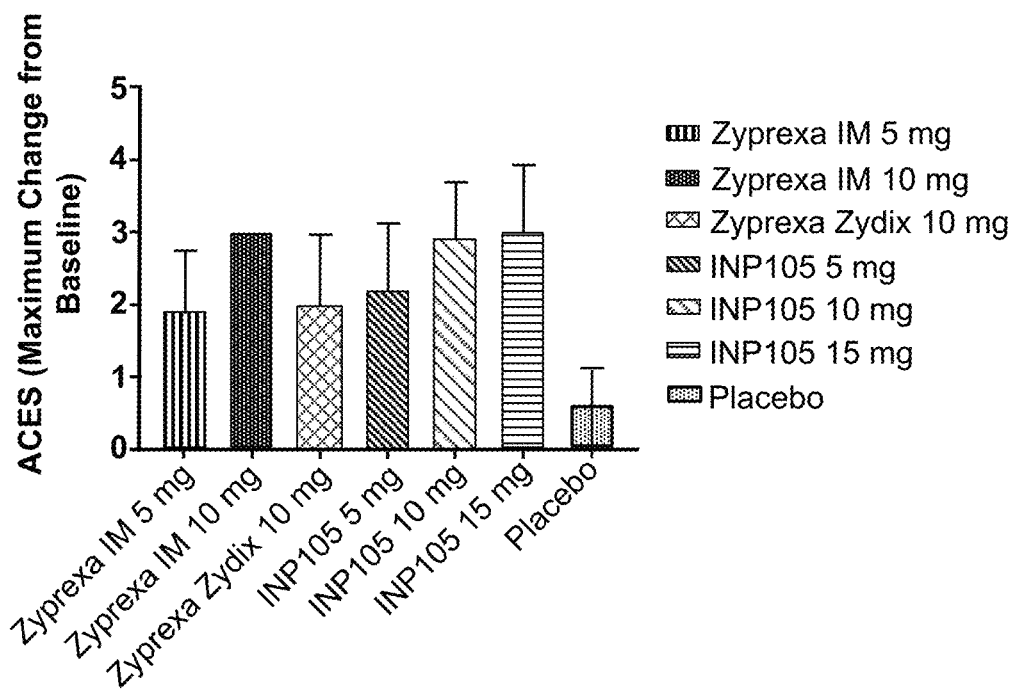

FIG. 10 shows maximum ACES score changes from baselines measured in human subjects following intranasal administration of 5 mg, 10 mg, or 15 mg of olanzapine (INP105); intramuscular administration of 5 mg or 10 mg of olanzapine (Zyprexa IM); or oral administration of 10 mg of olanzapine (Zyprexa Zydis). The data were obtained from the study described in Example 3 and plotted with error bars.

Figure 11A:
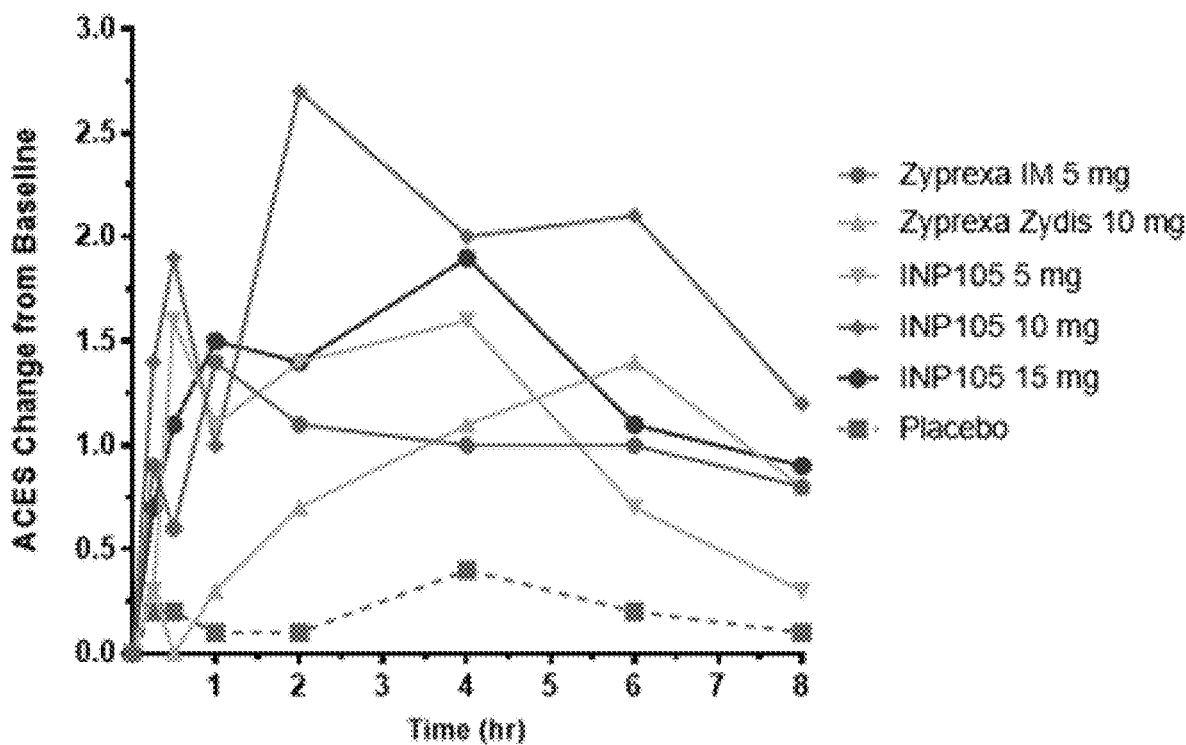
Figure 11B:
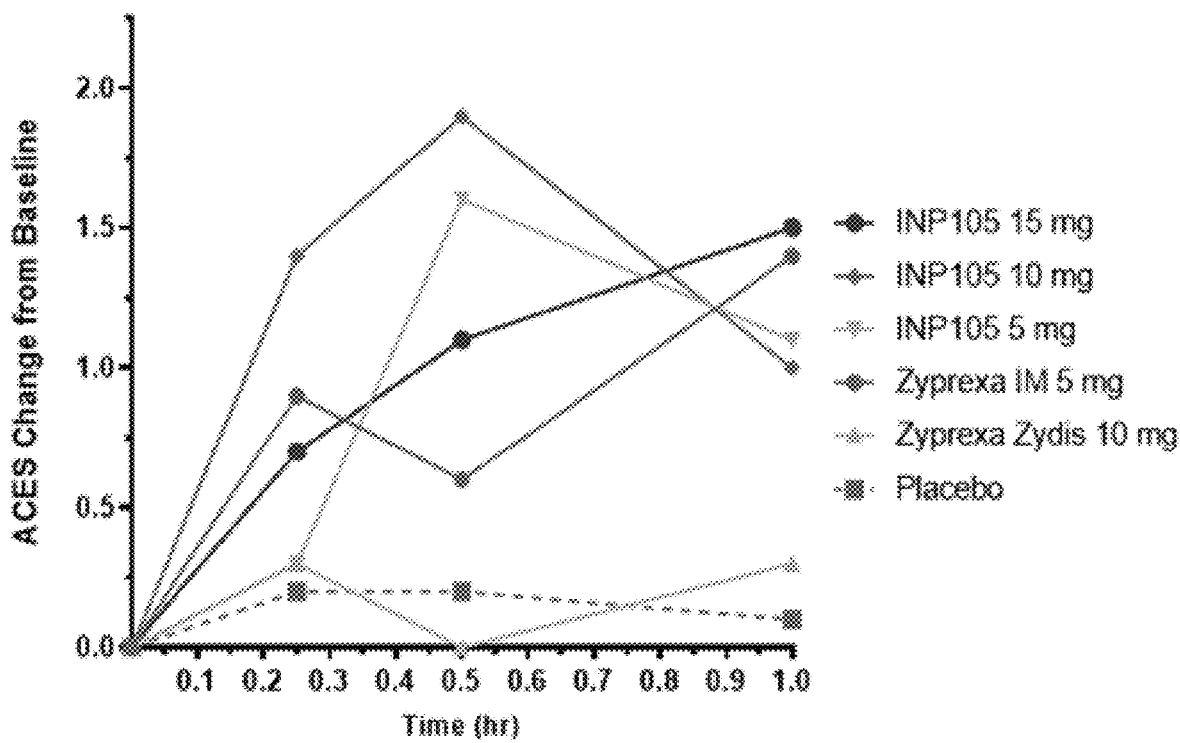

FIGS. 11A-11B show mean ACES Score-Time Curves measured in human subjects following intranasal administration of 5 mg, 10 mg, or 15 mg of olanzapine (INP105); intramuscular administration of 5 mg or 10 mg of olanzapine (Zyprexa IM); or oral administration of 10 mg of olanzapine (Zyprexa Zydis). The data were obtained from the study described in Example 3, with FIG. 11A plotting the results for longer PK time points (0-8 hrs), and FIG. 11B plotting the results for shorter PK time points (0-1 hr).

Figure 12:
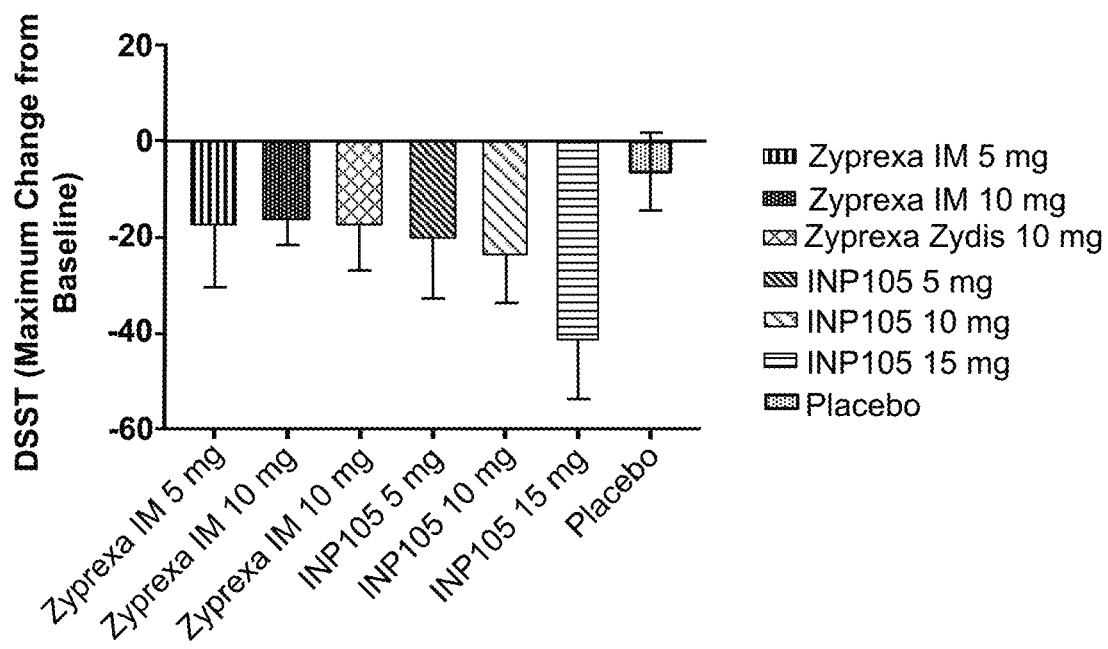

FIG. 12 shows maximum DSST score changes from baselines measured in human subjects following intranasal administration of 5 mg, 10 mg, or 15 mg of olanzapine (INP105); intramuscular administration of 5 mg or 10 mg of olanzapine (Zyprexa IM); or oral administration of 10 mg of olanzapine (Zyprexa Zydis). The data were obtained from the study described in Example 3 and plotted with error bars.

Figure 13A:
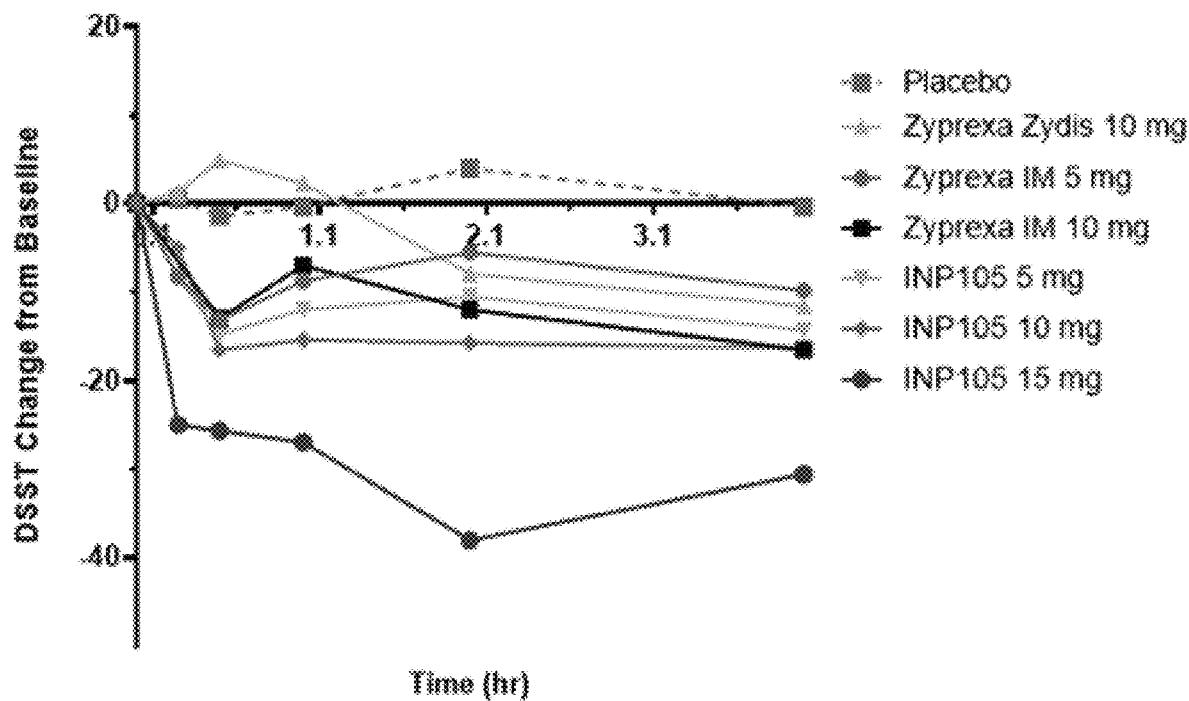
Figure 13B:
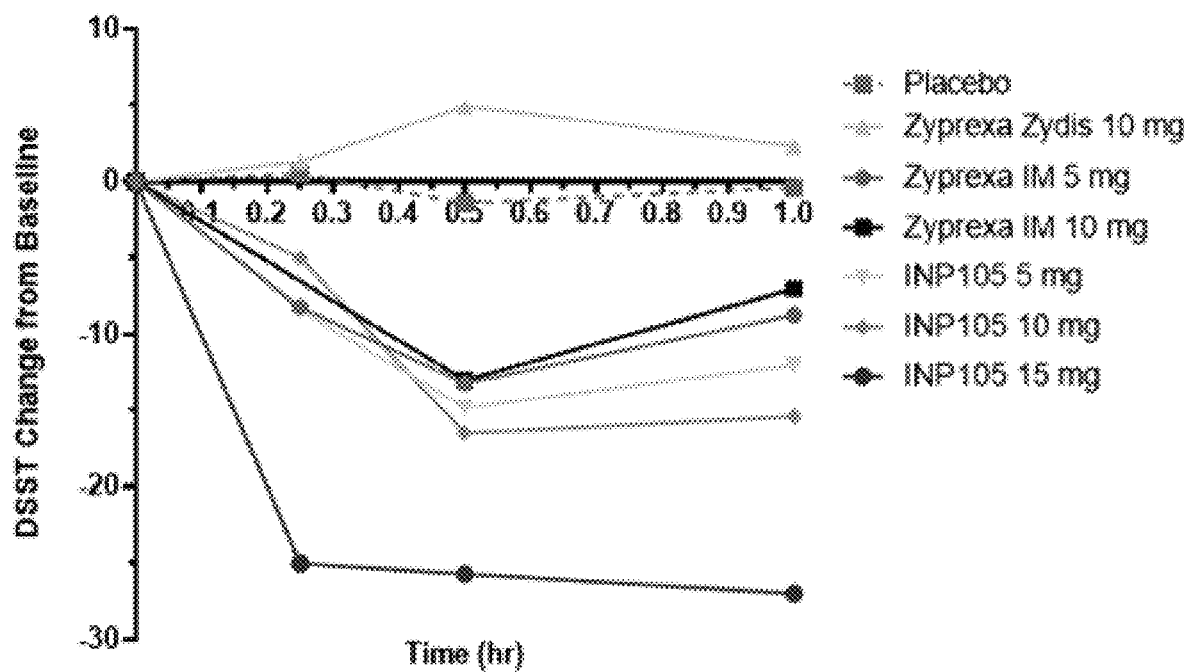

FIGS. 13A-13B show mean DSST Score-Time Curves measured in human subjects following intranasal administration of 5 mg, 10 mg, or 15 mg of olanzapine (INP105); intramuscular administration of 5 mg or 10 mg of olanzapine (Zyprexa IM); or oral administration of 10 mg of olanzapine (Zyprexa Zydis). The data were obtained from the study described in Example 3, with FIG. 13A plotting the results for longer PK time points (0-4 hrs), and FIG. 13B plotting the results for shorter PK time points (0-1 hr).

Figure 14A:
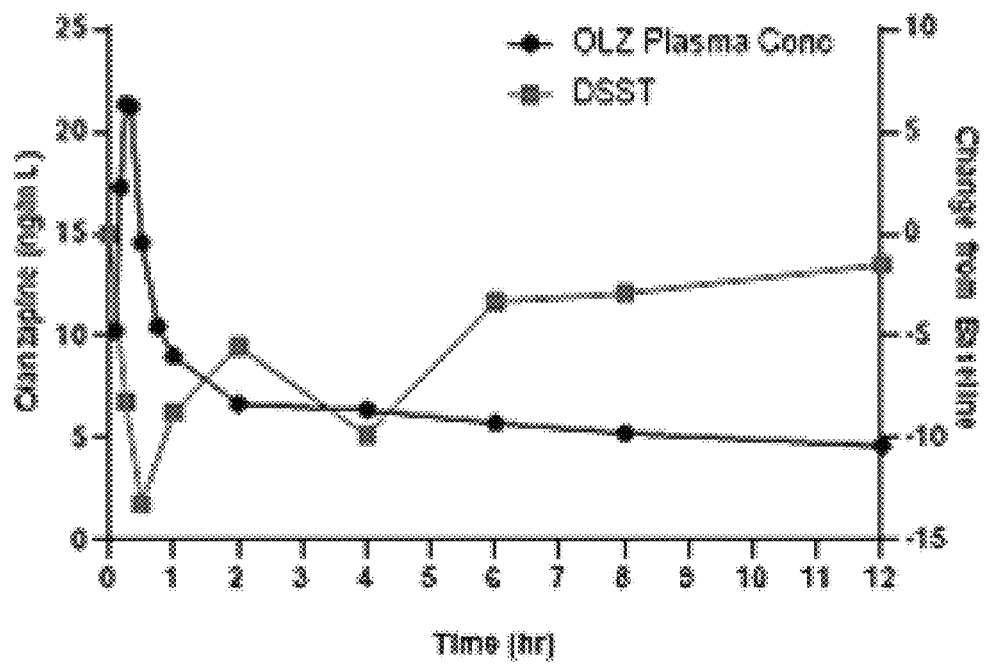
Figure 14B:
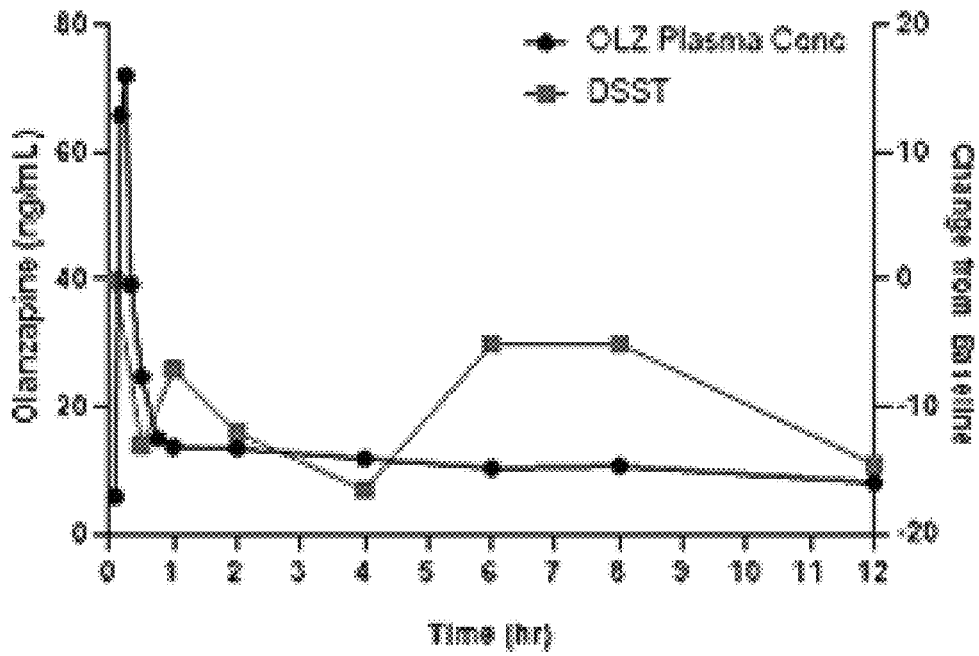
Figure 14C:
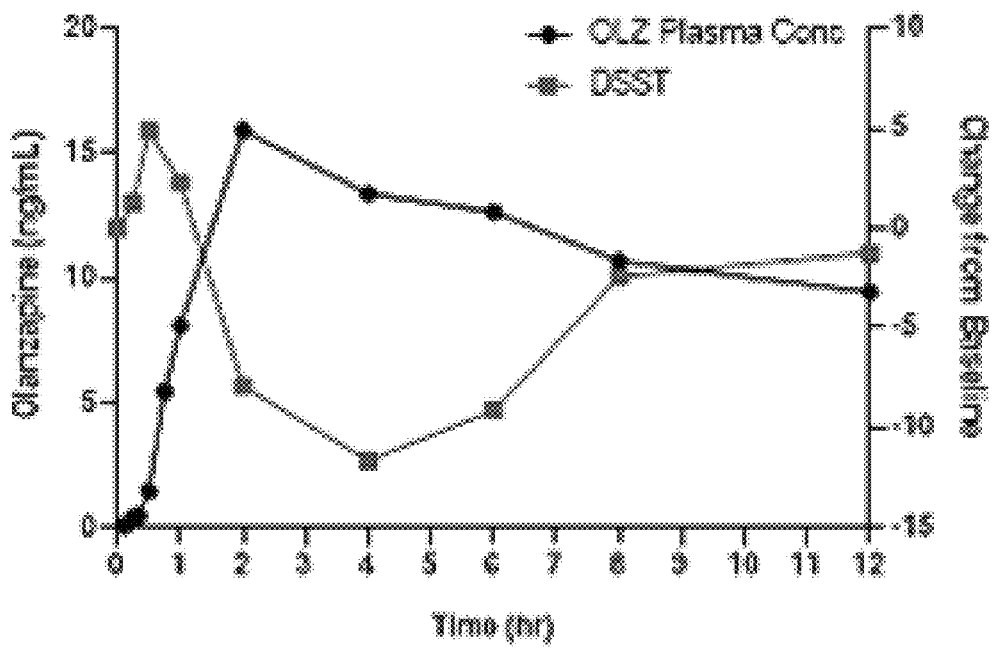
Figure 14D:
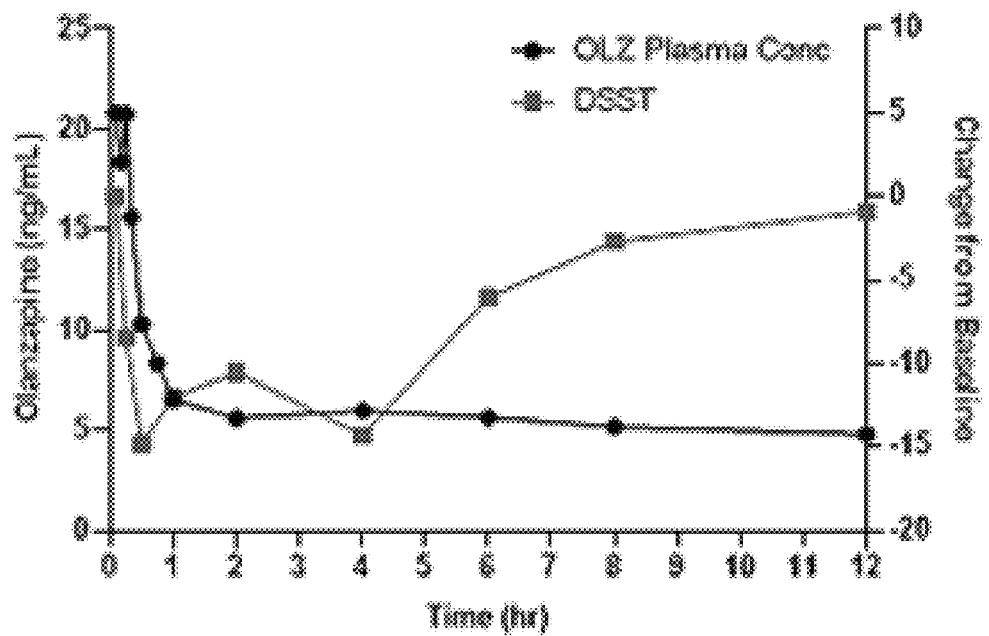
Figure 14E:
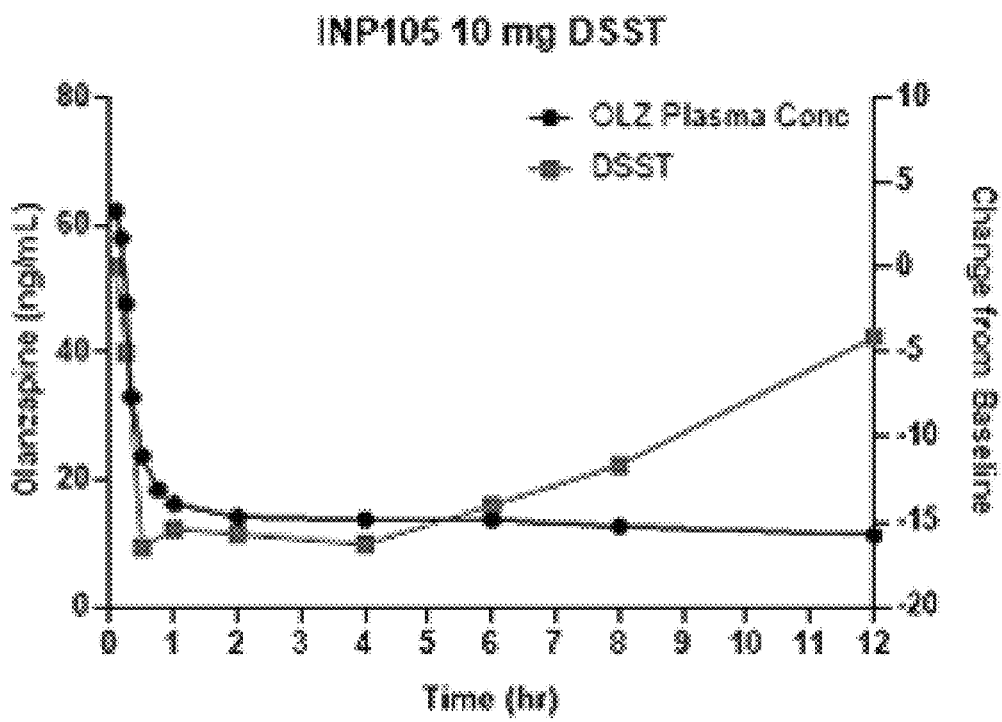
Figure 14F:
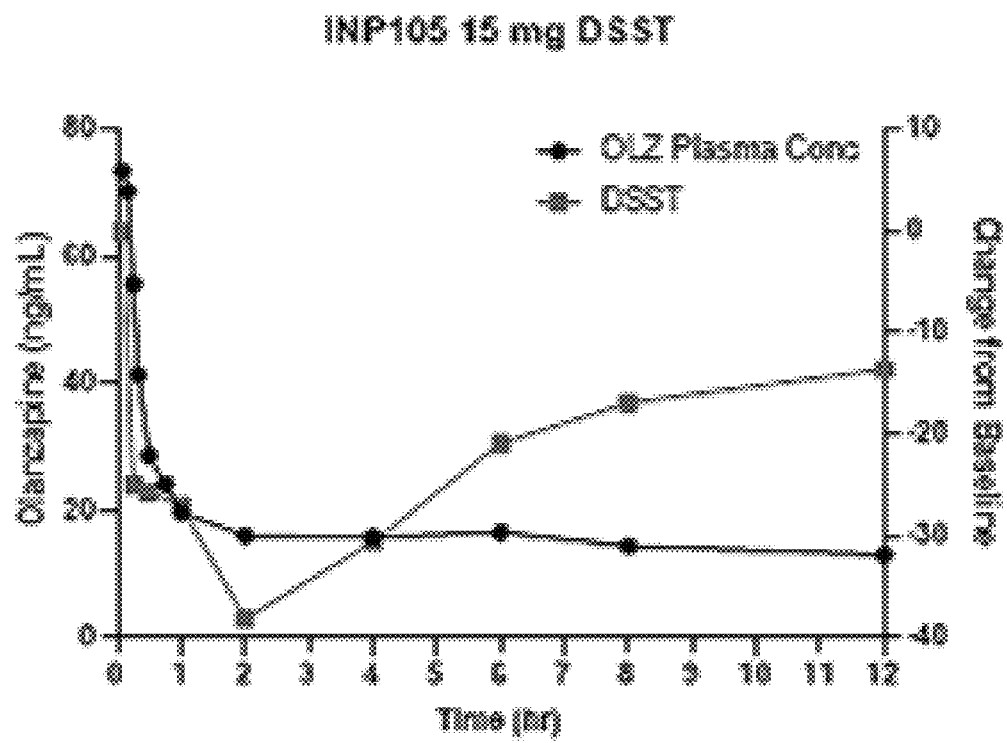

FIGS. 14A-14F show mean DSST Score-Time Curves together with mean Plasma Concentration-Time Curves measured in human subjects following intramuscular administration of 5 mg olanzapine (FIG. 14A), intramuscular administration of 10 mg olanzapine (FIG. 14B), oral administration of 10 mg olanzapine (FIG. 14C), intranasal administration of 5 mg olanzapine (FIG. 14D), intranasal administration of 10 mg olanzapine (FIG. 14E), or intranasal administration of 15 mg olanzapine (FIG. 14F). The data were obtained from the study described in Example 3, plotting the results for longer PK time points (0-12 hrs).

Figure 15A:
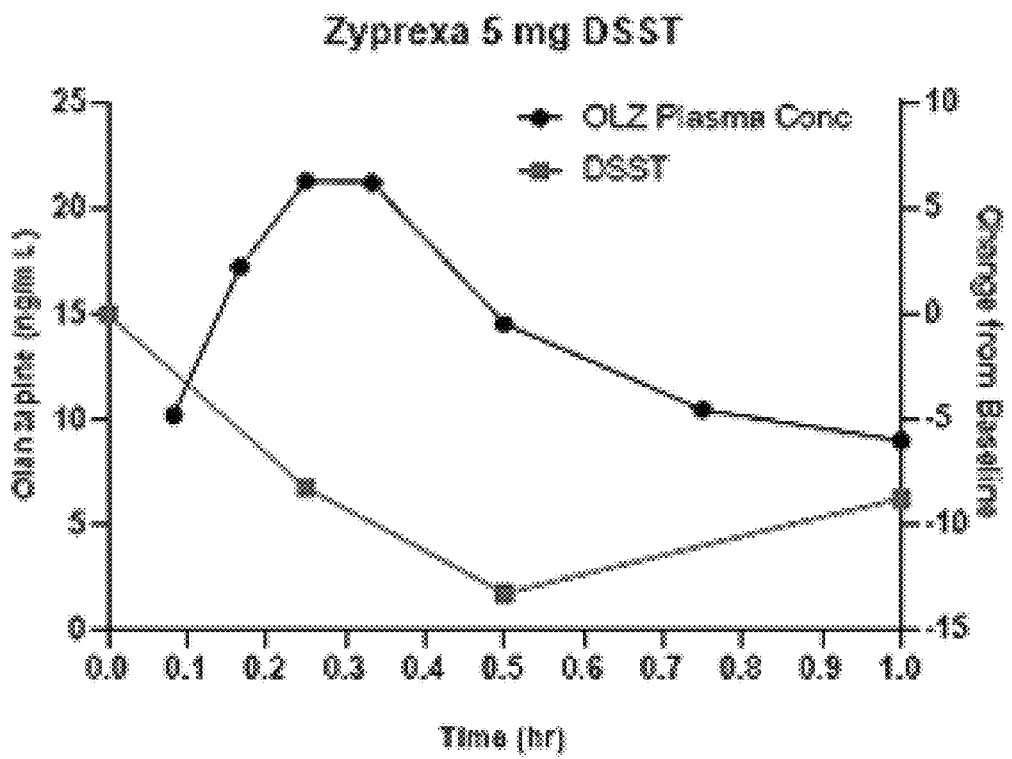
Figure 15B:
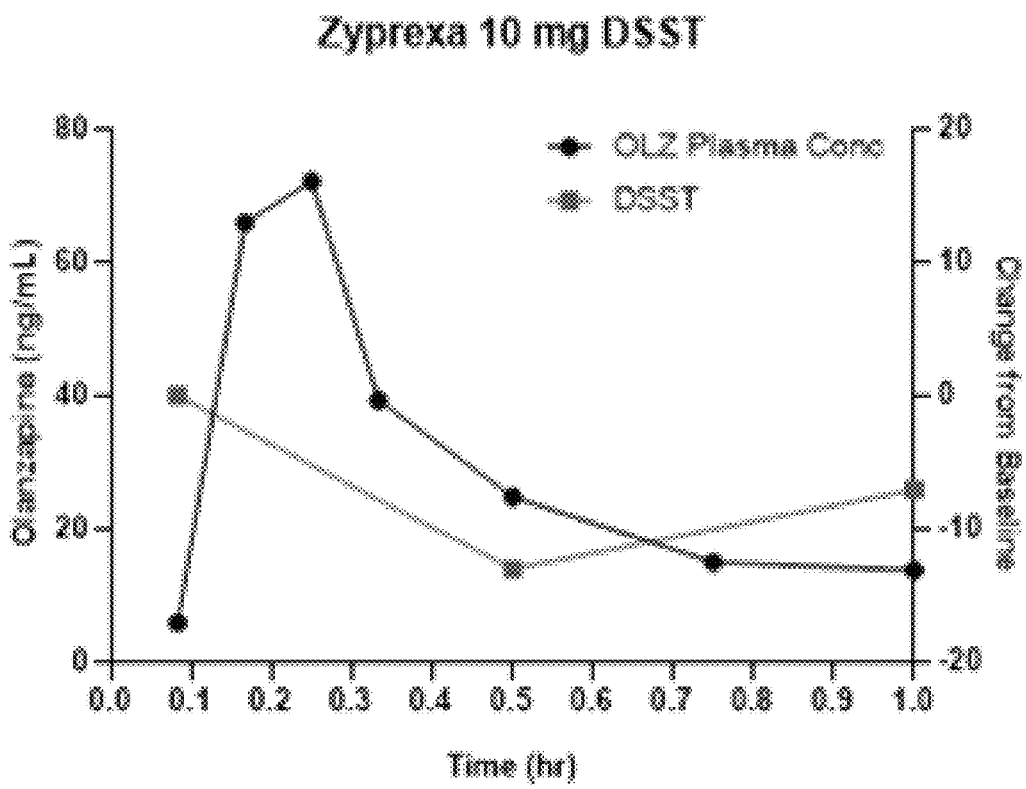
Figure 15C:
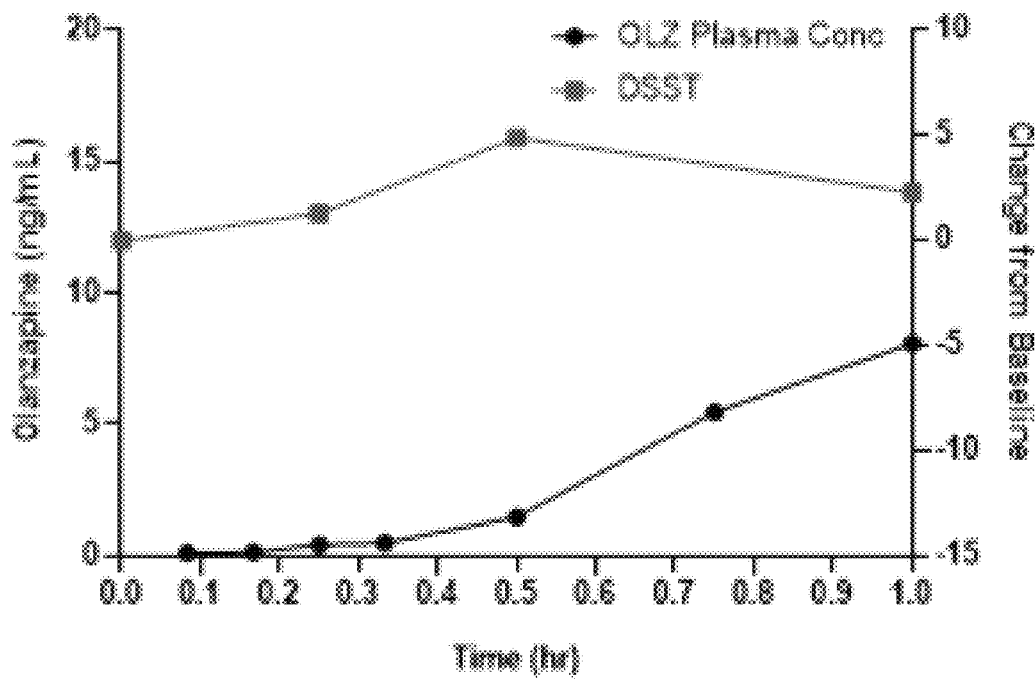
Figure 15D:
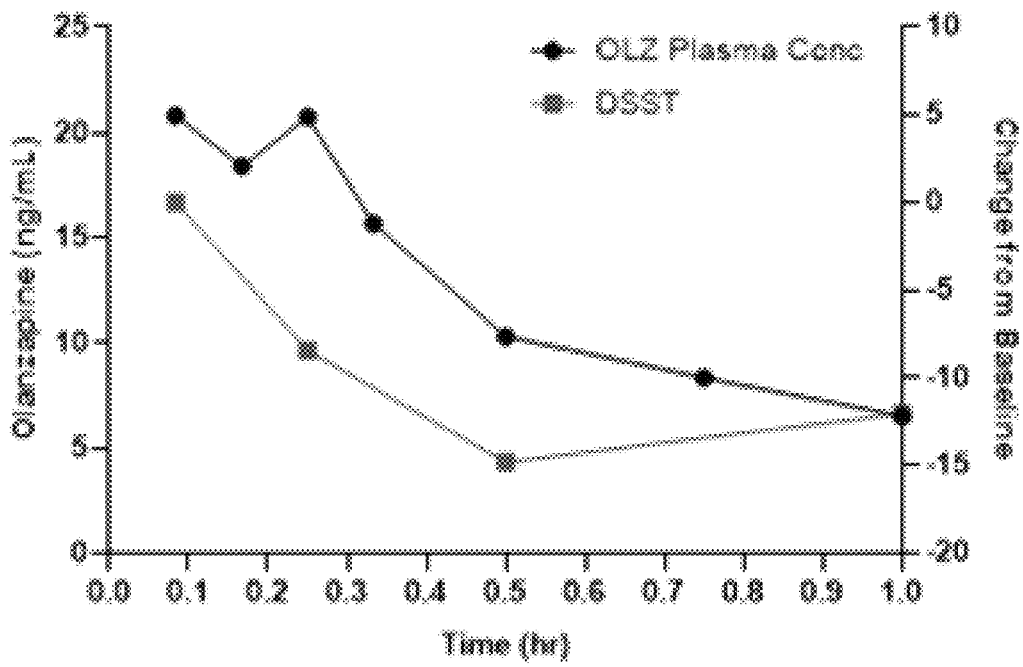
Figure 15E:
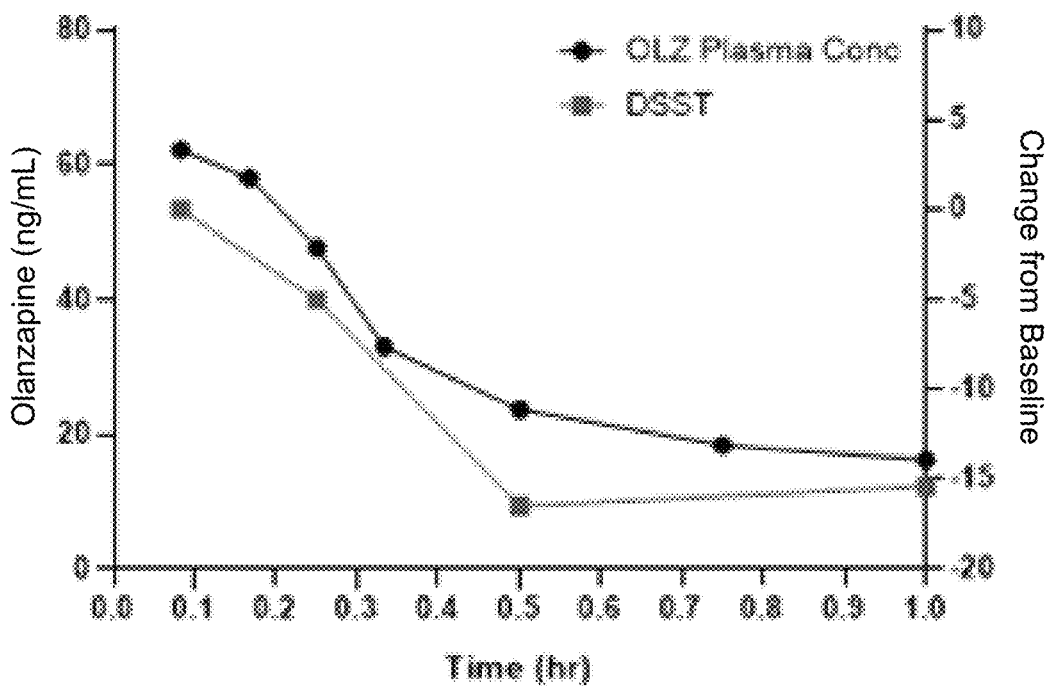
Figure 15F:
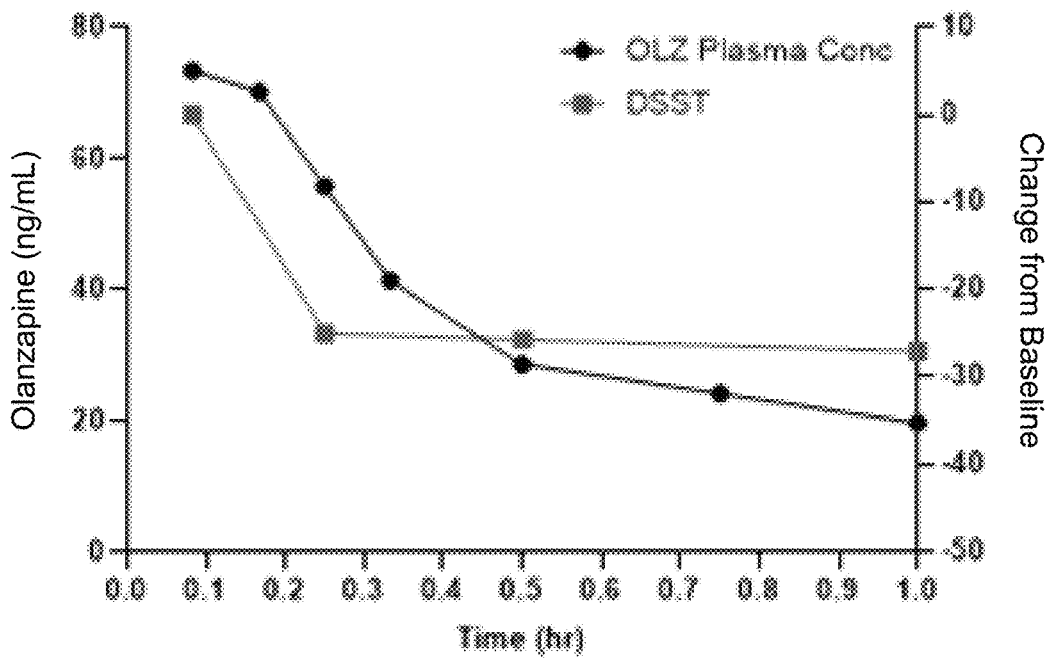

FIGS. 15A-15F show mean DSST Score-Time Curves together with mean Plasma Concentration-Time Curves measured in human subjects following intramuscular administration of 5 mg olanzapine (FIG. 15A), intramuscular administration of 10 mg olanzapine (FIG. 15B), oral administration of 10 mg olanzapine (FIG. 15C), intranasal administration of 5 mg olanzapine (FIG. 15D), intranasal administration of 10 mg olanzapine (FIG. 15E), or intranasal administration of 15 mg olanzapine (FIG. 15F). The data were obtained from the study described in Example 3, plotting the results for shorter PK time points (0-1 hr).

Figure 16A:
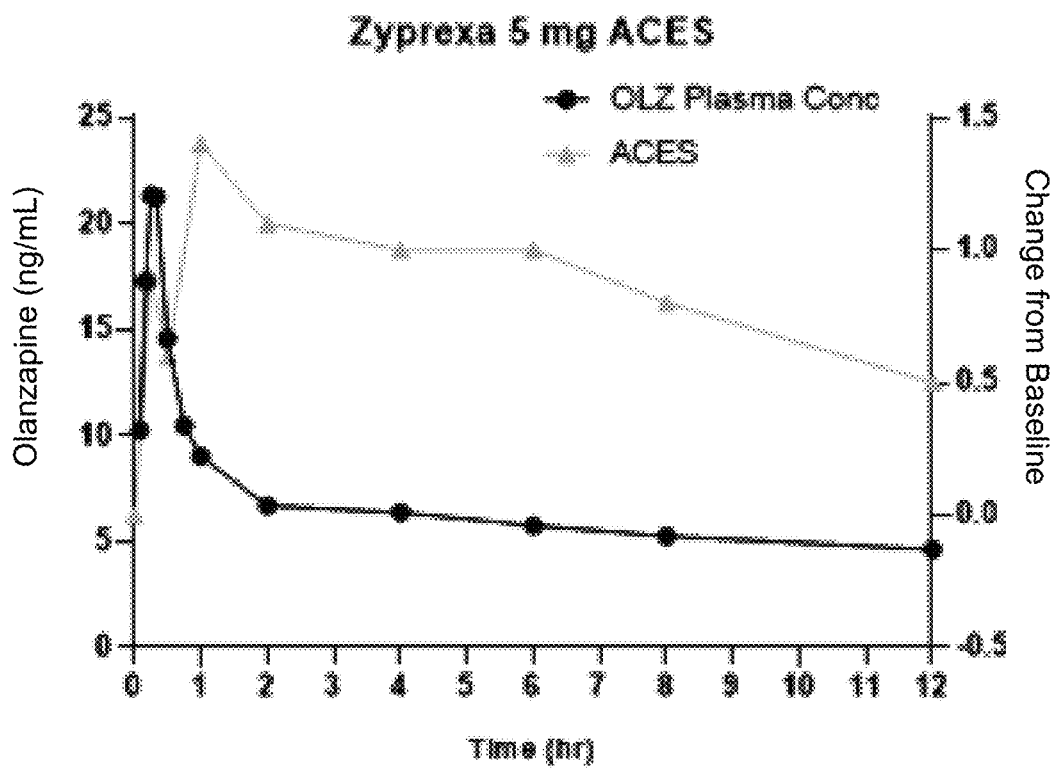
Figure 16B:
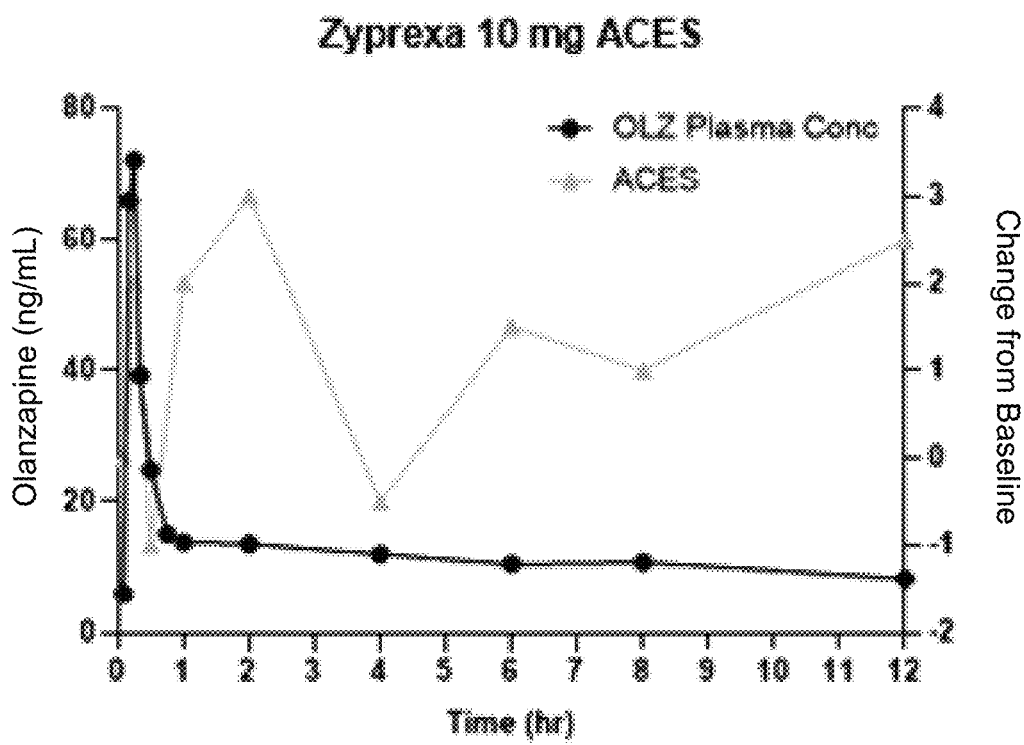
Figure 16C:
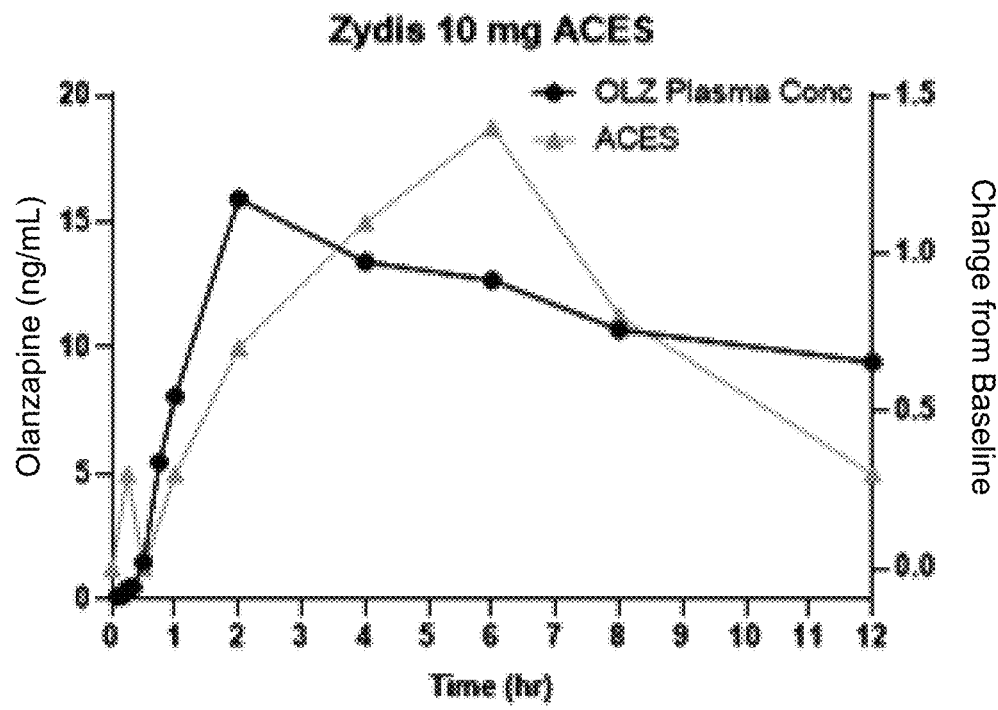
Figure 16D:
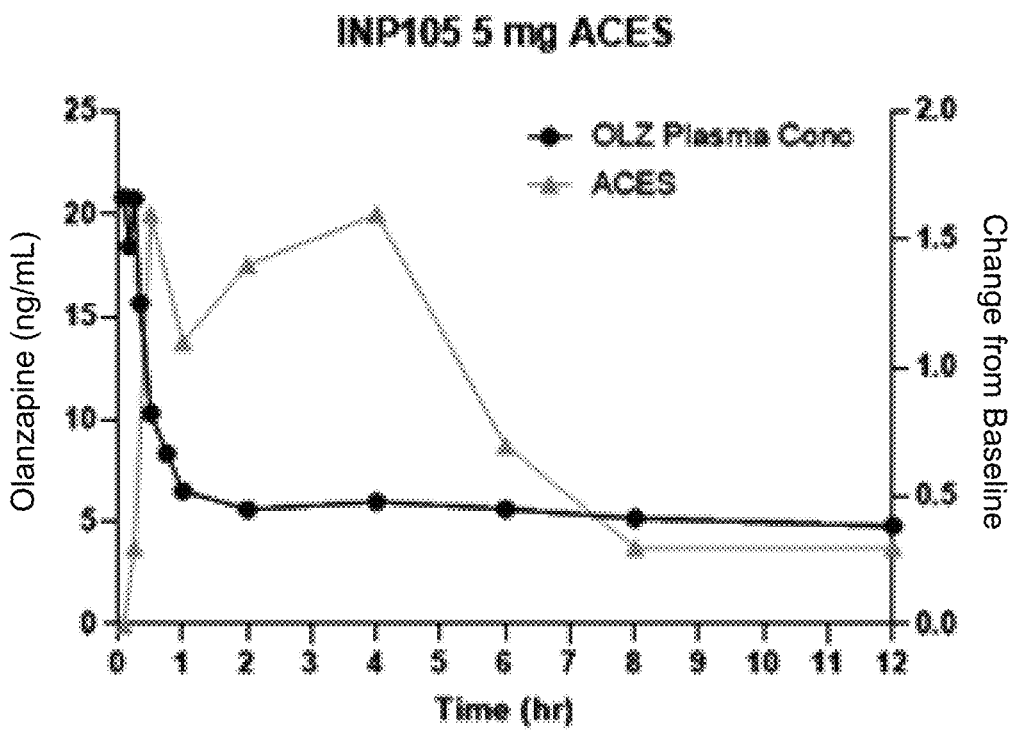
Figure 16E:
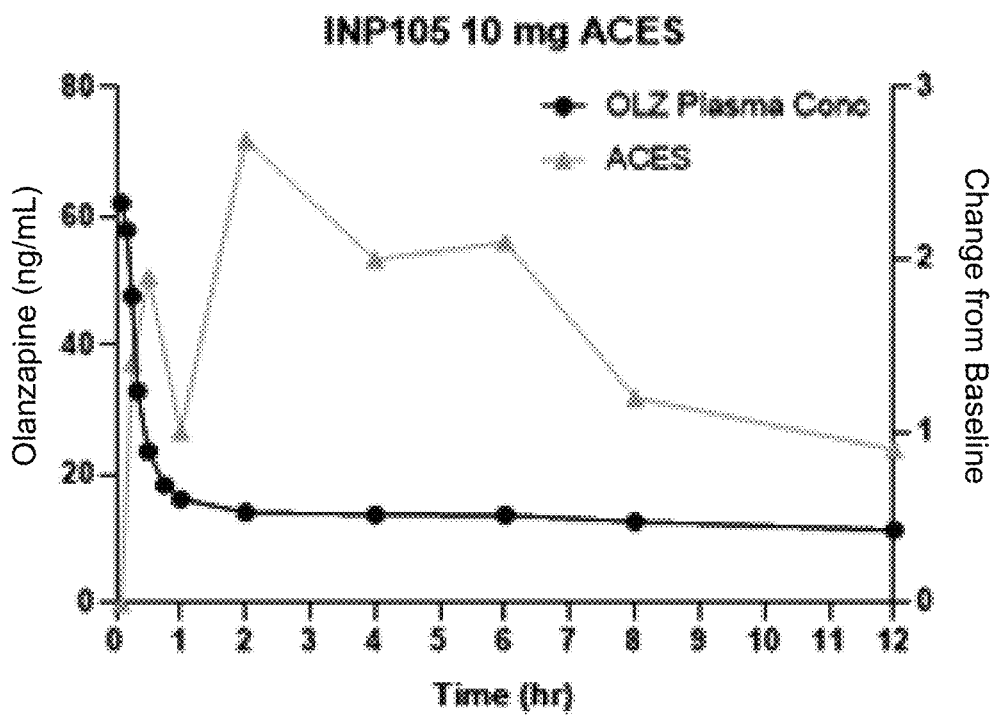
Figure 16F:
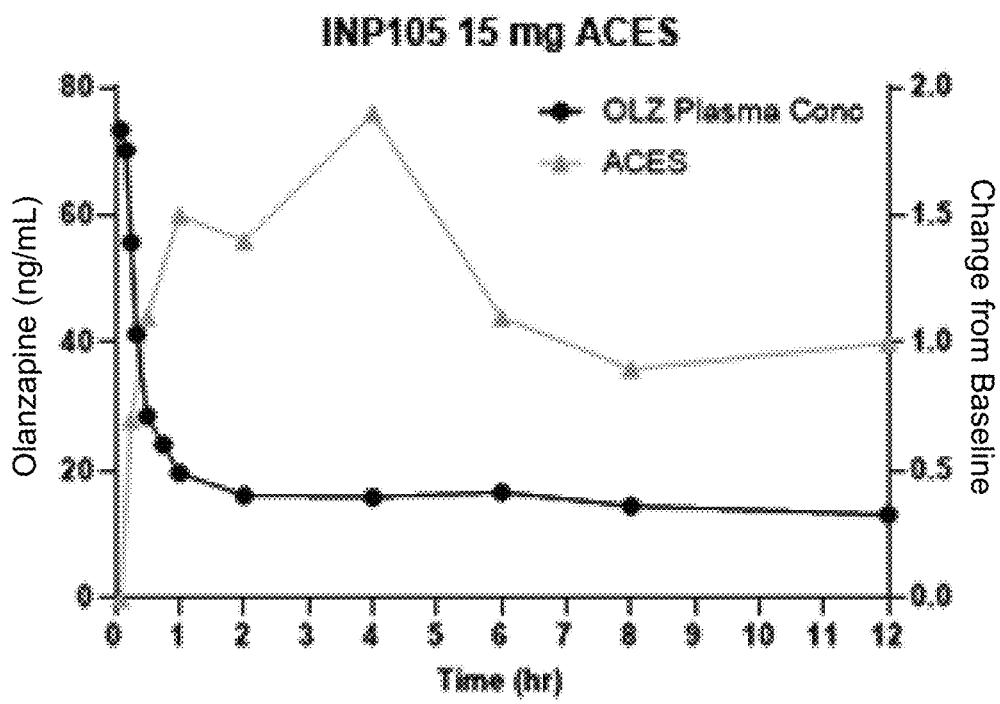

FIGS. 16A-16F show mean ACES Score-Time Curves together with mean Plasma Concentration-Time Curves measured in human subjects following intramuscular administration of 5 mg olanzapine (FIG. 16A), intramuscular administration of 10 mg olanzapine (FIG. 16B), oral administration of 10 mg olanzapine (FIG. 16C), intranasal administration of 5 mg olanzapine (FIG. 16D), intranasal administration of 10 mg olanzapine (FIG. 16E), or intranasal administration of 15 mg olanzapine (FIG. 16F). The data were obtained from the study described in Example 3, plotting the results for longer PK time points (0-12 hrs).

Figure 17A:
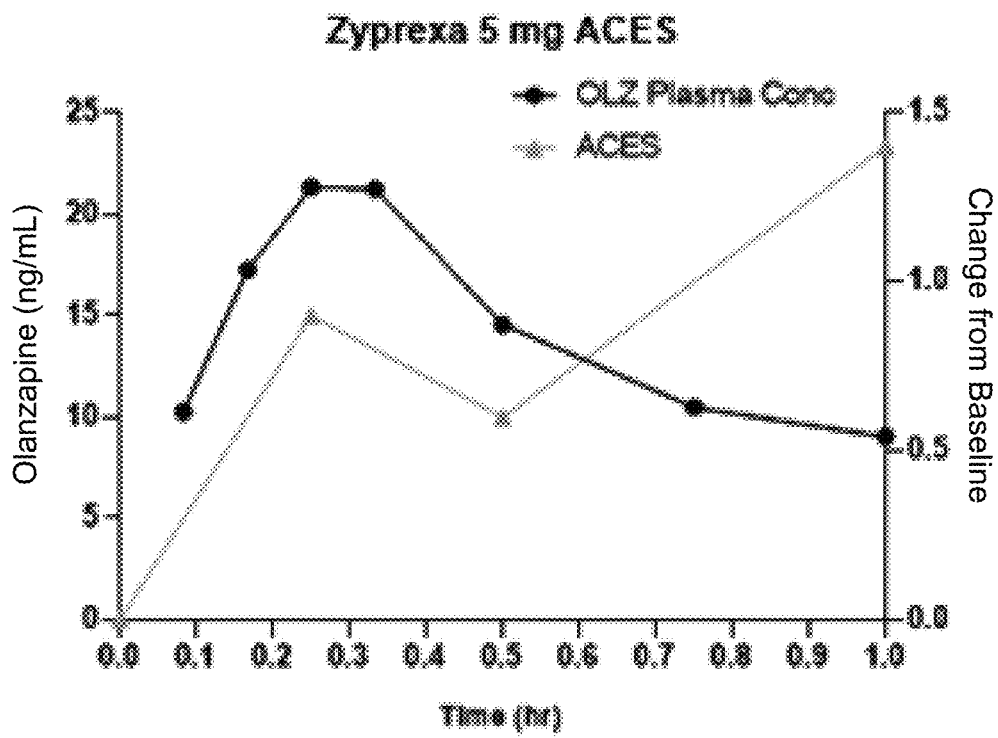
Figure 17B:
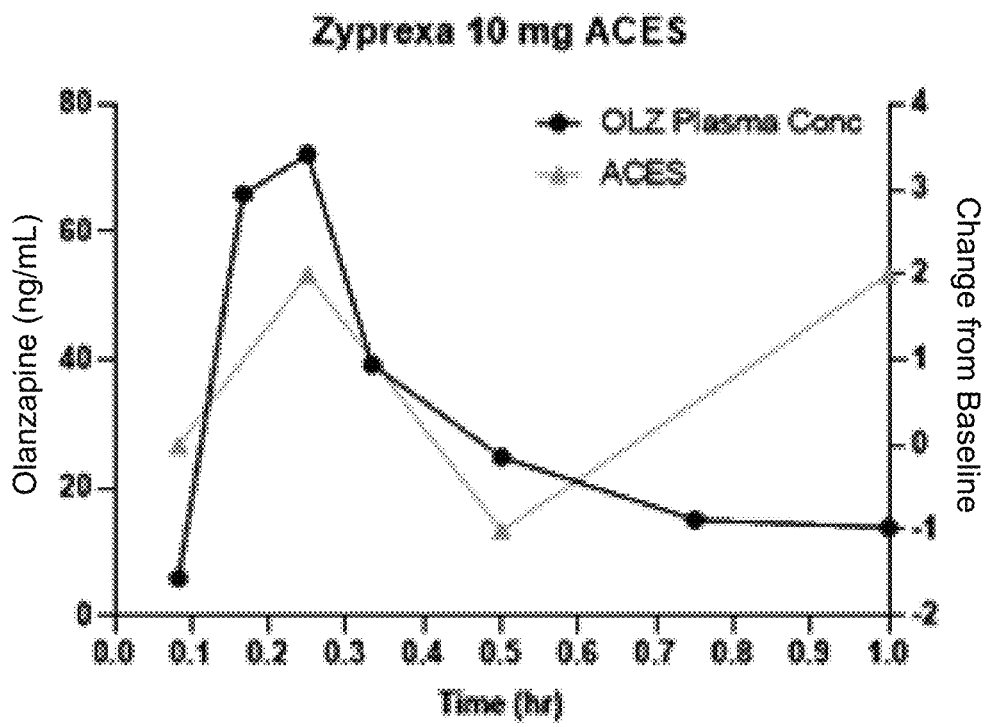
Figure 17C:
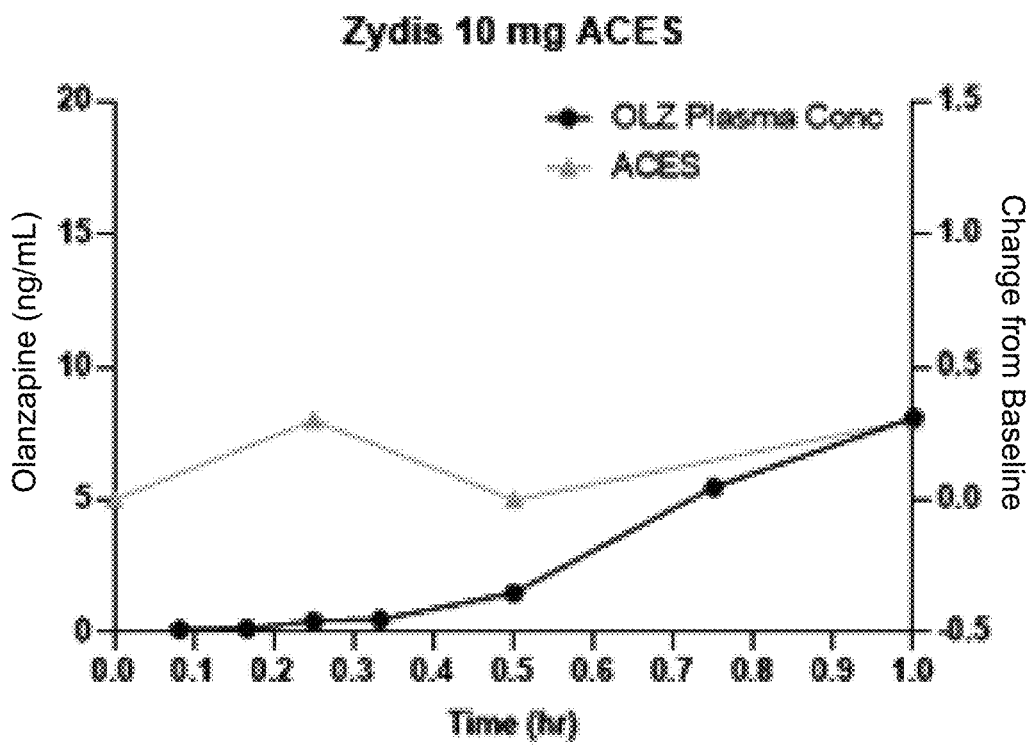
Figure 17D:
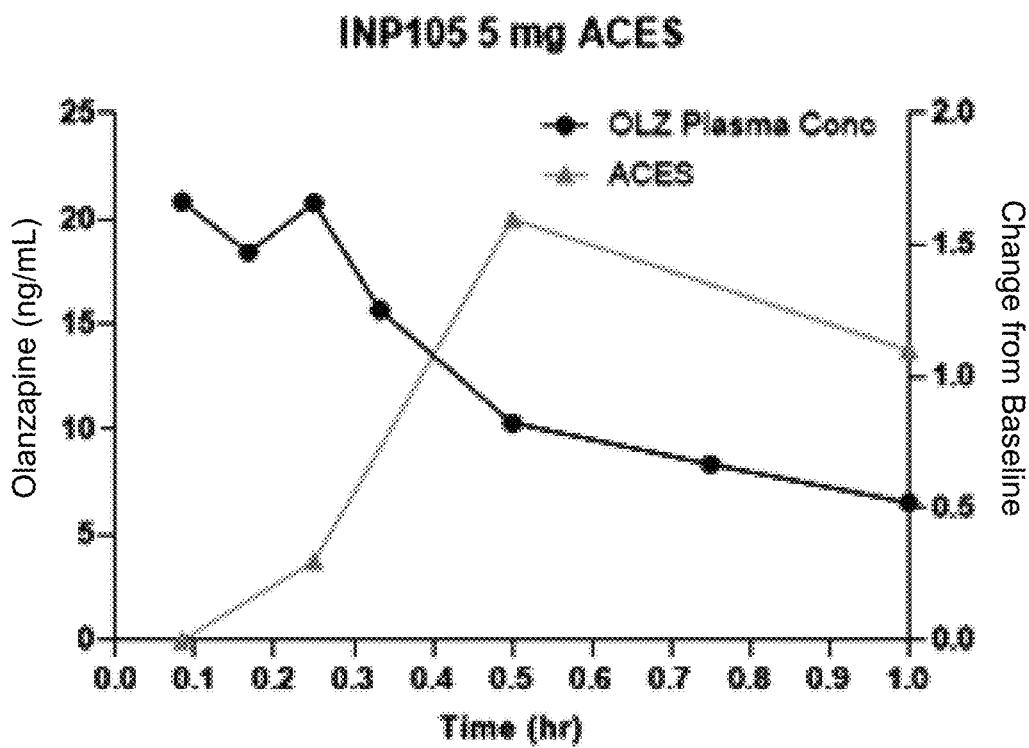
Figure 17E:
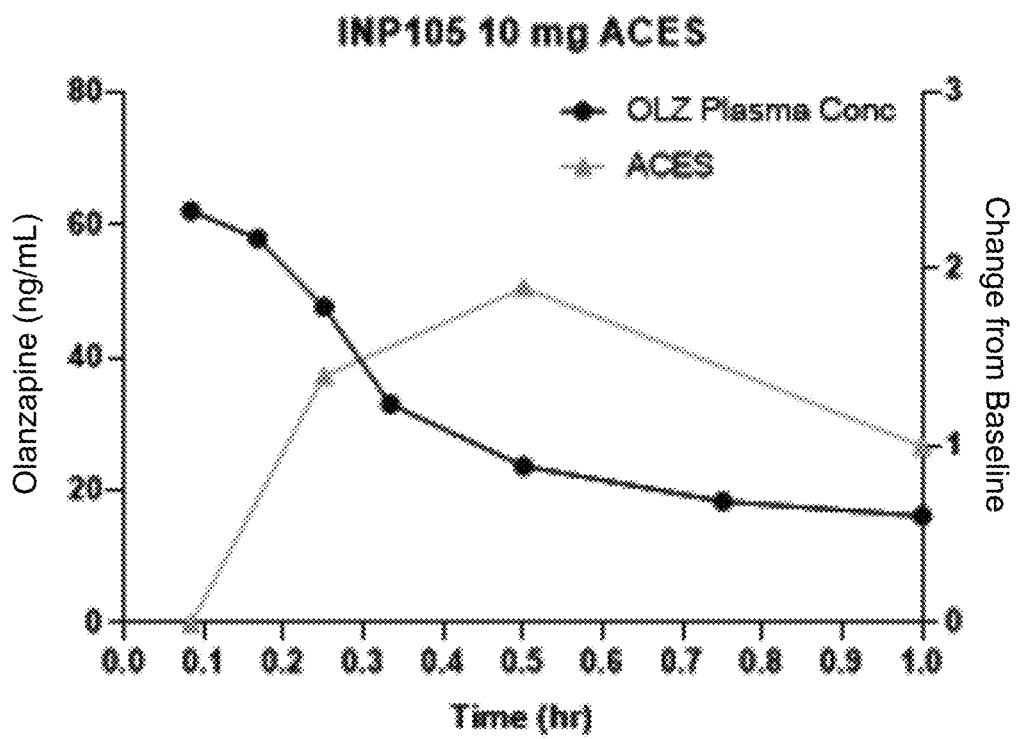
Figure 17F:
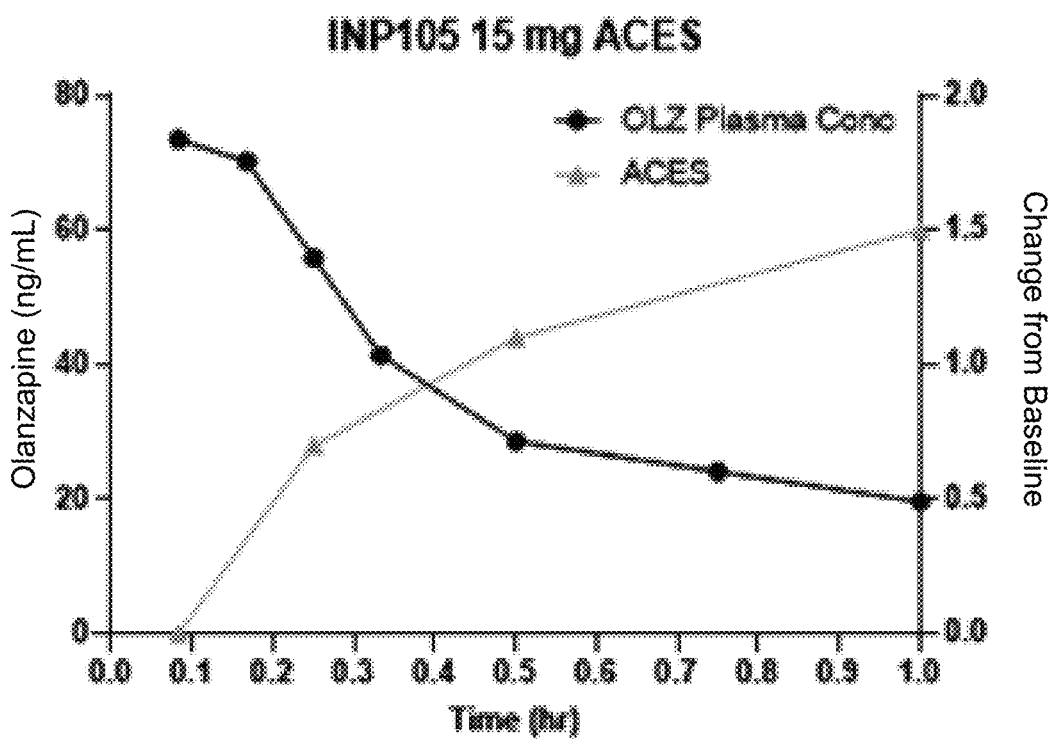

FIGS. 17A-17F show mean ACES Score-Time Curves together with mean Plasma Concentration-Time Curves measured in human subjects following intramuscular administration of 5 mg olanzapine (FIG. 17A), intramuscular administration of 10 mg olanzapine (FIG. 17B), oral administration of 10 mg olanzapine (FIG. 17C), intranasal administration of 5 mg olanzapine (FIG. 17D), intranasal administration of 10 mg olanzapine (FIG. 17E), or intranasal administration of 15 mg olanzapine (FIG. 17F). The data were obtained from the study described in Example 3, plotting the results for shorter PK time points (0-1 hr).

5. DETAILED DESCRIPTION

5.1. Definitions

Unless defined otherwise, all technical and scientific terms used herein have the meaning commonly understood by a person skilled in the art to which this invention belongs.

A pharmaceutical composition is "dry" if it has a residual moisture content of no more than 5 wt %.

5.2. Other Interpretational Conventions

Ranges: throughout this disclosure, various aspects of the invention are presented in a range format. Ranges include the recited endpoints. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Unless specifically stated or apparent from context, as used herein the term "or" is understood to be inclusive.

Unless specifically stated or apparent from context, as used herein, the terms "a", "an", and "the" are understood to be singular or plural. That is, the articles "a" and "an" are used herein to refer to one or to more than one (i.e., to at least one) of the grammatical object of the article. By way of example, "an element" means one element or more than one element.

In this disclosure, "comprises," "comprising," "containing," "having," "includes," "including," and linguistic variants thereof have the meaning ascribed to them in U.S. Patent law, permitting the presence of additional components beyond those explicitly recited.

Unless specifically stated or otherwise apparent from context, as used herein the term "about" is understood as within a range of normal tolerance in the art, for example within 2 standard deviations of the mean and is meant to encompass variations of ±20% or ±10%, more preferably ±5%, even more preferably ±1%, and still more preferably ±0.1% from the stated value.

5.3. Summary of Experimental Observations

We conducted two single dose PK studies in cynomolgus monkeys to examine the pharmacokinetics following administration of multiple powder olanzapine formulations delivered by the intranasal route using a non-human primate precision olfactory delivery ("nhpPOD" or "NHP-POD") Device. The formulations examined included an unmodified crystalline powder, a formulation containing HPMC and 1,2-distearoyl-sn-glycero-3-phosphocholine (DSPC), and a formulation containing HPMC and Pluronic F68. The placebo control, also delivered intranasally by the nhpPOD Device, was microcrystalline cellulose.

The PK results show that intranasal delivery using the nhpPOD Device of a formulation of olanzapine containing HPMC and DSPC results in similar plasma exposure (AUC) and $T_{max}$ as intramuscular administration of olanzapine. In comparison to unformulated olanzapine (Cipla API), the formulated (HPMC/DSPC) powder results in a 1.7-fold higher AUC and a 2.8-fold shorter $T_{max}$.

To further optimize the olanzapine (OLZ) formulations, approximately thirty different formulations were designed and manufactured for upper nasal delivery by a POD device. The formulations were tested, characterized and optimized for POD device compatibility. Stabilizers, permeation enhancers, particle size and manufacturing processes were also screened as part of the formulation development process.

In total, twenty of the formulations were evaluated in single dose PK studies in rat (data not shown) and non-human primates (NHPs). The results showed that administration of formulations F-OLZ #2, F-OLZ #5 and F OLZ #6 to NHPs via the NHP-POD device resulted in rapid uptake with short time to median $T_{max}$ (15, 15 and 23 min, respectively) and less than 7 min to exceed 40 ng/mL, which is approximately the plasma concentration achieved in stable non-agitated patients following 3×10 mg intramuscular injections (as reported in the Zyprexa NDA 21253). Delivery of formulations F-OLZ #1, F OLZ #3 and F-OLZ #4 to NHPs via the NHP-POD device resulted in slower plasma uptake compared to the other 3 formulations, but still resulted in $T_{max}$ of 30-60 min, which is significantly faster than time to peak plasma concentration for oral olanzapine (OLZ) tablets or oral disintegrating tablets ($T_{max}$~5-8 hrs).

The pharmacodynamic effects of each nasal olanzapine formulation administered to NHPs were collected throughout each study. For lead formulations with shorter time to $T_{max}$, visible calming, though not excessive sedation, was observed in the NHPs by the 7 min blood draw, and the effect continued through 24 hours. This reported calming effect was observed in all groups that received nasal olanzapine, though the time to onset was delayed and effect was less pronounced in groups with slower time to peak plasma concentration and with lower peak exposure.

Pharmacokinetics and pharmacodynamics effects of intranasal administration of formulation F-OLZ #2, an olanzapine formulation containing HPMC and DSPC (INP105), were further tested in healthy human subjects in a phase 1 clinical trial. In this study, intranasal delivery of the olanzapine formulation resulted in similar or slightly higher plasma exposure (AUC) and maximum $C_{max}$ as compared to the IM administered olanzapine at the same dose. Furthermore, the median $T_{max}$ after intranasal delivery of the formulation was significantly shorter than the median $T_{max}$ measured for the IM administered or orally administered olanzapine, demonstrating fast and effective absorption of olanzapine across nasal epithelium.

Pharmacodynamic effects were measured using three standardized behavioral tests—a Visual Analogue Scale (VAS); Agitation/Calmness Evaluation Scale (ACES); and Digit Symbol Substitution Test (DSST). The tests all showed that intranasal administration of olanzapine induces calming effects similar to or better than IM or oral administration of olanzapine. Furthermore, behavioral effects of olanzapine was observed significantly earlier in the subject groups treated with intranasal olanzapine (INP105) or IM olanzapine (Zyprexa IM), compared to the subject group treated with oral olanzapine (Zyprexa Zydis). This is consistent with the pharmacokinetic results where intranasal delivery of olanzapine was found to have significantly shorter median $T_{max}$ as compared to IM or oral delivery. These results show that intranasal delivery of olanzapine can be an effective method for acute treatment of agitation.

5.4. Methods of Treating Agitation

Accordingly, in a first aspect methods are provided for acute treatment of agitation. The methods comprise intranasally administering an effective dose of a dry pharmaceutical composition comprising olanzapine to a subject exhibiting agitation.

5.4.1. Dry Powder Composition

In typical embodiments, the dry pharmaceutical composition is a powder.

In typical embodiments, the median diameter of the olanzapine particle size distribution (D50) in the powder, as measured by laser diffraction particle size analyzer, such as the Malvern Panalytical Mastersizer 3000, is 1 μm-500 μm. In some embodiments, the median diameter of the olanzapine particle size distribution (D50) in the powder is 1 μm-250 μm, 1 μm-100 μm, 1 μm-75 μm, 1 μm-50 μm, 1 μm-25 μm, 1 μm-20 μm, 1 μm-15 μm, or 2 μm-15 μm. In certain embodiments, the median diameter of the olanzapine particle size distribution (D50) in the composition is 2 μm-5 μm or 7.5 μm-15 μm.

In some embodiments, the powder comprises olanzapine in a crystalline form. In some embodiments, the powder comprises olanzapine in amorphous form. In some embodiments, the dry pharmaceutical composition comprises olanzapine in both crystalline and amorphous forms. In some embodiments, the dry pharmaceutical composition comprises olanzapine in a partially crystalline and partially amorphous form. In particular embodiments, the olanzapine is an amorphous solid obtained by spray-drying.

In various embodiments, the dry powder composition comprises no more than 70 wt % olanzapine. In some embodiments, the dry pharmaceutical composition comprises no more than 60 wt % olanzapine. In some embodiments, the composition comprises 10-70% wt % olanzapine, 20-70 wt % olanzapine, 10-60% wt % olanzapine, 20-60 wt % olanzapine, 25-55 wt % olanzapine, 30-50 wt % olanzapine, 30-40 wt % olanzapine or 40-50 wt % olanzapine.

In some embodiments, the dry powder composition further comprises a stabilizer selected from the group consisting of: hydroxypropylmethylcellulose (HPMC), polyvinyl caprolactam-polyvinyl acetate-polyethylene glycol graft copolymer (Soluplus), vinyl pyrrolidine-vinyl acetate copolymer (Kollidon VA64), polyvinyl pyrrolidine K30 (Kollidon K30), polyvinyl pyrollidone K90 (Kollidon K90), hydroxypropylcellulose (HPC), hydroxypropyl betacyclodextrin (HPBCD), mannitol, and lactose monohydrate. In some embodiments, the stabilizer is hydroxypropylmethylcellulose (HPMC).

In some embodiments, the dry power composition further comprises a permeation enhancer selected from the group consisting of the permeation enhancer is selected from the group consisting of: n-tridecyl-β-D-maltoside, n-dodecyl-β-D-maltoside, 1,2-distearoyl-sn-glycero-3-phosphocholine (DSPC), 1,2-dipalmitoyl-sn-glycero-3-phosphocholine (DPPC), 1,2-dioleoyl-sn-glycero-3-phosphocholine (DOPC), propylene glycol, disodium EDTA, PEG400 monostearate, polysorbate 80, and macrogol (15) hydroxystearate. In some embodiments, the permeation enhancer is 1,2-distearoyl-sn-glycero-3-phosphocholine (DSPC).

In some embodiments, the dry powder composition comprises both HPMC and DSPC.

In various embodiments, the dry powder composition further comprises a nonionic surfactant. In certain embodiments, the nonionic surfactant is an alkyl maltoside. In particular embodiments, the alkyl maltoside is n-dodecyl β-D-maltoside. In some embodiments, the nonionic surfactant is present in the dry powder composition at 0.1-10 wt %, more typically 1-5 wt %. In particular embodiments, the nonionic surfactant is present at 1 wt %.

In some embodiments, the nonionic surfactant is Pluronic PF68. In some embodiments, the nonionic surfactant is present in the dry powder composition at 20-40 wt %, more typically 25-35 wt %. In particular embodiments, the nonionic surfactant is present at 31 wt %.

In some embodiments, the dry powder composition further comprises an antioxidant selected from the group consisting of alpha tocopherol, ascorbic acid, ascorbyl palmitate, bronopol butylated hydroxyanisole (BHA), butylated hydroxytoluene (BHT), citric acid monohydrate, sodium ascorbate, ethylene diainetetraacetic acid, fumaric acid, malic acid, methionine, propionic acid, sodium metabisulfite, sodium sulfite, sodiumthiosulfate, thymol, and vitamin E polyethylene glycol succinate.

In some embodiments, the dry powder composition further comprises an acid. In certain embodiments, the acid is citric acid. In some embodiments, the acid is present in the dry powder composition at 10-20 wt %, more typically 15-20 wt %. In particular embodiments, citric acid is present at 18 wt %.

In various embodiments, the dry powder composition further comprises a salt of a monovalent inorganic cation. Typically, the salt is NaCl. In some embodiments, the composition comprises 1-5 wt % NaCl, or 2-4 wt % NaCl.

In some embodiments, the dry powder composition comprises less than 3 wt %, less than 2.5 wt %, less than 2 wt %, less than 1.5 wt %, less than 1 wt %, less than 0.9 wt %, less than 0.8 wt %, less than 0.7 wt %, less than 0.6 wt %, or less than 0.5 wt % water.

In currently preferred embodiments, the dry powder composition comprises 50 wt % olanzapine, 42 wt % HPMC, and 8% DSPC. In some embodiments, the dry powder composition is a spray dried composition that comprises amorphous olanzapine. In some embodiments, olanzapine is spray dried in the presence of HPMC and/or DSPC. In other embodiments, HPMC and/or DSPC is added after spray drying of olanzapine.

5.4.2. Device

In the methods described herein, the dose is administered by an intranasal delivery device that delivers a powder to the nasal cavity.

In some embodiments, the intranasal delivery device is a handheld, manually actuated, metered-dose intranasal administration device. In certain embodiments, the device is manually actuated, propellant-driven metered-dose intranasal administration device. In particular embodiments, the dry pharmaceutical composition is, prior to device actuation, encapsulated within a capsule present within the device. In some embodiments, the dry pharmaceutical composition is stored within a dose container that is removably coupled to the device prior to device actuation. For example, the dose container may be inserted into a portion of the device or may be coupled to the device such that the dose container is in fluid communication with the device.

In various embodiments, the intranasal delivery device includes a housing body, a propellant canister housed within the housing body, a compound chamber containing a drug compound or designed to receive a drug compound, a channel in fluid communication with the propellant canister and the compound chamber, and an outlet orifice at a distal end of the channel. In this configuration, propellant released from the canister travels through the channel, contacts the drug compound in the compound chamber, and propels the drug compound out the outlet orifice for delivery into an upper nasal cavity.

In typical embodiments, the intranasal delivery device is capable of delivering the dry pharmaceutical composition to the upper nasal cavity.

5.4.2.1. Nasal Drug Delivery Device

In various embodiments, the intranasal administration device is a non-human primate precision olfactory delivery ("nhpPOD") device described in FIGS. 7A-E, also described in U.S. Pat. No. 9,550,036, incorporated by reference in its entirety herein. In one embodiment, the intranasal device is one of the embodiments of FIGS. 1, 2, and 9 of U.S. Pat. No. 9,550,036. In these embodiments, the drug compound is loaded directly into the compound chamber.

Figure 6:
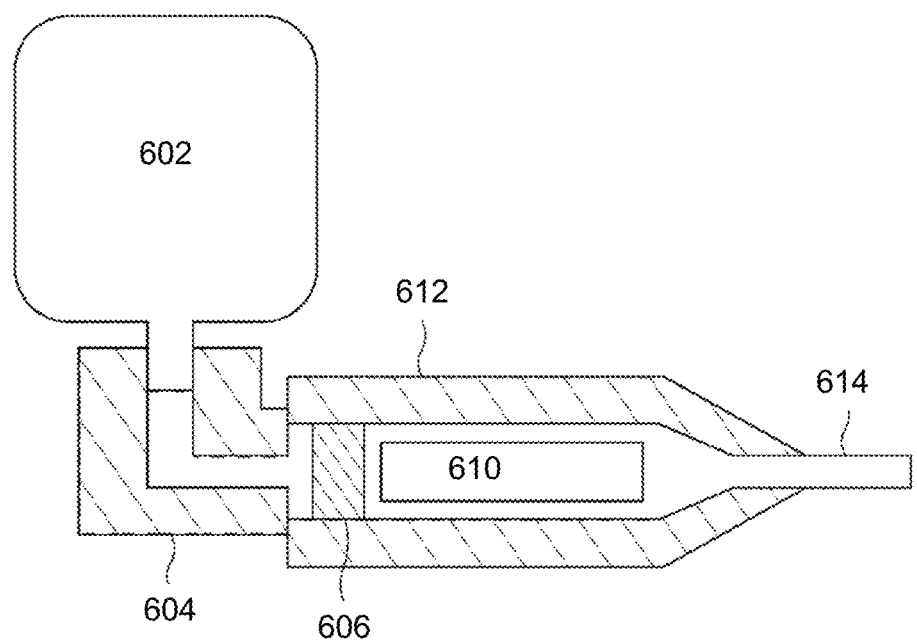
FIG. 6 illustrates an example of a non-human primate precision olfactory delivery device, in accordance with one or more embodiments.

An example nhpPOD device is shown in FIG. 6.

With reference to FIG. 6, a metered dose inhaler (MDI) canister 602 dispensing 25 µl hydrofluoroalkane is attached to the plastic actuator 604. The actuator is in gas communication with a polytetrafluoroethylene frit 1704 which has a 50 µm pore size. The frit 606 is in communication with the dose holding cylinder 610 which is placed inside the body 612 of the POD in order to create an aerosolized flow. On actuation, the HFA propellant 802 is converted to a gas by passing through the frit material 606 and then mixes with the dose 610; the dose and propellant mixture then exits from the 23 gauge stainless steel tubing nozzle 614 which is covered with a fluorinated ethylene-propylene liner that is placed over the outside of the metal tip in order to protect the nasal epithelia from being damaged by the nozzle 614 during use. In one embodiment, the dose 610 is loaded directly into the body 612 without a holding cylinder.

5.4.2.2. Medical Unit Dose Container

In various embodiments, the intranasal administration device is a medical unit dose container as described in US 2016/0101245 A1, the disclosure of which is incorporated herein by reference in its entirety.

5.4.2.3. Intranasal Device with Inlet Interface

In various embodiments, the intranasal administration device is a medical unit dose container as described in U.S. application Ser. No. 16/198,312, filed Nov. 21, 2018, the disclosure of which is incorporated herein by reference in its entirety and repeated below for completeness.

Figure 5A:
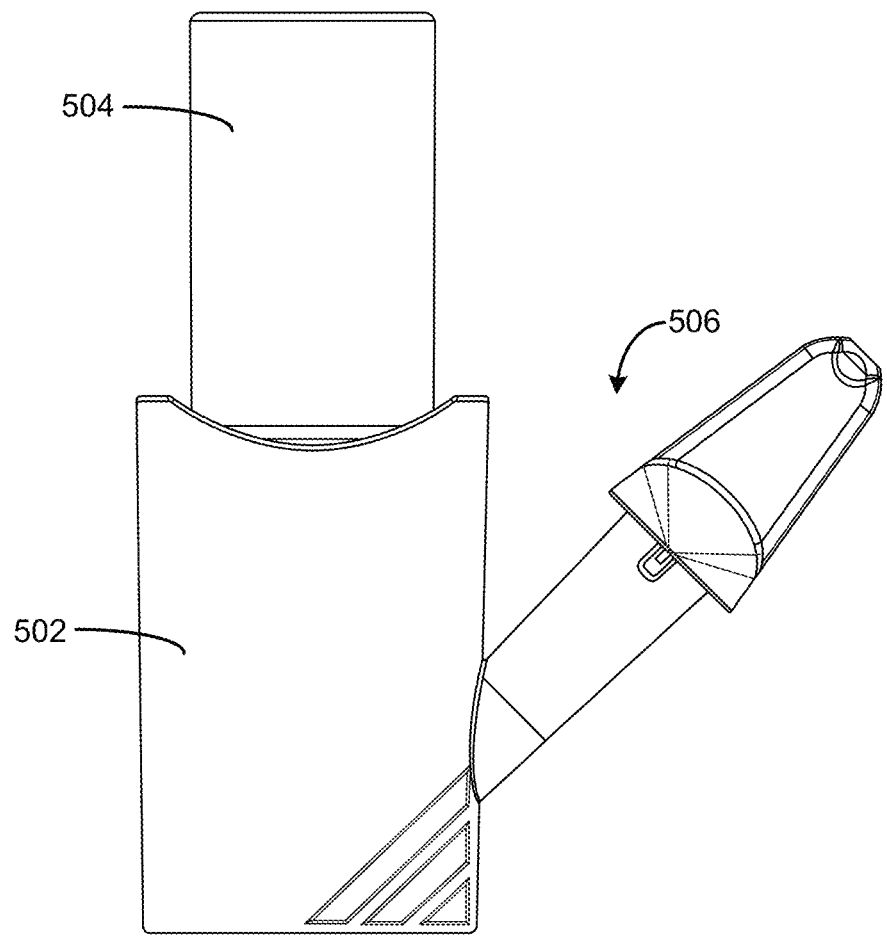
FIG. 5A is an intranasal drug delivery device, in accordance with one or more embodiments.
Figure 5B:
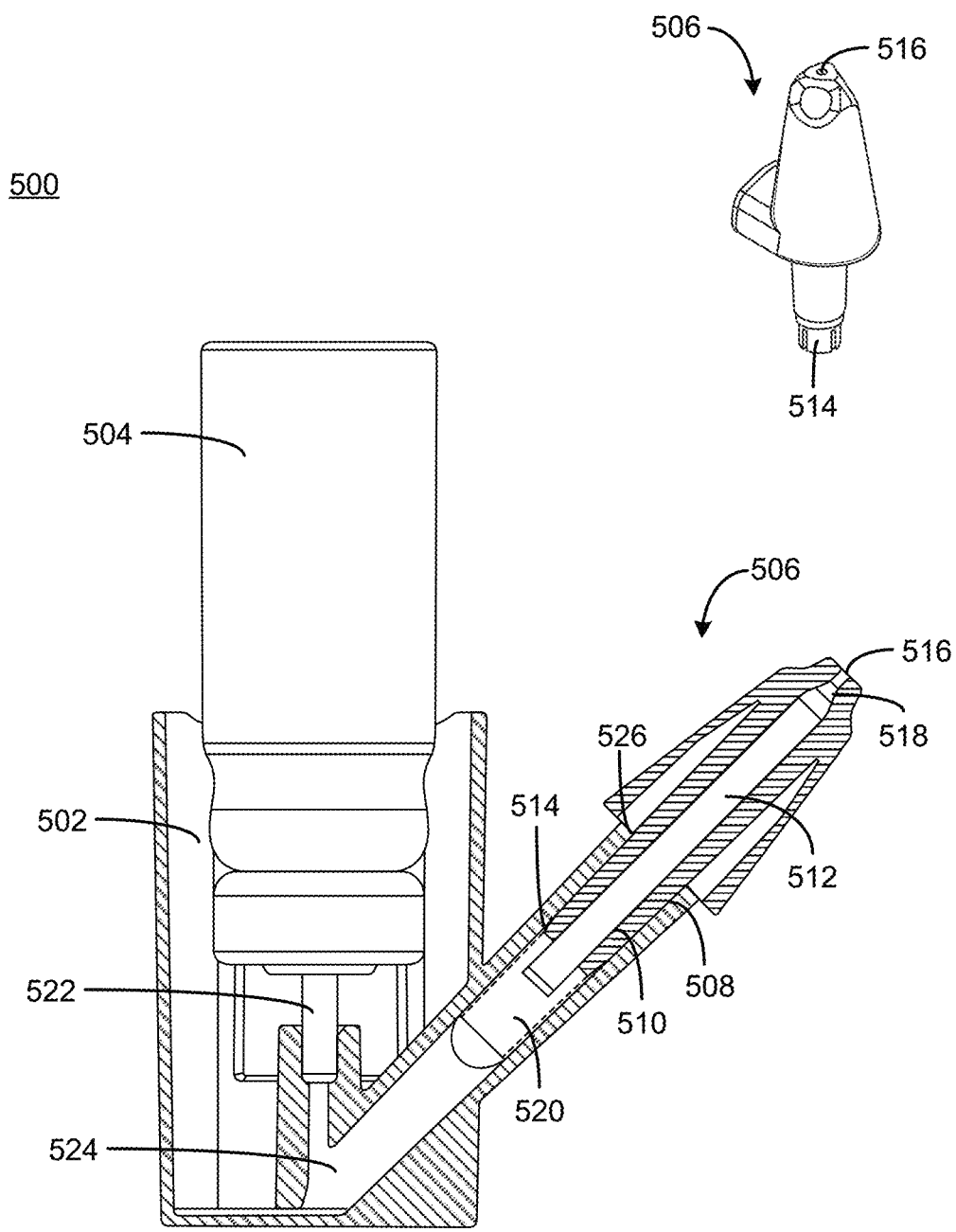
FIG. 5B illustrates a partial cross-sectional view of the intranasal delivery device with removable tip attached, and a separate perspective view of the removable tip in its detached state, in accordance with one or more embodiments.

As shown in FIGS. 5A and 5B, the intranasal device 500 is designed to deliver a consistent mass of compound into the nasal cavity. For example, but not limited to, the compound may be an intranasal formulation in a powder form. The device 500 targets a specific region of the nasal cavity utilizing a narrow, targeted delivery plume. Specifically, the device 500 provides the compound to the upper one third of the nasal cavity. In one embodiment, the device 500 is used to administer the compound into the upper nasal cavity of a human. The upper nasal cavity includes the olfactory region and the middle and upper turbinate regions. In another embodiment, the device 500 is used to administer the compound into the upper nasal cavity of a non-human primate. The device 500 is also designed to simplify clinician loading of the compound into the device 500 and use thereof. The device 500 may be re-used to administer several doses of the compound.

FIG. 5B illustrates a partial cross-sectional view of the device 500 for delivering a compound intranasally, with coupled tip, and separately, a perspective view of the tip when uncoupled. In the embodiment of FIG. 5B, the device 500 includes an actuator body 502, a propellant canister 504, and a tip 506. The tip 506 includes an outer wall 508 and an inner wall 510, an exit channel 512, an inlet interface 514, one or more grooves 528 (shown in FIG. 5C), an outlet orifice 516, and a nozzle 518. FIG. 5B illustrates the compound container 520 coupled to the inlet interface 514. The compound contained in the compound container 520 may be a liquid or a powder. In the embodiment of FIG. 5B, the compound is a powder.

As shown in FIG. 5B, the device 500 includes a propellant canister 504 positioned within the actuator body 502. The propellant canister 504 contains propellant. In one embodiment, the propellant may be pressurized. The propellant is a fluid, for example, a liquid or gas. In one aspect, the propellant is a liquid. In another aspect, the propellant is a gas. Propellants include pharmaceutically suitable propellants. Some examples of pharmaceutically suitable propellants include hydrofluoroalkane (HFA) including but not limited to HFA, HFA 227, HFA 134a, HFA-FP, HFA-BP and like HFAs. In one aspect, the propellant is liquid HFA. In another aspect, the propellant is gaseous HFA. Additional examples of suitable propellants include nitrogen or chloroflourocarbons (CFC). Additionally, propellants may be pressurized air (e.g. ambient air). The canister 504 may be a metered dose inhaler (MDI) device that includes a pressurized canister and metering valve 522 (including stem) to meter the propellant upon actuation. In one embodiment, a pump fitment (not shown) secures the metered valve 522 to the canister 504 and holds both components in place during device 500 use. One series of embodiments of the pump fitment consists of securing interfaces that retain the pump fitment within the actuator body 502, provide vertical displacement, and prevent rotation during installation of the canister 504.

The propellant canister 504 may have a capacity for distributing propellant for a certain number of doses. In one embodiment, the device 500 may be shipped without a canister 504 and the canister 504 may be loaded into the actuator body 502 by the user. In some embodiments, the propellant canister may be replaced with a new propellant canister, such that the device 500 may be reused. In one aspect, when the MDI device is actuated, a discrete amount of pressurized HFA fluid is released. The MDI may contain between about 30 to about 300 actuations, inclusive of endpoints, of HFA propellant. The amount of fluid propellant released upon actuation may be between about 20 microliters (µl) and about 200 µl inclusive of endpoints, of liquid propellant.

The actuator body 502 comprises a propellant channel 524 that is in fluid communication with the propellant canister 504. The propellant channel 524 is in fluid communication with the inlet interface 514, which is configured to couple to the compound container 520 such that propellant released from the propellant canister 504 can be introduced into the compound container 520 via the one or more grooves 528 on the inlet interface 514. In the embodiment of FIG. 5B, the propellant channel 524 includes a port 526 at a distal end for receiving the tip 506. In this configuration, the tip 506 may be coupled and decoupled to the actuator body 502 by inserting the tip 506 into the port 526. In other embodiments, the port 526 may be inserted into the tip 506. In some embodiments, the port 526 and/or the tip 506 may include a sealing interface that creates an airtight seal between the propellant channel 524 and the tip 506 such that propellant released from the canister 504 does not escape out of the propellant channel 524 and is directed to the inlet interface 514.

The tip 506 may be coupled and decoupled to the actuator body 502, which enables a user to load and unload a compound container 520 to and from the inlet interface 514. The tip 506 includes the outer wall 508 and the inner wall 510, where the inner wall forms the exit channel 512 which extends between a proximal end and a distal end of the tip 506. The inlet interface 514 is positioned about a distal end of the outer wall 508, and the inlet interface 514 couples the compound container 520. In the embodiment of FIG. 5B, the inlet interface 514 is a collar that may be inserted into the compound container 520. In other embodiments, the inlet interface 514 may be a ring, band, port, or strap that interfaces with the compound container 520. The inlet interface 514 includes one or more grooves 528 (shown in FIG. 5C) for directing propellant released from the canister 504 into the compound container 520 coupled to the inlet interface 514. The released propellant then contacts the compound within the compound container 520, agitating and entraining the compound and propelling the compound through the exit channel 512 and out the outlet orifice 516 located at a distal end of the exit channel 512. In the embodiment of FIG. 5B, the tip 506 includes a nozzle at the distal end of the exit channel 512 for directing the released propellant and the compound out of the outlet orifice in a narrow plume.

Figure 5C:
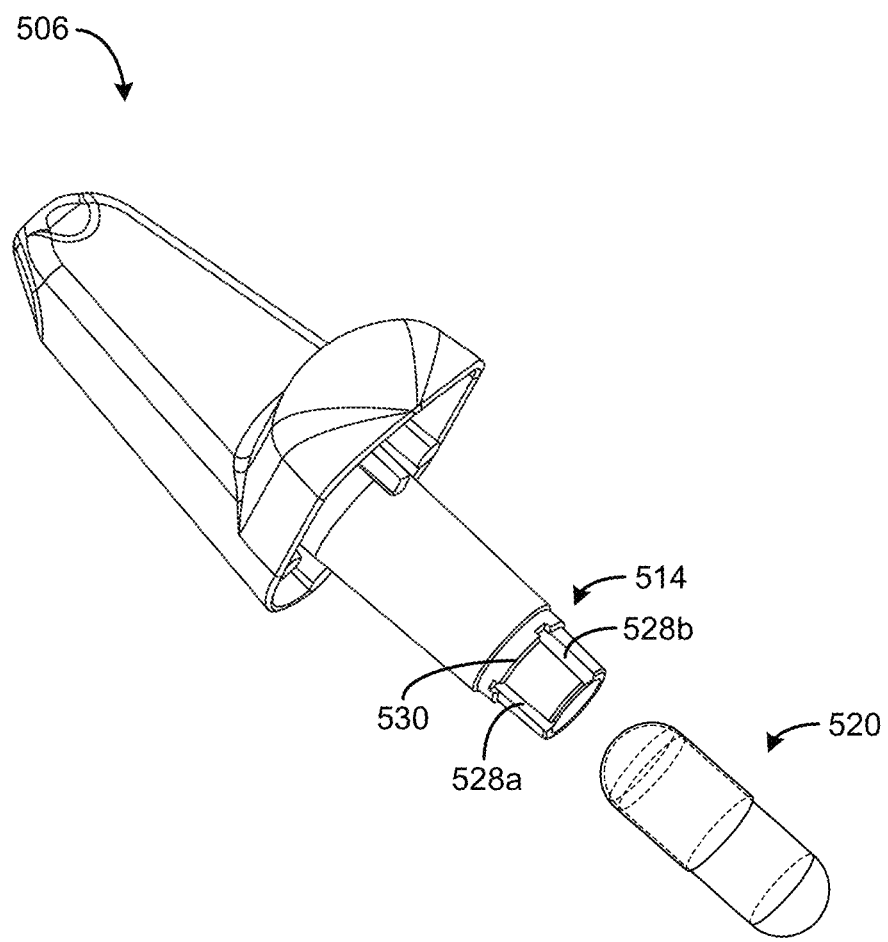
FIG. 5C is a perspective view of a tip and a capsule, in accordance with one or more embodiments.

FIG. 5C is a perspective view of the tip 506 and a compound container, in accordance with one or more embodiments. In the embodiment of FIG. 5C, the compound container 520 is a capsule. The capsule may be comprised of two portions fitted together. When separated, a portion of the capsule (e.g., a half-capsule, as shown in FIGS. 5E-5G) may be coupled to the tip 506. In use, the compound container 520 may contain a compound within the capsule. In one example, the compound is a powder. As shown in FIG. 5E, the half-capsule comprises an exit opening 532 of the compound container 520. The exit opening 532 may be coupled to the inlet interface 514, as shown in FIGS. 5F-5G. In the embodiments of FIGS. 5F-5G, the inlet interface 514 is inserted into the exit opening 532, and the compound container 520 may be secured to the inlet interface 514 via an interference fit. In an alternate embodiment, the exit opening 532 may be inserted into the inlet interface 514. As shown in FIGS. 5G-5H, the tip 506 has the outer wall 508 and the inner wall 510, where the exit channel 512 is formed by a bore or lumen through the inner wall 510. The exit opening 532 is fitted about the inlet interface 514 such that the compound container 520 and the exit channel 512 are in fluid communication.

Figure 5D:
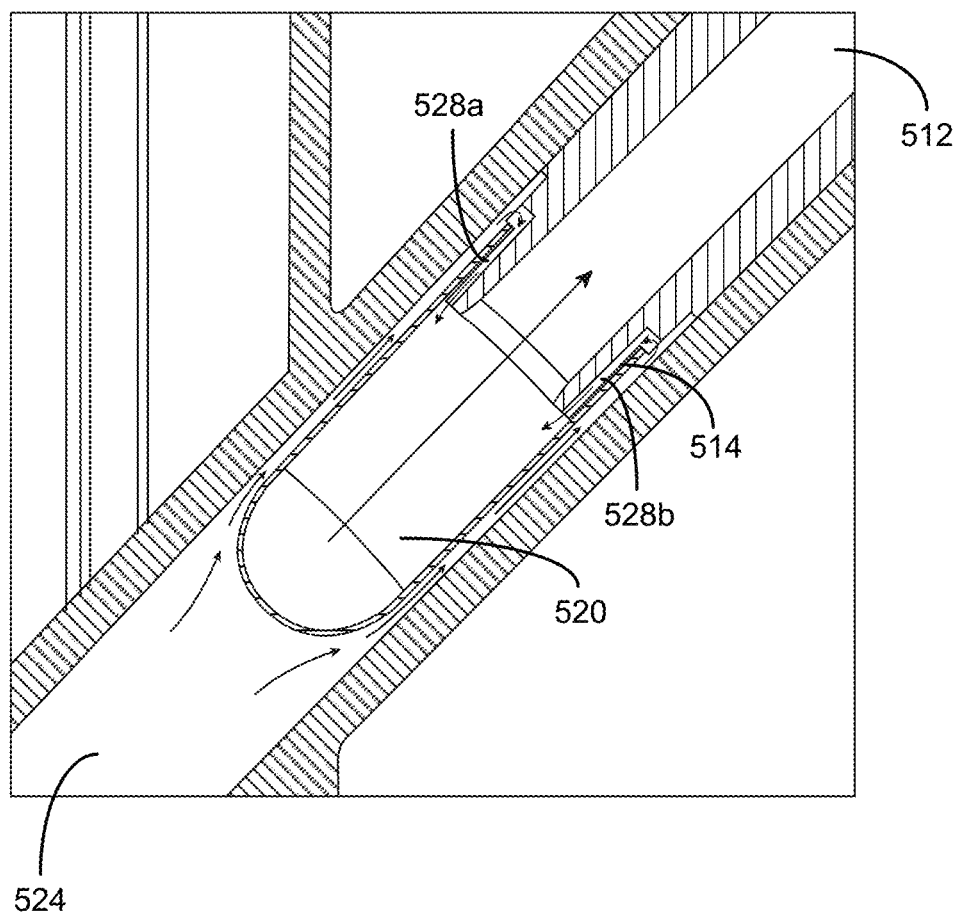
FIG. 5D is a cross-sectional view of the tip and the capsule coupled to the device, in accordance with one or more embodiments.
Figure 5E:
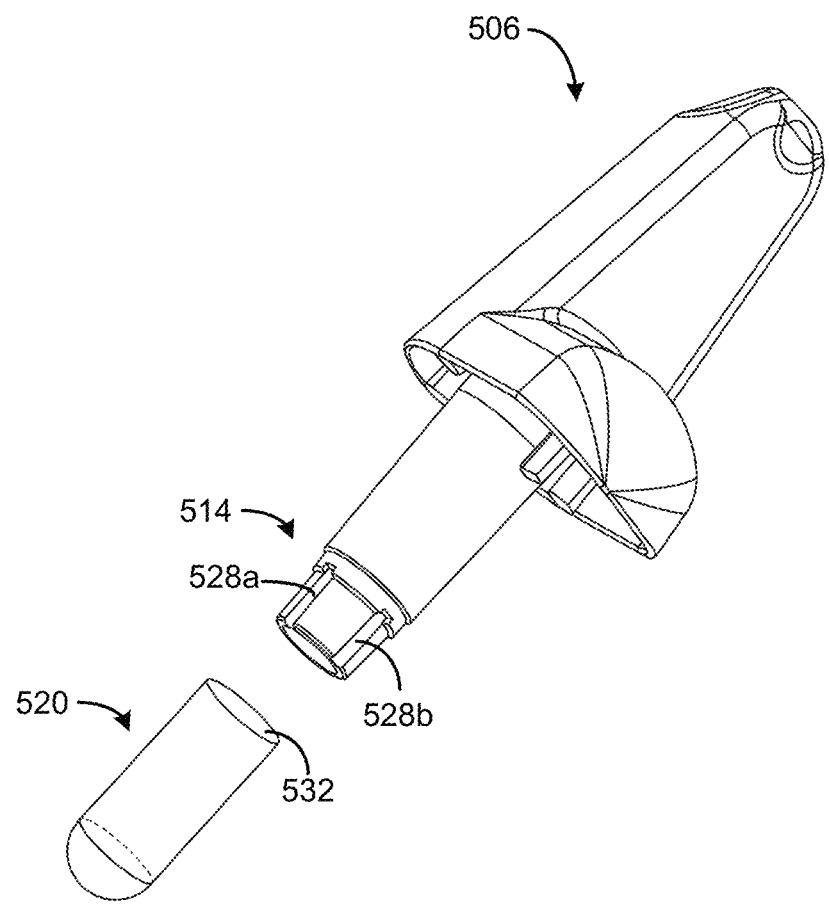
FIG. 5E is an exploded view of the tip and the capsule, in accordance with one or more embodiments.
Figure 5H:
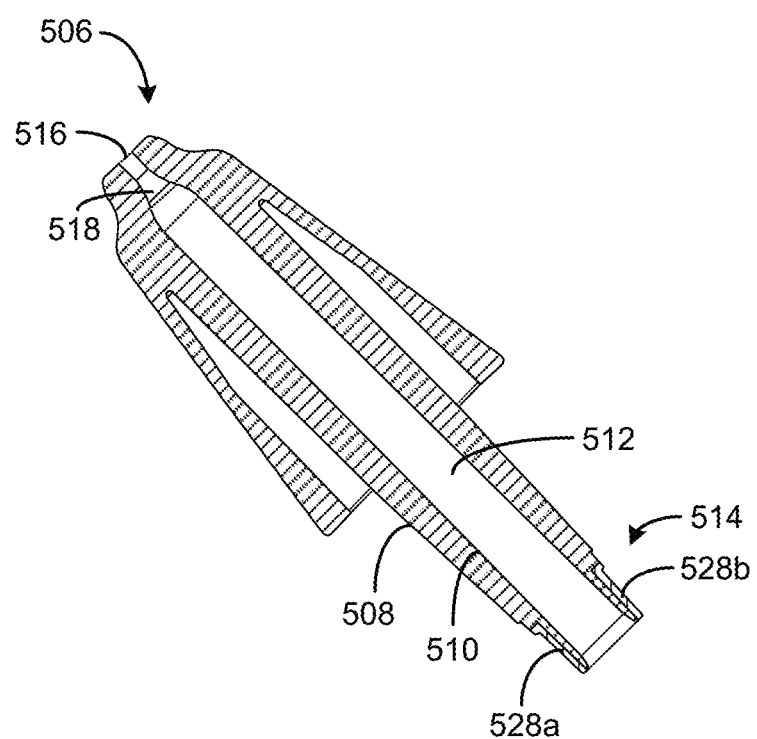
FIG. 5H is a cross-sectional view of the tip, in accordance with one or more embodiments.
Figure 5I:
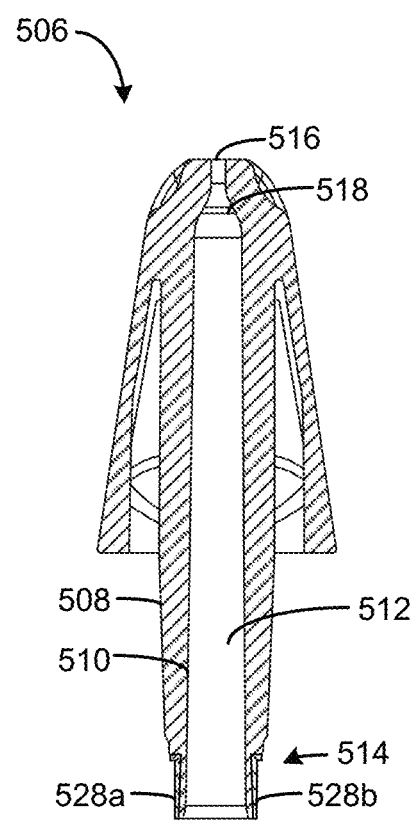
FIG. 5I is a cross-sectional view of the tip, in accordance with one or more embodiments.
Figure 5J:
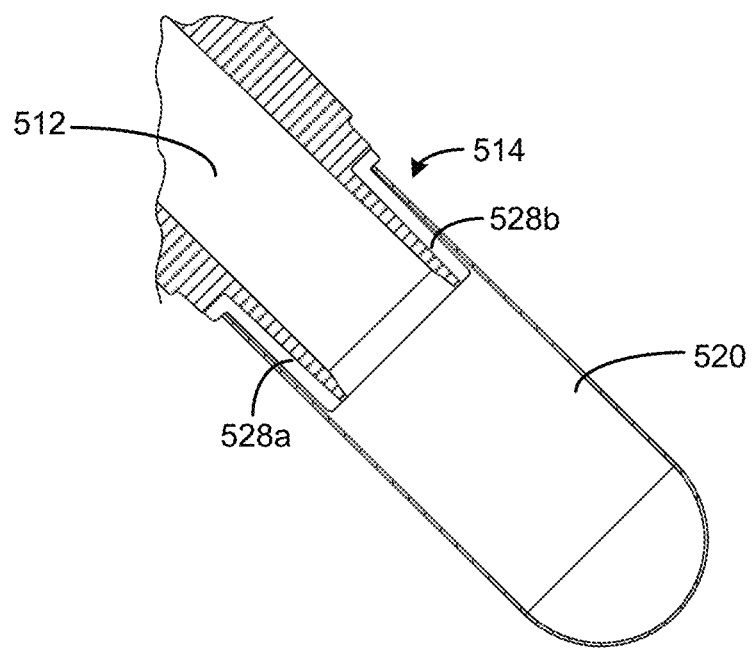
FIG. 5J is a cross-sectional view of an inlet interface of the tip with the capsule attached, in accordance with one or more embodiments.
Figure 5K:
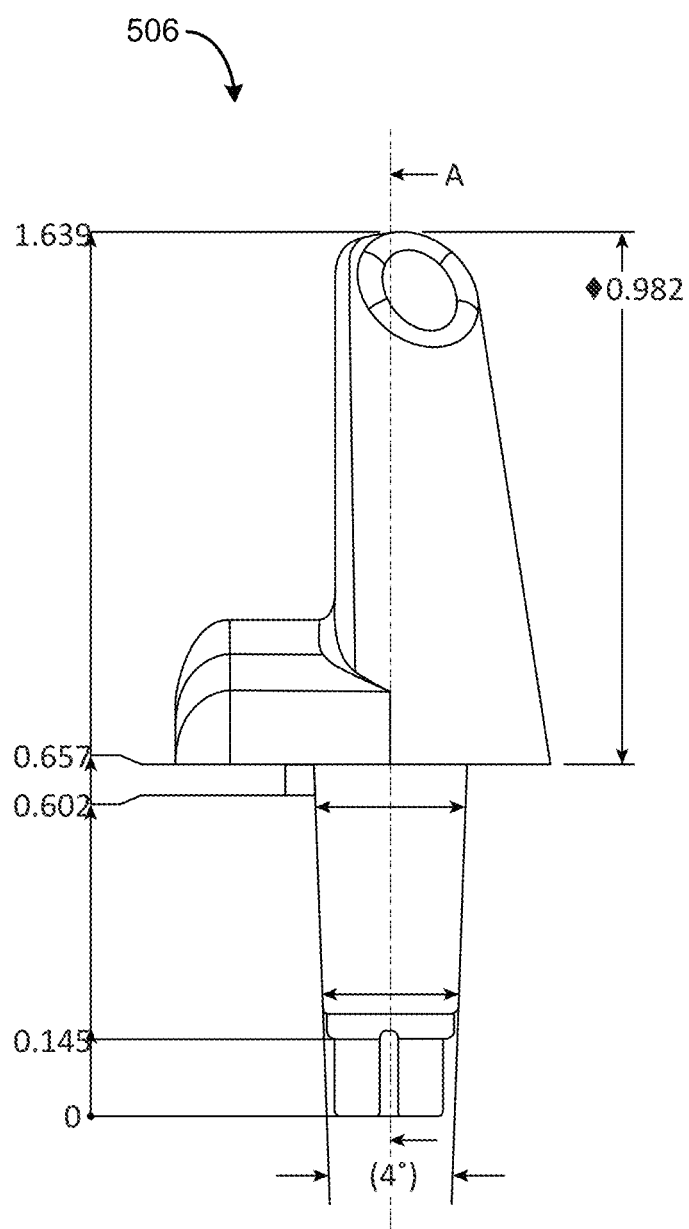
FIGS. 5K-5N are perspective views of the tip of the device, in accordance with one or more embodiments.
Figure 5L:
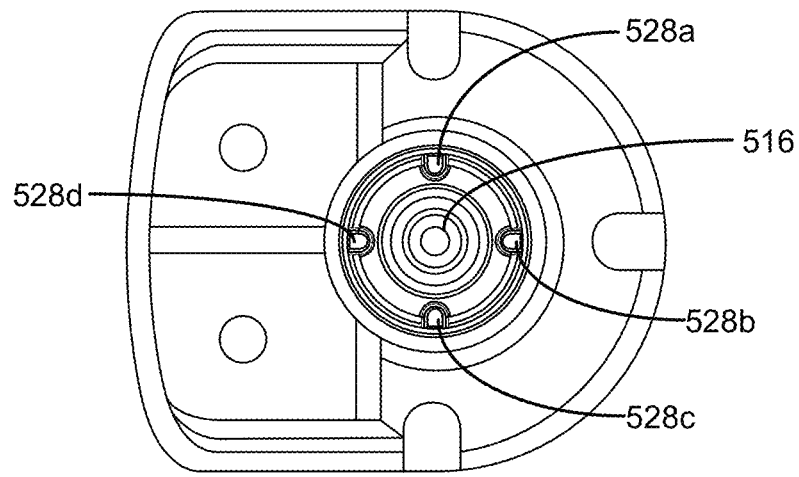
Figure 5M:
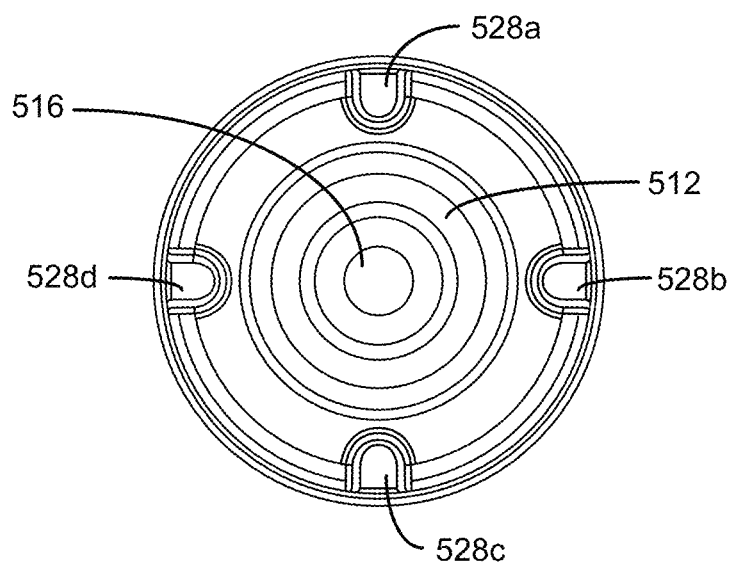
Figure 5N:
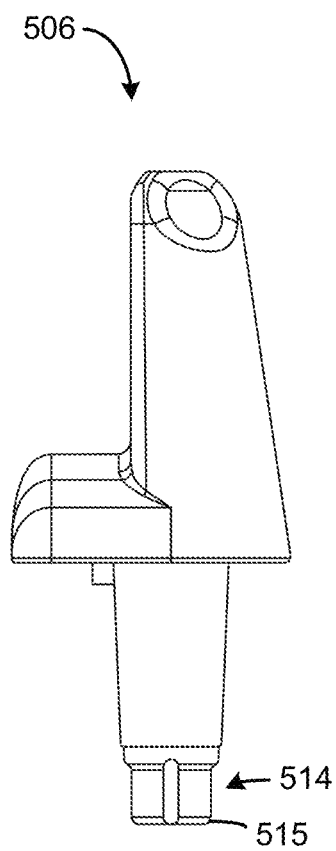
Figure 50:
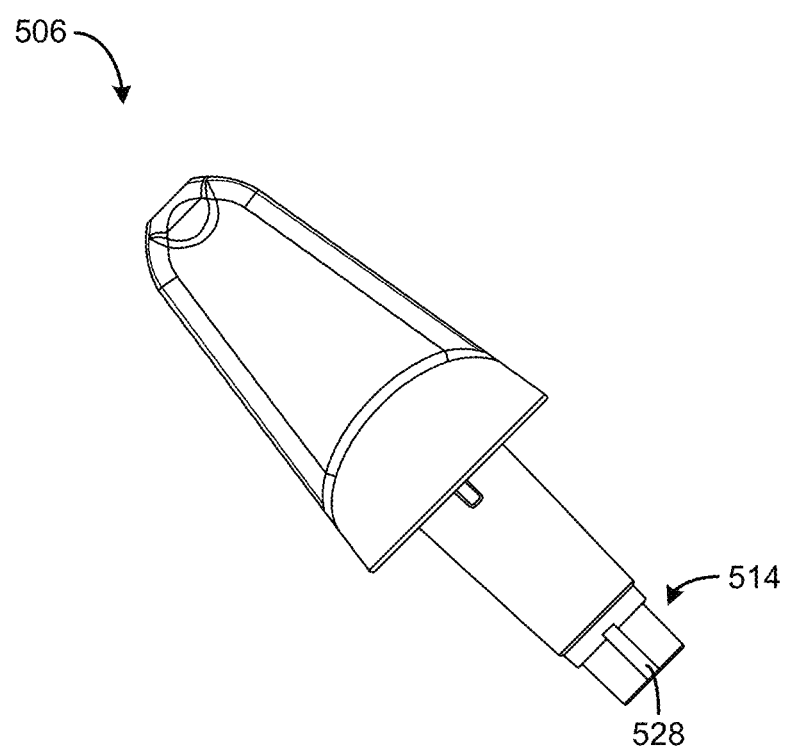

As shown in FIGS. 5F, 5G, and 5J, the inlet interface 514 is, for example, a ring, band, port, collar, or strap interfacing with the compound container 520. As shown in FIGS. 5C, 5E, 5F, 5K, 5L, 5M, 5N, 5O, and 5P, one or more grooves 528 are positioned on the inlet interface 514 and create a flow path for the propellant released from the propellant canister 504 to travel into the compound container 520. An example of the grooves 528 includes but is not limited to channels, slots, radial ports, or passageways. The grooves 528 provide a pathway via the inlet interface 514 by which the propellant flows into the compound container 520. In one example, there are a plurality of grooves 528. The grooves 528 may be equally spaced about the inlet interface 514. The grooves 528 may be of equal size to each other or may be of differing sizes. The grooves 528 run along a length of the inlet interface 514 such that, when the compound container 520 is coupled to the inlet interface 514, a first portion of each groove 528 is exposed within the propellant channel 524 and a second portion of each groove 528 is positioned within the compound container 520. As shown in FIG. 5C, the inlet interface 514 includes a ledge 530 that is designed to abut the compound container 520 when coupled to the inlet interface 514 and the grooves 528 extend past the ledge 530 such that the grooves 528 are not fully covered by the compound container 520.

In use, as shown by the direction of the arrows in FIG. 5D, the propellant released from the canister 504 flows through the propellant channel 524 and into the compound container 520 via the grooves 528. The exit channel 512 is aligned with the exit opening 532 of the compound container 520. The propellant flows in the grooves 528 of the inlet interface 514, into the compound container 520 to agitate the powder, and the powder and the propellant exit the compound container 520 via the exit opening 532 congruent with the exit channel 512. The propellant and powder mixture are carried through the exit channel 512 through the nozzle 518 and exit the device 500 at the outlet orifice 516. In one example, the tip 506 may have one or a plurality of outlet orifices. The plume exiting the outlet orifice 516 has a narrow spray plume.

Figure 5P:
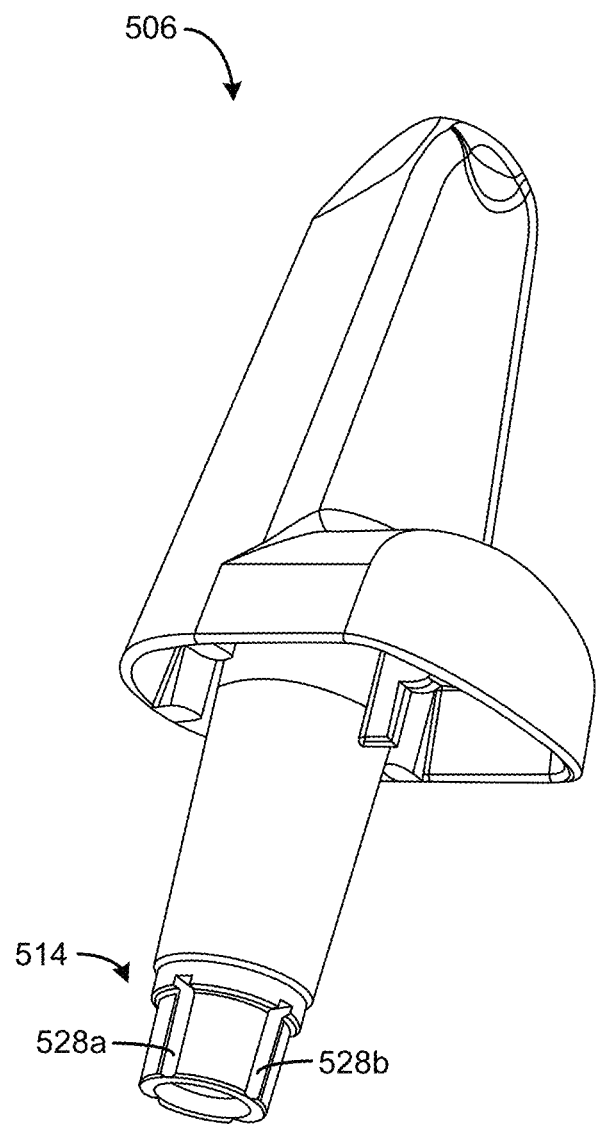
FIG. 5P is a perspective view of the tip, in accordance with one or more embodiments.
Figure 5Q:
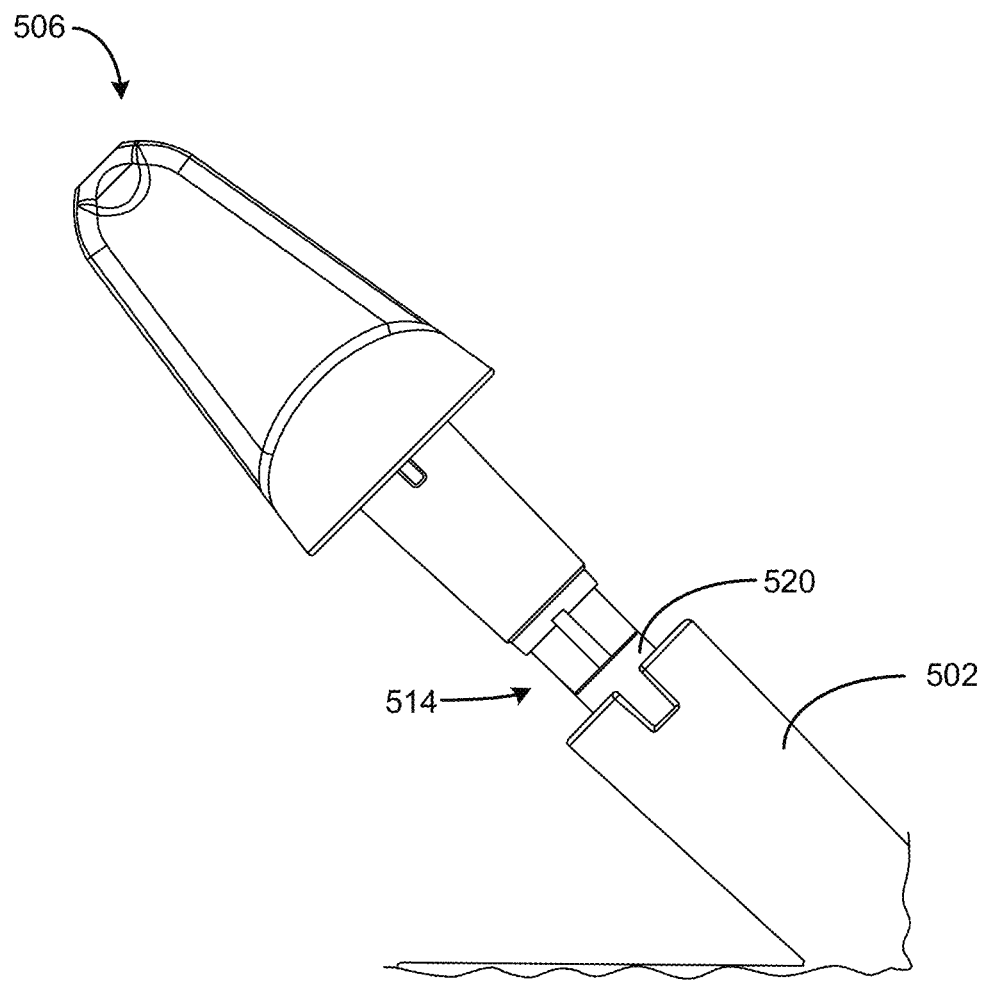
FIG. 5Q is a perspective view of the tip coupled to the device, in accordance with one or more embodiments.
Figure 5R:
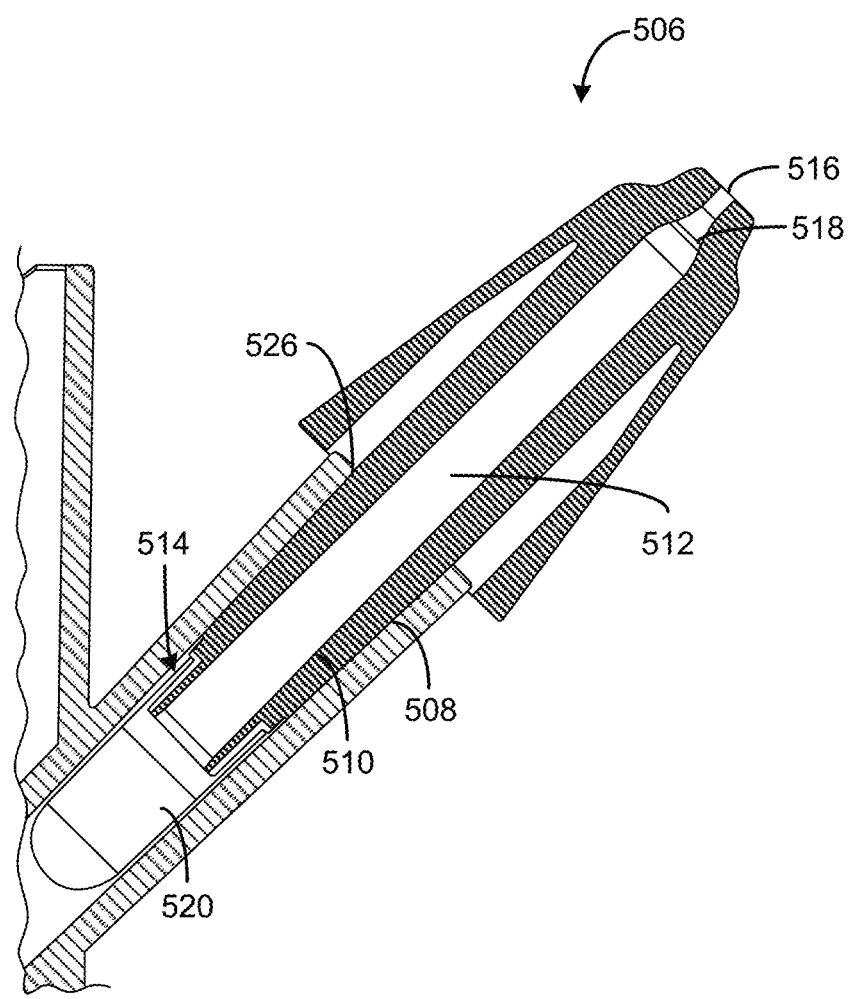
FIG. 5R is a cross-sectional view of the tip coupled to the device, in accordance with one or more embodiments.
Figure 5S:
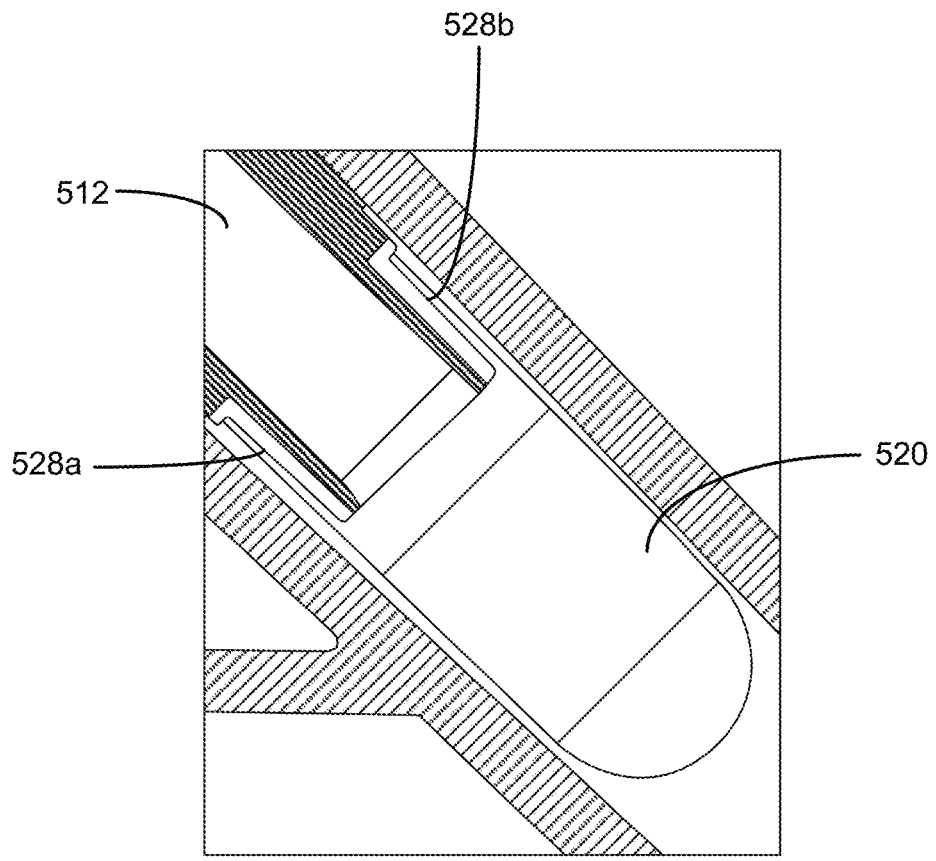
FIG. 5S is a zoomed-in view of the inlet interface with the capsule attached, in accordance with one or more embodiments.
Figure 5T:
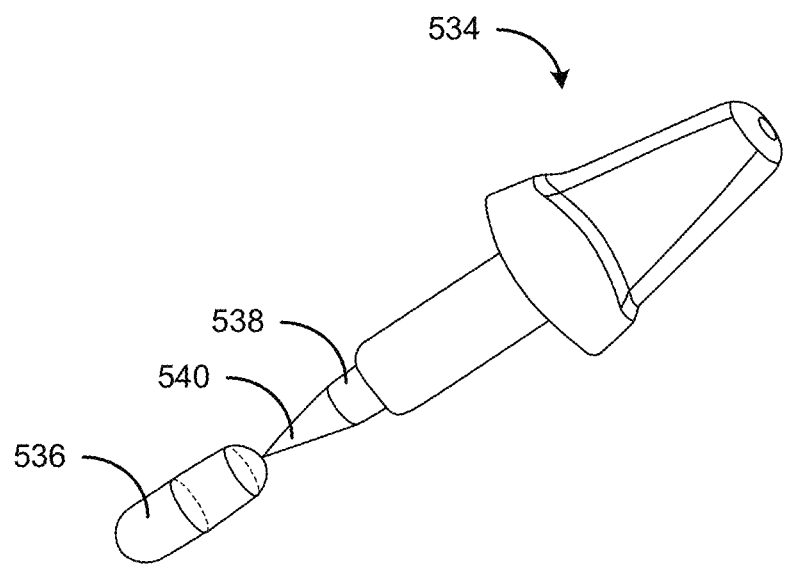
FIG. 5T is a perspective view of a second embodiment of a tip, in accordance with one or more embodiments.

In one example of use of the device 500, at time of use, a user separates a pre-filled capsule into its two halves. In one example, the capsule is prefilled with a powder compound. The half-capsule is coupled to the tip 506 via the inlet interface 514. As shown in FIGS. 5P and 5Q, the tip 506 is then coupled to the actuator body 502. A propelling gas, for example from either a refrigerant or compressed gas source, is directed through the propellant channel 524 and towards the filled powder capsule. The grooves 528 around the inlet interface 514 of the tip 506 introduce high velocity jets of propellant gas which agitate the dry powder into a suspension within the propellant gas (data not shown but confirmed with high speed close up video). Grooves 528 that introduce gas tangentially to the semispherical-shaped bottom of the compound container 520 creates jets which enhance stirring and entrainment of powder. Once the powder has been suspended, it is evacuated through the exit opening 532, into the exit channel 512, and out the outlet orifice 516 of the device 500.

Figure 5U:
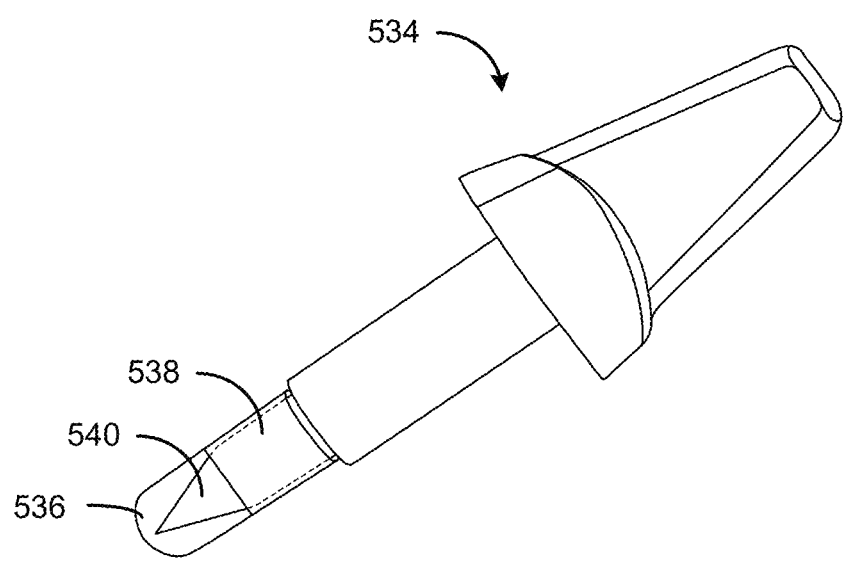
FIG. 5U is a perspective view of the tip of FIG. 5T with a capsule attached, in accordance with one or more embodiments.

Generally, when accelerating a powder formulation through a restricting orifice, any constricting junction will cause the powder to clog. Since the powder administered by this device 500 is suspended within the propellant gas prior to evacuation, it can be further throttled and directed without device clogging. As a result, a much larger mass of powder can be delivered through a much smaller outlet orifice without the device 500 being prohibitively long. The time from propellant actuation to end of compound delivery is less than 1 second.

The grooves 528 in the proximal end of the tip 506 promote gas flow into the compound container 520. In one example, the HFA gas is directed (e.g. orthogonally or near-orthogonally) at the surface of the powder dose residing in the compound container 520, which creates rapid agitation and entrainment of the powder. The semispherical shape of the compound container 520 promotes gas redirection to the exit channel 512 of the tip 506 as shown in FIG. 5D. The arrows of FIGS. 5B and 5D show the direction of propellant flow after the device 500 has been actuated.

The actuator body 502 attached and seals to the propellant canister 504 and the tip 506, creating a pressurized flow path for the propellant gas. In certain aspects, the actuator body 502 is a reusable component. In certain aspects, the canister 504 is a reusable component.

In one example, the compound container 520 is a standard Size 3 drug capsule, although one of skill in the art would know how to use other sized drug capsules and modify the device 500 to fit same. Additionally, in another example, the compound container 520 may not be a capsule, but another container capable of containing a compound, such as but not limited to an ampoule. In one example, the ampoule may be made of plastic, and in one example it may be a blow fill sealed ampoule. To load the device 500, the user or clinician will separate a prefilled formulation containing capsule, discard the cap, and install the capsule over the tip 506. An empty compound container 520 can also be filled by a clinician at time of use before installing the compound container 520 onto the tip 506. In certain examples, the capsule is a disposable component.

The tip 506 receives the compound container 520 during loading and is then coupled to the actuator body 502 prior to use. When the propellant canister 504 is actuated, expanding propellant gas is introduced into the compound container 520 via the grooves 528 around the inlet interface 514 of the tip 506. The resulting propellant gas jets agitate and entrain the powder formulation within the compound container 520, which then exits through the exit channel 512 and the outlet orifice 516 of the tip 506. In one example, the tip 506 is a disposable component. FIG. 5K illustrates example measurements of the tip 506 with units in inches. In the embodiment of FIG. 5N, the inlet interface 514 may include a radius along a bottom edge 222 to aid placement of the compound container 520 onto the tip 506. The radius of curvature may range between approximately 0.005 inches to 0.025 inches, inclusive.

FIGS. 5T and 5U illustrate perspective views of a second embodiment of a tip 534. Similar to the tip 506, the tip 534 may be coupled and decoupled to the actuator body 502, which enables a user to load and unload a compound container 536 to and from the tip 534 for delivery to an upper nasal cavity of a user using the device 500. As shown in FIGS. 5T and 5U, a compound container 536 is a capsule. The compound container 536 may, in one example, contain a powder. In the embodiments of FIGS. 5T and 5U, the tip 534 includes an inlet interface 538 for coupling the compound container 536, where the inlet interface 538 has a puncture member 540. The puncture member 540 is designed to puncture the compound container 536 to create an opening in the compound container 536. The puncture member 540 may comprise a sharp point, a sharp angle, a blade-like edge, or other suitable geometries for puncturing the compound container 536. In one embodiment, the inlet interface 538 includes more than one puncture member 540, where each puncture member 540 is designed to puncture the compound container 536. The puncture members 540 may be positioned about the inlet interface 538 in a pattern, symmetrically, or at random. In one example, in use, a user may remove the tip 534 from the actuator body 502, load the compound container 536 into the port 526 of the propellant channel 524, and then insert the tip 534 back into the port 526. As the tip 534 is coupled to the actuator body 502, the puncture member 540 punctures the capsule. In this configuration, the punctured capsule fits around the puncture member 540, as shown in FIG. 5U. In alternate embodiments illustrated in FIGS. 5V-5X, the puncture member 542 may comprise a plurality of puncture points 544 that each puncture the compound container 536. The plurality of puncture points 544 may be spaced about the puncture member 542.

Figure 5V:
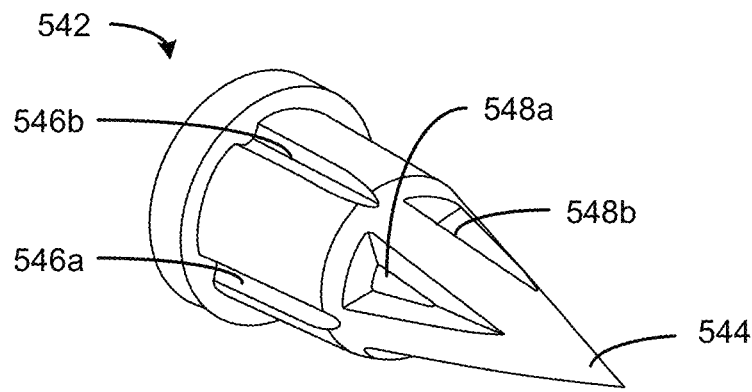
FIG. 5V is a perspective view of a puncture member, in accordance with one or more embodiments.
Figure 5W:
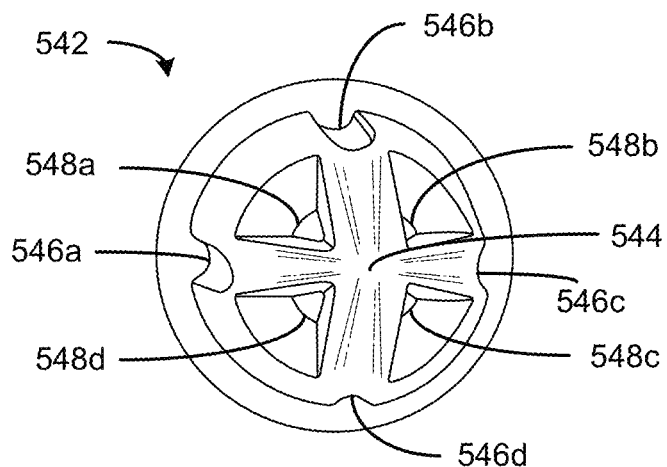
FIG. 5W is a perspective view of the puncture member, in accordance with one or more embodiments.
Figure 5X:
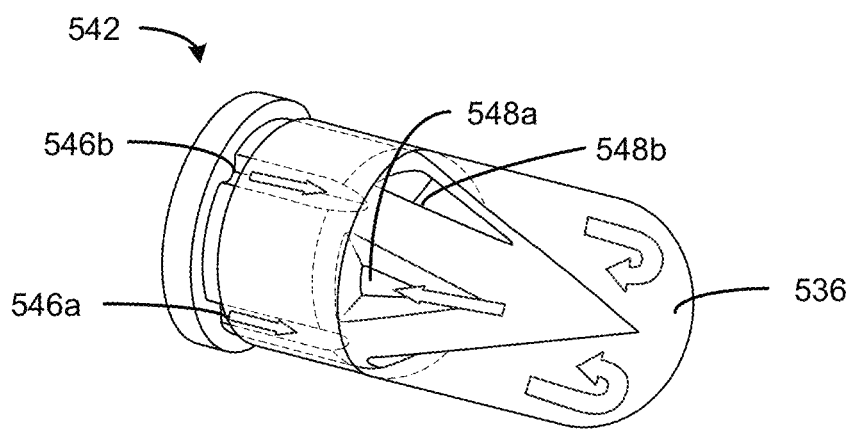
FIG. 5X illustrates a flow path of the second embodiment of the puncture member, in accordance with one or more embodiments.

FIGS. 5V and 5W illustrate perspective views of a puncture member 542 that may be used with the tip 534, in accordance with one or more embodiments. As shown in FIG. 5V, the puncture member 542 may be a collar, ring, band, port or strap that couples with the punctured compound container 536. The puncture member 542 includes one or more puncture grooves 546 that, similar to grooves 528, form a flow path between the propellant channel 524 and the compound container 536. The propellant from the propellant canister 504 enters via the one or more puncture grooves 546 of puncture member 542 and flows along the puncture grooves 546 and into the punctured compound container 536. As shown in FIGS. 5V and 5W, the puncture member 542 includes a plurality of puncture openings 548. In the embodiments of FIGS. 5V, 5W, 5X, the puncture openings 548 are in fluid communication with the exit channel 512. The propellant from the propellant canister 504 flows into the puncture grooves 546, mixes with the powder in the punctured compound container 536, and flows into the puncture openings 544 to the exit channel 512. The arrows of FIG. 5X illustrate the flow path of the propellant. The exit channel 512 provides a route for the propellant and the powder to the nozzle 518 and the outlet orifice 516. The mixture of propellant and powder exit the device 500 via the outlet orifice 516. The plume exiting the device 500 is a narrow spray plume. In this embodiment, the puncture member 542 may be integrally molded as a single piece or may consist of two or more pieces. In one example, the puncture member 542 may be a separately molded piece acting in association with the inlet interface 538 (where the capsule attaches). In some embodiments, an inlet interface may include more than one puncture member 542.

As shown in FIGS. 5V and 5W, as an alternate to the capsule being manually separated prior to placement on the tip 534, the tip 534 may include an integrated puncture member 542 and puncture grooves 546. In order to create a repeatable puncture of the compound container 536, a puncture member 542 comes to a single point, puncture point 544. In one example, the puncture point 544 includes puncture openings 546 that are radially spaced about the puncture point 544. The puncture openings 546 are in fluid communication with the exit channel 512 for the powder to be evacuated from the compound container 536.

As shown in FIG. 5X, by allowing the propellant flow path to be created with an inline puncture motion, loading the compound container 536 onto the tip 534 is simplified for the user, as the compound container 536 does not require manual manipulation and separation. In one example, the puncture member 542 is formed integrally with the tip 534. In one example, the filled compound container 536 may be filled and installed into either the actuator body 502 or the tip 534 during manufacturing of the device 500. At time of use, a user may apply a linear motion to drive the puncture member 542 into the pre-filled compound container 536, creating a complete gas flow path for dosing prior to propellant actuation.

The invention is further described in the following examples, which are not intended to limit the scope of the invention.

Powder Capsule

In one embodiment, a device was constructed and tested. Testing was conducted for residual powder in the compound container after actuation. The device has equivalent performance of powder delivery, as determined by residuals after actuation, when 2 or more but less than 6 grooves on the inlet interface are used. In this example, the grooves are in combination with 63 mg of HFA propellant and a 0.040" outlet orifice of the nozzle. Four grooves (every 90 degrees) were found to provide uniform gas delivery.

Dose Mass

Dose mass reproducibility testing was conducted. The standard deviation on dose delivery shows the device is capable of delivering consistent dose masses. The mean residual of dose left in the device was <5%, showing very little dose is lost in the device.

TABLE A

| Mass reproducibility of final molded device | |
|---|---|
| n | 49 |
| Mean (mg) | 34.9 |
| Standard Deviation (mg) | 1.0 |
| Min (mg) | 32 |
| Max (mg) | 36.7 |
| Range | 4.7 |
| Mean % Residual | 3.8% |

5.4.2.4. Intranasal Device with Plurality of Frits

Figure 7A:
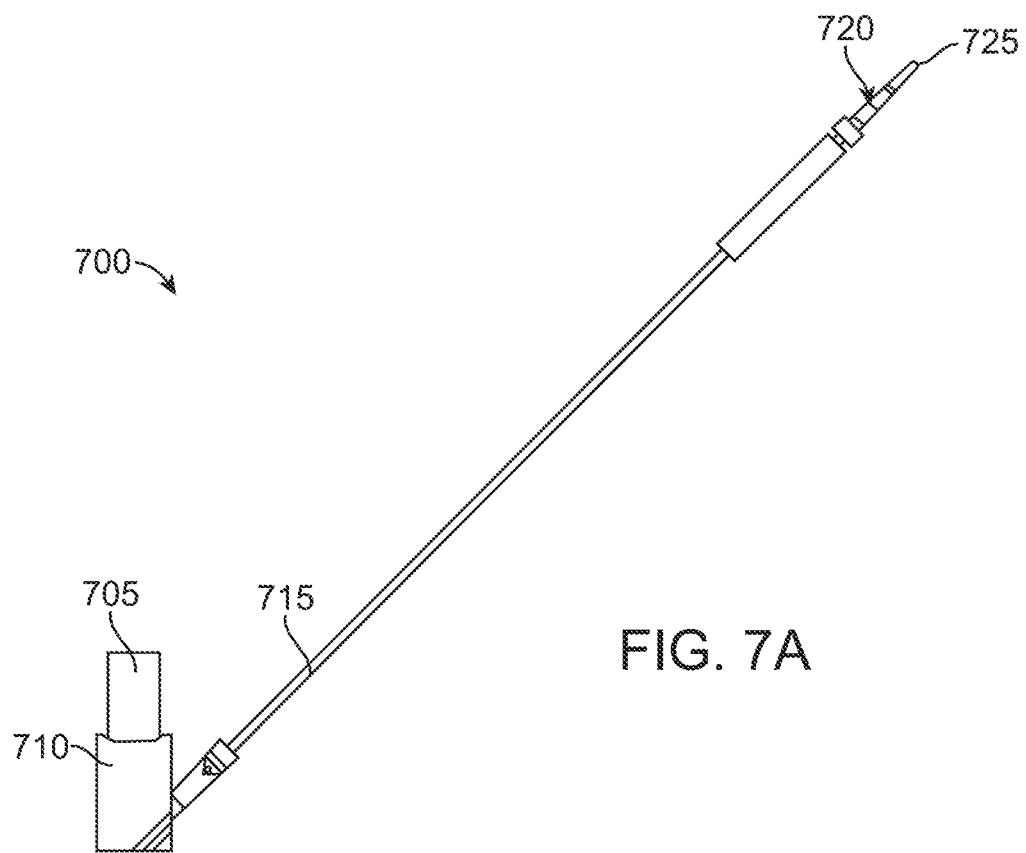
FIG. 7A illustrates another example of a non-human primate precision olfactory delivery device, in accordance with one or more embodiments.
Figure 7B:
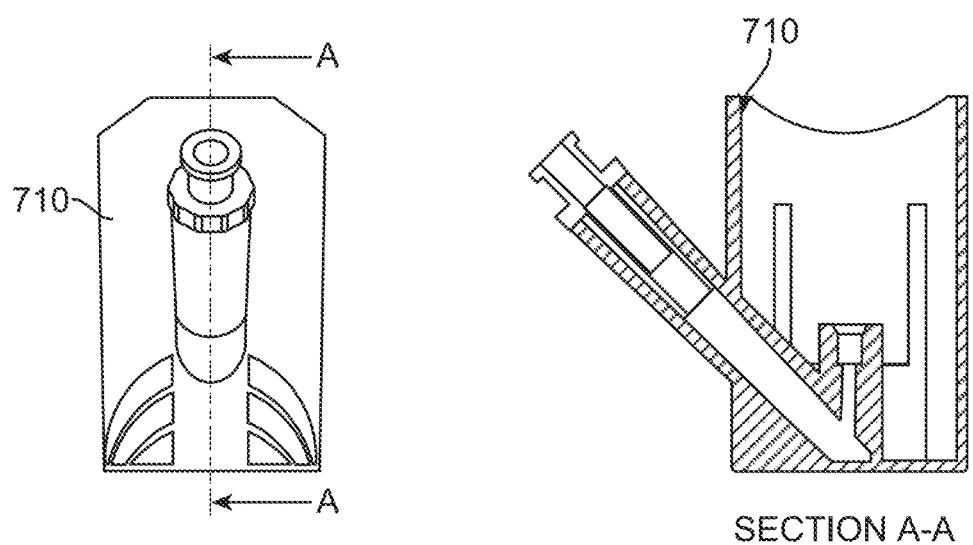
FIG. 7B illustrates a side view and a cross-sectional view of an actuator body of the intranasal device of FIG. 7A, in accordance with one or more embodiments.

FIG. 7A illustrates another example of a non-human primate precision olfactory delivery device 700, and FIG. 7B illustrates a side view and a cross-sectional view of an actuator body 710 of the intranasal device 700 of FIG. 7A. The device 700 may deliver a compound that is a liquid, a powder, or some combination thereof. The device 700 includes a propellant canister 705, the actuator body 710, an extension tube 715, and a tip 720. Similar to the device 1, the propellant canister 705 is in fluid communication with the actuator body 710 such that propellant released from the propellant canister 705 travels through the actuator body 710, through the extension tube 715, through the tip 720, and out an exit opening 725 of the tip 720. A compound may be loaded into the tip 720 such that as the propellant travels through the tip 720, the propellant contacts the compound and propels the compound to the exit opening 725, where the propellant and compound exit as a plume.

FIG. 7C illustrates a side view of the extension tube 715 of the intranasal device 700 of FIG. 7A. The extension tube 715 is a tube comprising an internal channel that creates fluid communication between the actuator body 710 and the tip 720. In the embodiments of FIGS. 7A to 7D, a first end 730 of the extension tube 715 couples to the actuator body 710 and a second end 735 of the extension tube 715 couples to the tip 720 each via a respective connecting interface 740a, 740b (collectively referred to as "740"). The connecting interface 740 comprises a luer lock having a male or a female end on each side of the luer lock. In the embodiment of FIGS. 7A to 7D, each connecting interface 740 comprises a luer lock having two male ends. Accordingly, the male ends of the connecting interface 740a insert into the actuator body 710 and the first end 730, respectively, and the male ends of the connecting interface 740b insert into the tip 720 and the second end 735, respectively. As illustrated in FIG. 7C, the second end 735 may include a plurality of frits 745 positioned within an internal channel of the luer lock. A frit 745 may be configured to convert a liquid propellant into a gas as the propellant passes through the frit 745. Alternatively, the extension tube 715 in FIG. 7B can be configured to convert liquid propellant into a gas. The frit 745 may be composed of porous material. The number of frits 745 may vary in different embodiments. As the number of frits increases, the strength of the plume may be reduced, for example, in terms of its impact force, velocity, plume width, other similar metrics, or some combination thereof. Similarly, the length of the extension tube 715 may be adjusted such that the propellant has a longer or shorter distance to travel through. Calibrating the strength of the plume may enable the device 700 to accurately deliver the compound to the nasal cavity. FIG. 7D illustrates a zoomed-in view of the connecting interface 740*b* at the second end 735 of the extension tube 715 of FIG. 7C—a first example embodiment 750 includes a single frit 745, and a second example embodiment 755 includes three frits 745 stacked in succession. The number of frits 745 may be selected based on the type of compound. For example, a single frit 745 may be used for a powder compound, while three frits 745 may be used for a liquid compound, or vice versa.

FIG. 7E illustrates a side view and a cross-sectional view of the tip 720 of the intranasal device of FIG. 7A. The tip 720 is designed to be inserted into a nasal opening. The tip 720 comprises an internal channel 760 and the exit opening 725 for delivering the compound to the nasal cavity. In the embodiment of FIG. 7E, the tip 720 comprises a frit 745 seated within the internal channel 760. The frit 745 may be configured to convert a liquid propellant into a gas as the propellant passes through the frit 745. The frit 745 may be composed of porous material. In the embodiment of FIG. 7E, tip 720 further comprises a nozzle 765 at a distal end of the tip 720 near the exit opening 725. The nozzle 765 may enhance deposition of the compound within the nasal cavity, such as to the upper olfactory region of a user. In some embodiments, the nozzle 765 may include a single orifice, and, in alternate embodiments, the nozzle 765 may include a plurality of orifices (e.g., between 2 to 11 orifices). In some embodiments, the tip 720 may not include a nozzle. Different embodiments of tips may be used based on different types of compounds to be delivered to the nasal cavity of the user. For example, a tip for delivering a powder compound may not include a nozzle, while a tip for delivering a liquid compound may include a nozzle, or vice versa. In addition, the number of orifices in the nozzle may similarly vary based on the type of compound. A compound may be loaded into the tip 720 such that the compound is contained within the internal channel 760. In the embodiment of FIG. 7E, the compound is loaded into the tip 720 through an opening 770 at a proximal end of the tip 720 before the frit 745 is seated within the internal channel 760. The frit 745 is then inserted to contain the compound inside the tip 720. In an alternate embodiment, for example an embodiment in which the tip 720 does not include a nozzle 765, the compound may be loaded into the tip through the exit opening 725. In the configuration of FIG. 7E, the propellant travels from the propellant canister 705, through the actuator body 710 and extension tube 715, through the tip 720 and contacts the frit 745, and then contacts the compound within the internal channel 760, propelling the compound through the exit opening 725, where the propellant and compound exit as a plume that is delivered within the nasal cavity of the user.

5.4.3. Effective Dose

In the methods described herein, the effective dose is a dose of dry powder composition that comprises olanzapine in an amount effective to reduce agitation. In some embodiments, the effective dose is a dose that comprises olanzapine in an amount effective to reduce agitation within 60 minutes, within 50 minutes, within 40 minutes, within 30 minutes, within 20 minutes, or within 10 minutes.

In some embodiments, the effective dose of dry pharmaceutical composition comprises 1-30 mg, 2-20 mg, 5-15 mg, 5 mg, 6 mg, 7 mg, 8 mg, 9 mg, 10 mg, 11 mg, 12 mg, 13 mg, 14 mg, mg, 19,15 mg, 16 mg, 17 mg, 18 mg, 19 mg, or 20 mg of olanzapine.

In some embodiments, the effective dose is administered as a single undivided dose. In some embodiments, the effective dose is administered as a plurality of equally divided sub-doses.

5.4.4. Patients

In the methods described herein, intranasal administration of olanzapine is used to acutely treat agitated patients. In some embodiments, the patient is an agitated emergency department patient.

In some embodiments, the patient has schizophrenia, bipolar disorder, dementia, or autism. In some embodiments, the patient has bipolar I disorder. In some embodiments, the patient has acute agitation unrelated to schizophrenia, bipolar disorder or autism. In certain embodiments, the patient has refractory panic disorder, post traumatic stress disorder, agitation associated with dementia, agitation related to a drug-induced psychotic state, intoxication, or agitation/aggression coupled with intellectual disability.

5.4.5. PK

In various embodiments of the methods described herein, the intranasal administration provides (a) a mean peak plasma olanzapine concentration ($C_{max}$) of at least 20 ng/mL, with (b) a mean time to $C_{max}$ ($T_{max}$) of olanzapine of less than 1.5 hours.

In some embodiments, the intranasal administration provides a mean peak plasma olanzapine concentration ($C_{max}$) of at least 25 ng/mL, at least 30 ng/mL, at least 40 ng/mL, at least 50 ng/mL, at least 60 ng/mL, at least 70 ng/mL, or at least 80 ng/mL.

In some embodiments, the intranasal administration provides a mean time to $C_{max}$ ($T_{max}$) of olanzapine of less than 1.0 hour, less than 0.75 hour, less than 0.50 hour, or less than 0.25 hour.

In currently preferred embodiments, the intranasal administration provides a mean peak plasma olanzapine concentration of at least 40 ng/mL with a mean time to $C_{max}$ ($T_{max}$) of less than 30 minutes, or more preferably, less than 20 minutes.

5.5. Dry Pharmaceutical Composition

In another aspect, dry pharmaceutical compositions suitable for intranasal administration are provided. The compositions comprise olanzapine and at least one excipient.

In typical embodiments, the dry pharmaceutical composition is a powder.

In some embodiments, the composition comprises olanzapine in a crystalline form. In some embodiments, the composition comprises olanzapine in an amorphous form. In some embodiments, the composition comprises olanzapine in a partially crystalline and partially amorphous form. In particular embodiments, the olanzapine is an amorphous solid obtained by spray-drying. In some embodiments, the composition comprises olanzapine in a crystalline form and an amorphous form.

In typical embodiments, the median diameter of the olanzapine particle size distribution (D50) in the powder, as measured by laser diffraction particle size analyzer, such as the Malvern Panalytical Mastersizer 3000, is 1 µm-500 µm. In some embodiments, the median diameter of the olanzapine particle size distribution (D50) in the powder is 1 µm-250 µm, 1 µm-100 µm, 1 µm-75 µm, 1 µm-50 µm, 1 µm-25 µm, 1 µm-20 µm, 1 µm-15 µm, or 2 µm-15 µm. In certain embodiments, the median diameter of the olanzapine particle size distribution (D50) in the composition is 2 µm-5 µm or 7.5 µm-15 µm.

In various embodiments, the dry pharmaceutical composition comprises no more than 70 wt % olanzapine. In some embodiments, the composition comprises no more than 60 wt % olanzapine. In some embodiments, the composition comprises 10-70% wt % olanzapine, 20-70 wt % olanzapine, 10-60% wt % olanzapine, 20-60 wt % olanzapine, 25-55 wt % olanzapine, 30-50 wt % olanzapine, 30-40 wt % olanzapine or 40-50 wt % olanzapine.

In some embodiments, the pharmaceutical composition further comprises a stabilizer selected from the group consisting of: hydroxypropylmethylcellulose (HPMC), polyvinyl caprolactam-polyvinyl acetate-polyethylene glycol graft co-polymer (Soluplus), vinyl pyrrolinone-vinyl acetate copolymer (Kollidon VA64), polyvinyl pyrrolinone K30 (Kollidon K30), polyvinyl pyrrolidine K90 (Kollidon K90), hydroxypropylcellulose (HPC), hydroxypropyl betacyclodextrin (HPBCD), mannitol, and lactose monohydrate. In some embodiments, the stabilizer is hydroxypropylmethylcellulose (HPMC).

In some embodiments, the dry pharmaceutical composition further comprises a permeation enhancer selected from the group consisting of n-tridecyl-B-D-maltoside, n-dodecyl-β-D-maltoside, 1,2-distearoyl-sn-glycero-3-phosphocholine (DSPC), 1,2-dipalmitoyl-sn-glycero-3-phosphocholine (DPPC), 1,2-dioleoyl-sn-glycero-3-phosphocholine (DOPC), propylene glycol, disodium EDTA, PEG400 monostearate, polysorbate 80, and macrogol (15) hydroxystearate. In some embodiments, the permeation enhancer is 1,2-distearoyl-sn-glycero-3-phosphocholine (DSPC).

In some embodiments, the dry pharmaceutical composition comprises both HPMC and DSPC.

In various embodiments, the dry pharmaceutical composition further comprises a nonionic surfactant. In certain embodiments, the nonionic surfactant is an alkyl maltoside. In particular embodiments, the alkyl maltoside is n-dodecyl β-D-maltoside. In some embodiments, the nonionic surfactant is present in the dry powder composition at 0.1-10 wt %, more typically 1-5 wt %. In particular embodiments, the nonionic surfactant is present at 1 wt %. In some embodiments, the nonionic surfactant is Pluronic PF68. In some embodiments, the nonionic surfactant is present in the dry powder composition at 20-40 wt %, more typically 25-35 wt %. In particular embodiments, the nonionic surfactant is present at 31 wt %.

In some embodiments, the pharmaceutical composition further comprises an antioxidant selected from the group consisting of alpha tocopherol, ascorbic acid, ascorbyl palmitate, bronopol butylated hydroxyanisole (BHA), butylated hydroxytoluene (BHT), citric acid monohydrate, sodium ascorbate, ethylene diainetetraacetic acid, fumaric acid, malic acid, methionine, propionic acid, sodium metabisulfite, sodium sulfite, sodium thiosulfate, thymol, and vitamin E polyethylene glycol succinate.

In some embodiments, the dry pharmaceutical composition further comprises an acid. In certain embodiments, the acid is citric acid. In some embodiments, the acid is present in the dry powder composition at 10-20 wt %, more typically 15-20 wt %. In particular embodiments, citric acid is present at 18 wt %.

In various embodiments, the dry pharmaceutical composition further comprises a salt of a monovalent inorganic cation. Typically, the salt is NaCl. In some embodiments, the composition comprises 1-5 wt % NaCl, or 2-4 wt % NaCl.

In some embodiments, the dry pharmaceutical composition further comprises less than 3 wt %, less than 2.5 wt %, less than 2 wt %, less than 1.5 wt %, less than 1 wt %, less than 0.9 wt %, less than 0.8 wt %, less than 0.7 wt %, less than 0.6 wt %, or less than 0.5 wt % water.

In currently preferred embodiments, the dry pharmaceutical composition comprises 50 wt % olanzapine, 42 wt % HPMC, and 8% DSPC. In some embodiments, the dry pharmaceutical composition is a spray dried composition that comprises amorophous olanzapine. In some embodiments, olanzapine is spray dried in the presence of HPMC and/or DSPC. In other embodiments, HPMC and/or DSPC is added after spray drying of olanzapine.

5.6. Unit Dosage Form

In another aspect, unit dosage forms are provided. The unit dosage form contains a dry pharmaceutical composition as described in Section 5.5 above.

In typical embodiments, the unit dosage form contains 1-30 mg of olanzapine. In some embodiments, the unit dosage form contains 2-20 mg of olanzapine. In some embodiments, the unit dosage form contains 5-15 mg of olanzapine. In some embodiments, the unit dosage form contains 5 mg of olanzapine. In some embodiments, the unit dosage form contains 10 mg of olanzapine. In some embodiments, the unit dosage form contains 15 mg of olanzapine.

In some embodiments, the unit dosage form is a capsule that encapsulates the dry pharmaceutical composition. In some embodiments, the capsule is a hard capsule. In some embodiments, the hard capsule is an HPMC hard capsule.

In some embodiments, the unit dosage form is a dose container that stores the dry pharmaceutical composition, wherein the dose container is configured to removably couple to an intranasal delivery device. In particular embodiments, the dose container is a tip that is configured to be removably coupled to an intranasal delivery device.

5.7. Experimental Examples

The invention is further described through reference to the following experimental examples. These examples are provided for purposes of illustration only, and are not intended to be limiting.

5.7.1. Example 1: Non-Human Primate PK Studies

A single dose pharmacokinetics (PK) study in the cynomolgus monkey was performed to examine the PK following administration of multiple powder olanzapine formulations delivered by the intranasal route using a non-human primate precision olfactory delivery ("nhpPOD") Device. The formulations examined included an unmodified crystalline powder of olanzapine ("API"), a formulation containing hydroxypropylmethylcellulose ("HPMC") and 1,2-distearoyl-sn-glycero-3-phosphocholine ("DSPC"), and a formulation containing HPMC and Pluronic F68. The placebo control, also delivered intranasally by the nhpPOD Device, was microcrystalline cellulose ("MCC").

5.7.1.1. Study Design

The study design of the non-human primate PK study is outlined below:

TABLE 1

| Group | Test Article | Number of Animals (Male/Female) | Dose Route | Dose Level | Administration | Collection Medium and Intervals |
|---|---|---|---|---|---|---|
| 1 | Control[A] | 1/1 | IN[B] | 4 mg | 4 mg dose to right naris | Blood[C] |
| 2 | Intramuscular (IM) | | IM | 0.5 mg/kg | 0.5 mg/kg | Blood[C] |
| 3 | Olanzapine API (Cipla) | 2/2 | IN[B] | 2 mg | 2 mg (API) dose to right naris | Blood[C] |
| 4 | Olanzapine:HPMC:DSPC (50:42:8) | 2/2 | IN[B] | 2 mg[D] | 2 mg (API) dose to right naris | Blood[C] |
| 5 | Olanzapine:PF68:HPMC (50:31:19) | 2/2 | IN[B] | 2 mg[D] | 2 mg (API) dose to right naris | Blood[C] |

[A]MCC (Hetween) 102 Microcrystalline Cellulose
[B]Intranasal (IN) administration using the powder nhpPOD Device.
[C]Blood samples collected at pre-dose (0), 0.05, 0.117, 0.25, 0.5, 0.75, 1, 1.5, 2, 4, 6, 10, 18, 24, 36 hours post dose.
[D]2 mg of olanzapine API was dosed with 2 mg excipient mixture for a total powder dose of 4 mg to the right naris.

Dose Selection

The IM dose in non-human primates ("NHP") was calculated in mg/kg using a 10 mg human equivalent dose (FDA allometric scaling guidance). The monkey intranasal doses were selected based on comparison to a 10-15 mg olanzapine dose to humans using nasal surface area calculations.

Sample Collection

Blood samples were collected, centrifuged to isolate plasma, and were frozen until analysis by LC/MS/MS to measure olanzapine and n-desmethyl olanzapine levels.

Sample Preparation and LC/MS/MS Analysis

Control matrix used included 0.25 Percent Ascorbic Acid fortified plasma. Additionally, BAM.0501 procedures assume that all unknown samples are fortified prior to receipt and assay. AIT Bioscience Bioanalytical Method BAM.0501.01 was used for the quantitation of olanzapine and N-desmethyl olanzapine in K2EDTA monkey plasma. This method was developed to cover the range of 0.0500-50.0 ng/mL of olanzapine and N-desmethyl olanzapine using olanzapine-D8 and N-desmethyl olanzapine-D8 as the respective internal standards. Two sets of calibration standards were included in each analytical run, one set placed at the beginning and one at the end.

Samples were maintained cold until the point of aliquoting. A sample volume of 100 was aliquoted directly to a Waters, Ostro 96-well solid support plate. Then, 300 µL of internal standard solution (1 ng/mL for each ISTD) prepared in 100:1, acetonitrile:formic acid was added to the plate. The wells were mixed well to induce protein precipitation. Then, samples were passed through the bed with the eluate collected into a clean 96-well plate. Samples were then evaporated to dryness under nitrogen at 25° C. and reconstituted in 100 µL of 87.5:10:2.5, water:acetonitrile:ammonium acetate (200 mM, pH 4.0).

Samples were analyzed on a Dionex UltiMate 3000 liquid chromatograph interfaced with a Thermo Scientific TSQ Quantiva triple quadrupole mass spectrometer with ESI ionization. Each extracted sample was injected (10 µL) onto a Waters BEH C18 column (2.1×50 mm; 1.7 µm) equilibrated at 40° C.

Mobile Phase A was 97.5:2.5 water:ammonium acetate (200 mM, pH 4.0).

Mobile Phase B was 97.5:2.5 acetonitrile:ammonium acetate (200 mM, pH 4.0). The LC gradient is shown below:

TABLE 2

| Time (min) | Flow Rate (mL/min) | % MP A | % MP B |
|---|---|---|---|
| 0.00 | 0.500 | 90.0 | 10.0 |
| 0.20 | 0.500 | 90.0 | 10.0 |
| 1.50 | 0.500 | 60.0 | 40.0 |
| 2.50 | 0.500 | 60.0 | 40.0 |
| 2.75 | 0.500 | 90.0 | 10.0 |
| 3.00 | 0.500 | 90.0 | 10.0 |

The retention time, mass transition and precursor charge state for each compound are as follows:

TABLE 3

| Compound | Expected Retention Time (min) | Precursor Exact Mass/Charge (m/z) | Product Observed Mass/Charge (m/z) | Charge State of Precursor Ion |
|---|---|---|---|---|
| Olanzapine | 1.3 | 313.149 | 256.09 | +1 |
| Olanzapine-D8 | 1.3 | 321.199 | 261.10 | +1 |
| N-Desmethyl Olanzapine | 1.1 | 299.133 | 255.89 | +1 |
| N-Desmethyl Olanzapine-D8 | 1.1 | 307.183 | 261.12 | +1 |

Raw data from the mass spectrometer was acquired and processed in Thermo Scientific LCquan. Peak area ratios from the calibration standard responses were regressed using a (1/concentration2) linear fit for olanzapine and N-desmethyl olanzapine. The regression model was chosen based upon the behavior of the analyte(s) across the concentration range used during development.

5.7.1.2. Results

The total doses of olanzapine achieved as well as the dose per cm² of nasal surface area in each group are displayed in the table below:

TABLE 4

| nhpPOD Dose Group (N = 4/group) | Dosing | Body Weight (Avg ± SD, kg) | Avg Dose (mg/kg) | Nasal Surface Area (Avg, cm²) | Avg Dose (mg/cm²) |
|---|---|---|---|---|---|
| Olanzapine for injection 0.5 mg/kg, lyophilized powder for solution | IM | 4.1 ± 0.3 | 0.50 | — | — |
| Cipla API, GMP 2 mg OLZ, Crystalline | One spray, one naris | 4.1 ± 0.4 | 0.49 | 36.0 | 0.06 |
| Spray dried OLZ:HPMC:DSPC 2 mg OLZ, Amorphous | One spray, one naris | 3.9 ± 0.3 | 0.51 | 35.1 | 0.06 |
| Spray dried OLZ:HPMC:PLURONIC F68 2 mg OLZ, Crystalline | One spray, one naris | 4.3 ± 0.5 | 0.47 | 36.9 | 0.05 |

Figure 1:
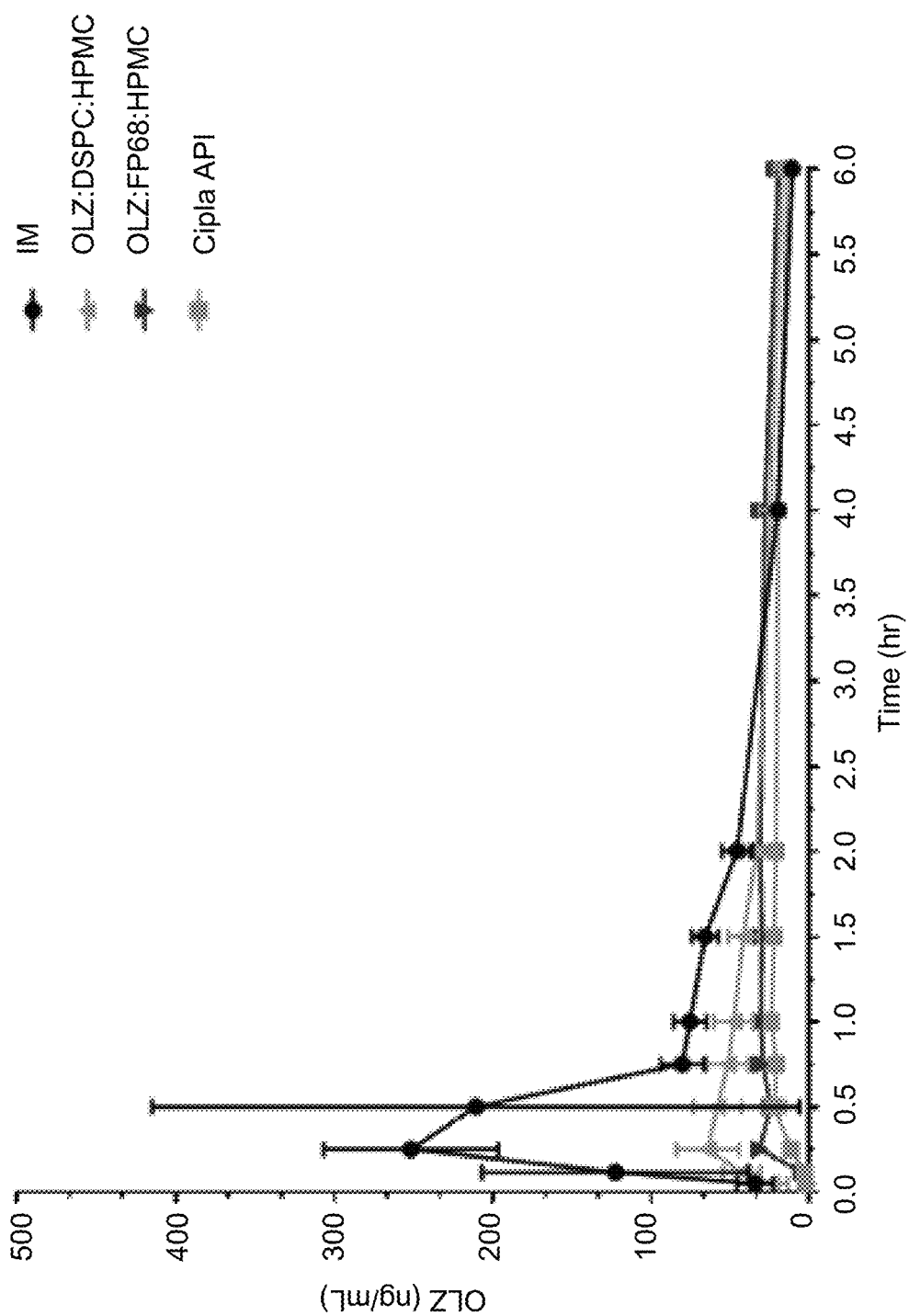
FIG. 1 shows mean plasma levels of olanzapine in non-human primates (NHPs) as a function of time after intramuscular administration (IM) or after intranasal administration of thee different dry powder formulations of olanzapine using a Precision Olfactory Delivery (POD®) Device.

The calculated mean PK parameters for olanzapine are tabulated below in Table 5, and the average plasma concentration-time curves are provided in FIG. 1. For this document, only the olanzapine PK is reported (not the n-desmethyl olanzapine).

TABLE 5

| Dose Group | Route | AUC$_{last}$ (ng * hr/mL) | C$_{max}$ (ng/mL) | T$_{max}$ (hr) | t$_{1/2}$ (hr) |
|---|---|---|---|---|---|
| Olanzapine for injection 0.5 mg/kg, lyophilized powder for solution | IM | 371 ± 55 | 338 ± 121 | 0.31 ± 0.13 | 3.7 ± 0.5 |
| Cipla API, GMP 2 mg OLZ, Crystalline | One spray, one naris | 206 ± 23 | 26.4 ± 4.4 | 0.88 ± 0.25 | 4.7 ± 0.6 |
| Spray dried OLZ:HPMC:DSPC 2 mg OLZ, Amorphous | One spray, one naris | 352 ± 89 | 64.6 ± 18.8 | 0.31 ± 0.13 | 5.0 ± 1.0 |
| Spray dried OLZ:HPMC:PLURONIC F68 2 mg OLZ, Crystalline | One spray, one naris | 285 ± 65 | 35.0 ± 4.9 | 0.81 ± 0.83 | 4.3 ± 0.4 |

The PK results show that intranasal delivery using the nhpPOD Device of a formulation of olanzapine containing HPMC and DSPC results in similar plasma exposure (AUC) and T$_{max}$ as the IM administered olanzapine. In comparison to unformulated olanzapine (Cipla API), the formulated (HPMC/DSPC) powder results in a 1.7-fold higher AUC and a 2.8-fold shorter T$_{max}$.

5.7.2. Example 2: Rodent and Non-Human Primate PK Studies

5.7.2.1. Manufacturing and Analytical Testing

Approximately thirty different olanzapine (OLN) formulations were designed and manufactured for upper nasal delivery by a POD device.

Stabilizers, permeation enhancers, antioxidants, particle size and manufacturing processes were also screened as part of the formulation development process. Specifically, stabilizers tested in the experiment include hydroxypropylmethylcellulose (HPMC), polyvinyl caprolactam-polyvinyl acetate-polyethylene glycol graft co-polymer (Soluplus), vinyl pyrrolidine-vinyl acetate copolymer (Kollidon VA64), polyvinyl pyrrolidine K30 (Kollidon K30), polyvinyl pyrolidone K90 (Kollidon K90), hydroxypropylcellulose (HPC), hydroxypropyl betacyclodextrin (HPBCD), mannitol, and lactose monohydrate. Permeation enhancers tested in the experiment include n-tridecyl-β-D-maltoside, n-dodecyl-β-D-maltoside, 1,2-distearoyl-sn-glycero-3-phosphocholine (DSPC), 1,2-dipalmitoyl-sn-glycero-3-phosphocholine (DPPC), 1,2-dioleoyl-sn-glycero-3-phosphocholine (DOPC), propylene glycol, disodium EDTA, PEG400 mo- nostearate, polysorbate 80, and macrogol (15) hydroxystearate. Antioxidants tested in the experiment include alpha tocopherol, ascorbic acid, ascorbyl palmitate, bronopol butylated hydroxyanisole (BHA), butylated hydroxytoluene (BHT), citric acid monohydrate, sodium ascorbate, ethylene diainetetraacetic acid, fumaric acid, malic acid, methionine, propionic acid, sodium metabisulfite, sodium sulfite, sodiumthiosulfate, thymol, and vitamin E polyethylene glycol succinate.

The formulations were tested, characterized and optimized for POD device compatibility. The formulations were analyzed by an Impel-developed high pressure liquid chromatography/diode array detector method optimized for Impel's OLZ formulations. Their solid states were further characterized by X-ray diffraction (XRD) and differential scanning calorimetry (DSC). Moisture content was measured by Karl Fischer titration or loss on drying. Particle size distribution was measured by laser diffraction (Malvern Panalytical). POD device compatibility for species-specific (rat-POD and NHP-POD (FIG. 2)), clinical, and to-be-marketed devices was also tested using a gravimetric method that determines compatibility through residual and variability in delivery (coefficient of variation).

In total, twenty of the formulations were evaluated in single dose PK studies in rat (data not shown) and non-human primates (see below). The twenty formulations include six lead formulations (F-OLZ #1-6), the compositions of which are provided in Table 6 below.

TABLE 6

| Code | Formulation Description | Manufacturing process | Assay % | XRPD (no unit) | Tg (° C.) | Water content (% w/w) | D10 (μm) | D50 (μm) | D90 (μm) |
|---|---|---|---|---|---|---|---|---|---|
| F-OLZ #1 | Cipla API | Not applicable | 99.8 | Crystalline | | 0.29 | | 2.1 | 25 |
| F-OLZ #2 | OLZ:HPMC:DSPC (50:42:8 w/w) | Hot process n-propanol | 99.8 | Amorphous | 59 | 0.38 | | | |
| | | Hot process, 90:10 (1-propanol:water). Required secondary drying. 1% feedstock. 650 ppm residual solvent | | Amorphous | 57.5 | | 4.5 | 11.2 | 21.8 |
| | | Hot process, 90:10 (1-propanol:water). Required secondary drying. | 98.4 | Amorphous (absence of crystallinity peaks) | 67.24 | 0.89 | 4.05 | 13.2 | 24.0 |
| F-OLZ #3 | OLZ:HPMC:PLURONIC F68 (50:19:31 w/w) | Homogenized suspension | 100.5 | Crystalline | 52 | 0.14 | 4.7 | 9.5 | 19.7 |
| F-OLZ #4 | OLZ:HPMC:DSPC:Citric Acid (41:34.5:6.5:18 w/w) | Water and citric acid to enable full dissolution | 94.9 | Mostly amorphous (DSPC peaks) | 75 | ND | | | |
| F-OLZ #5 | OLZ:HPMC:DSPC (30:62:8 w/w) | Hot process, 90:10 (1-propanol:water) | 96.1 | Amorphous | 58.13 | ND | | | |
| F-OLZ #6 | OLZ:HPMC:DSPC: Maltoside (50:41:8:1 w/w) | Hot process, 90:10 (1-propanol:water) | Not determined | Amorphous | 58.69 | ND | | | |

5.7.2.2. Study Design

The formulations were evaluated at a single dose in rats (data not shown) and in NHP. The study design of the NHP PK study for six lead formulations (F-OLZ #1-6) is outlined below:

TABLE 7 [D]

| Group | Test Article | Number of Animals (Male/ Female) | Dose Route | Dose Level | Administration | Collection Medium and Intervals |
|---|---|---|---|---|---|---|
| F-OLZ #1 | Cipla API | 2/2 | IN[A] | 2 mg[C] | 2 mg (API) dose to right naris | Blood[B] |
| F-OLZ #2 | OLZ:HPMC:DSPC (50:42:8 w/w) | 2/2 | IN[A] | 2 mg[C] | 2 mg (API) dose to right naris | Blood[B] |
| F-OLZ #3 | OLZ:HPMC:PLURONIC F68 (50:19:31 w/w) | 2/2 | IN[A] | 2 mg[C] | 2 mg (API) dose to right naris | Blood[B] |
| F-OLZ #4 | OLZ:HPMC:DSPC:Citric Acid (41:34.5:6.5:18 w/w) | 2/2 | IN[A] | 2 mg[C] | 2 mg (API) dose to right naris | Blood[B] |
| F-OLZ #5 | OLZ:HPMC:DSPC (30:62:8 w/w) | 2/2 | IN[A] | 2 mg[C] | 2 mg (API) dose to right naris | Blood[B] |

TABLE 7 [D]-continued

| Group | Test Article | Number of Animals (Male/Female) | Dose Route | Dose Level | Administration | Collection Medium and Intervals |
|---|---|---|---|---|---|---|
| F-OLZ #6 | OLZ:HPMC:DSPC: Maltoside (50:41:8:1 w/w) | 2/2 | IN[A] | 2 mg[C] | 2 mg (API) dose to right naris | Blood[B] |

Figure 2:
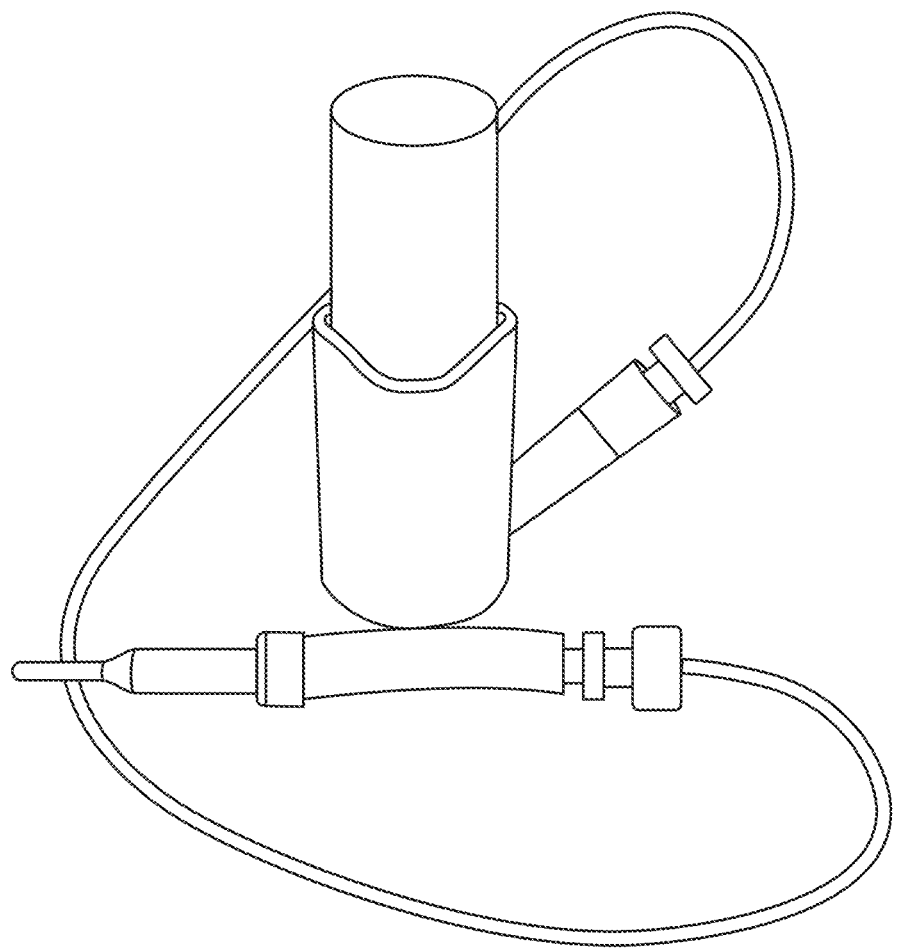
FIG. 2 shows an image of the NHP-POD device used for administration of olanzapine to NHPs as described in Examples 1 and 2.

[A]Intranasal (IN) administration of the formulations was administered using the powder nhpPOD Device shown in FIG. 2, to awake NHPs.
[B]Blood samples were collected at pre-dose (0), 0.05, 0.117, 0.25, 0.5, 0.75, 1, 1.5, 2, 4, 6, 10, 18, 24 hours post dose into K₂EDTA tubes with OLZ stabilizer.
[C]2 mg of olanzapine API was dosed through one spray to a single naris.
[D] The six lead compounds (F-OLZ #1-6) were tested in multiple PK studies using the identical study design provided in Table 7.

Blood Sample Preparation and LC/MS/MS Analysis

Blood samples were collected and centrifuged to isolate plasma. The plasma was analyzed by chromatography-mass spectrometry-mass spectrometry (LC/MS/MS) method optimized to measure olanzapine.

Raw data from the mass spectrometer was acquired and processed by non-compartmental analysis using Phoenix WinNonlin (v6.3 and v 8.0). Tolerability and pharmacodynamic impacts of each nasal OLZ formulation were also observed and recorded throughout the study.

5.7.2.3. Results

Short-term (1 week) stability of the formulations was assessed under accelerated conditions (40° C./75% relative humidity). Chemical stability, physical stability (data not shown), and device compatibility tests were used to select formulations for in vivo studies and to identify potential degradants. Short-term formulation stability results for the six lead formulations are shown in Table 8.

TABLE 8

Stability under Accelerated (40° C./75% relative humidity) Storage Conditions

| Group | Test Article | Manufacturing process | Purity % T = 0 | Purity % T = 1 week | NHP-POD Device Compatibility (% Variability, N = 5) |
|---|---|---|---|---|---|
| F-OLZ #1 | Cipla API | NA[1] | 99.8 | 99.8 | ±21% |
| F-OLZ #2 | OLZ:HPMC:DSPC (50:42:8 w/w) | B | 99.8 | 100 | ±6% |
| F-OLZ #3 | OLZ:HPMC:PLURONIC F68 (50:19:31 w/w) | A | 100.5 | 112 | ±6% |
| F-OLZ #4 | OLZ:HPMC:DSPC:Citric Acid (41:34.5:6.5:18 w/w) | C | 94.9 | 91.6 | ±10% |
| F-OLZ #5 | OLZ:HPMC:DSPC (30:62:8 w/w) | A | 96.1 | 98.7 | ±10% |
| F-OLZ #6 | OLZ:HPMC:DSPC:Maltoside (50:41:8:1 w/w) | A | ND[2] | ND[2] | ±30% |

[A]Not available.
[1]Not determined.

The short-term stability results demonstrate that the six lead formulations have good purity over the brief accelerated period. Powder flow characteristics of the formulations impacted device compatibility as shown by differences in variability.

One of the six lead formulations, F-OLZ #2, was tested on stability for 5 months and had >99% assay and <1% total impurities over the long-term storage period. Furthermore, device uniformity (compatibility of the device delivering the formulation) results for F-OLZ #2 over the 5-month period were excellent, demonstrating that even with minor changes to powder characteristics (e.g., moisture content), the formulation continues to perform well with POD technology (Table 9). These results demonstrate that good shelf-life for POD-OLZ is feasible, especially considering that the stability study was conducted without the opportunity to optimize packaging during this early stage.

TABLE 9

Stability of F-OLZ #2 at Room Temperature Storage Conditions (25° C./60% RH)

| | T = 0 | T = 1 month | T = 2 months | T = 3 months | T = 5 months |
|---|---|---|---|---|---|
| Purity % | 96.5 | 99.0 | 99.7 | 99.1 | 99.3 |
| Related Substances (Total %) | 0.3 | 0.2 | 0.4 | 0.6 | 0.9 |
| Device Uniformity | 10.6 mg ± 6% | 9.7 mg ± 6% | 9.9 mg ± 4% | 9.9 mg ± 5% | 10.1 mg ± 6% |

TABLE 9-continued

Stability of F-OLZ #2 at Room Temperature Storage Conditions (25° C./60% RH)

| | T = 0 | T = 1 month | T = 2 months | T = 3 months | T = 5 months |
|---|---|---|---|---|---|
| Moisture Content % | 0.8 | 1.6 | 2.2 | 2.2 | 2.1 |

Figure 3:
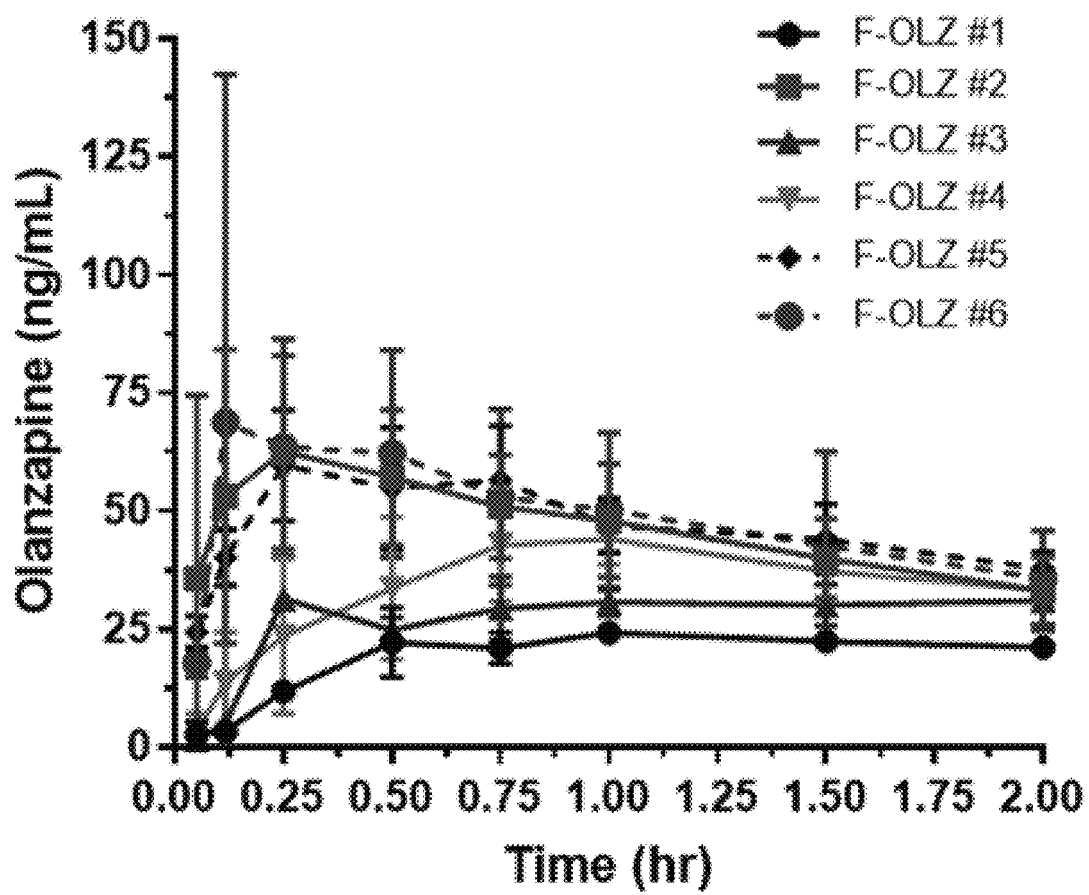
FIG. 3 shows time-course changes in plasma concentrations of olanzapine following administration of nasal powder formulations of olanzapine (F-OLZ #1-6) delivered to non-human primates (NHPs) by the NHP-POD device (time displayed 0-2 hours).
Figure 4:
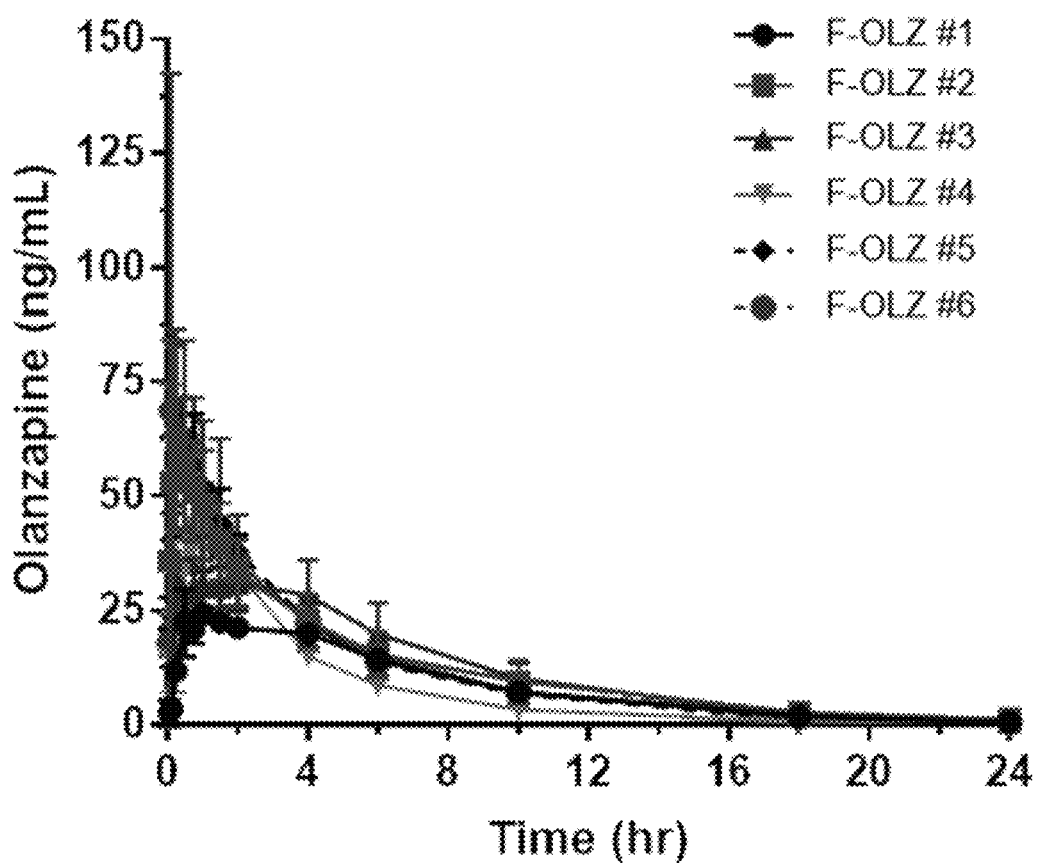
FIG. 4 shows time-course changes in plasma concentrations of olanzapine following administration of nasal powder formulations of olanzapine (F-OLZ #1-6) delivered to NHPs by the NHP-POD device (time displayed 0-24 hours).

PK study results of the six lead formulations (F-OLZ #1-6) in NHPs are provided in FIGS. 3 and 4. Specifically, FIGS. 3 and 4 provide plasma concentration time curves from blood samples collected following administration of one of the six different olanzapine (OLZ) formulations. Various PK parameters following the olanzapine administration by the NHP-POD device are also summarized in Table 10.

zapine, though the time to onset was delayed and effect was less pronounced in groups with slower time to peak plasma concentration and with lower peak exposure.

This series of pre-clinical studies demonstrated that tested lead olanzapine formulations have chemical stability, excellent purity, and device compatibility over at least 5 months, suggesting a reasonable shelf-life will be feasible for a

TABLE 10

Pharmacokinetic Parameters Following POD-OLZ Administration to NHP

| Group | Test Article | Median $T_{max}$ (min) [min, max] | Mean $C_{max}$ (ng/mL) (±SD) | Mean $AUC_{0-24\ hr}$ (ng * hr/mL) (±SD) | Mean $t_{1/2}$ (hr) (±SD) |
|---|---|---|---|---|---|
| F-OLZ #1 | Cipla API | 60 [30, 60] | 26 ± 4.4 | 201 ± 21 | 4.7 ± 0.6 |
| F-OLZ #2 | OLZ:HPMC:DSPC (50:42:8 w/w) | 15 [3, 30] | 71 ± 30 | 297 ± 62 | 4.5 ± 0.9 |
| F-OLZ #3 | OLZ:HPMC:PLURONIC F68 (50:19:31 w/w) | 30 [15, 120] | 35 ± 4.9 | 279 ± 65 | 4.3 ± 0.4 |
| F-OLZ #4 | OLZ:HPMC:DSPC:Citric Acid (41:34.5:6.5:18 w/w) | 54 [30, 60] | 47 ± 6.2 | 184 ± 13 | 3.7 ± 0.3 |
| F-OLZ #5 | OLZ:HPMC:DSPC (30:62:8 w/w) | 15 [15, 30] | 60 ± 12 | 285 ± 34 | 3.7 ± 0.3 |
| F-OLZ #6 | OLZ:HPMC:DSPC:Maltoside (50:41:8:1 w/w) | 23 [7.2, 30] | 89 ± 63 | 276 ± 75 | 3.9 ± 0.2 |

The results showed that administration of formulations F-OLZ #2, F-OLZ #5 and F-OLZ #6 to NHPs via the NHP-POD device resulted in rapid uptake with short time to median $T_{max}$ (15, 15 and 23 min, respectively) and less than 7 min to exceed 40 ng/mL, which is approximately the plasma concentration achieved in stable non-agitated patients following 3×10 mg intramuscular injections (Zyprexa NDA 21253). Delivery of formulations F-OLZ #1, F-OLZ #3 and F-OLZ #4 to NHPs via the NHP-POD device resulted in slower plasma uptake compared to the other 3 formulations, but still resulted in $T_{max}$ of 30-60 min, which is significantly faster than time to peak plasma concentration previously reported for oral olanzapine (OLZ) tablets or disintegrating tablets ($T_{max}$~5-8 hrs).

All six formulations delivered by the NHP-POD device were well tolerated following single dose administration to NHPs. No visible irritation was observed following administration or 24 hours after delivery. Additionally, though not shown in this Example, 14-day sub-chronic toxicity in rat was studied with nasal olanzapine delivery. No macroscopic or microscopic findings were reported suggesting that acute and repeat exposure nasal olanzapine will be well tolerated in human patients.

The pharmacodynamic effects of each nasal olanzapine formulation administered to NHPs were collected throughout each study. For lead formulations with shorter time to $T_{max}$, visible calming, though not excessive sedation, was observed in the NHPs by the 7 min blood draw, and the effect continued through 24 hours. This reported calming effect was observed in all groups that received nasal olanpowder POD-OLZ product. Moreover, nasal delivery of olanzapine by the POD device resulted in rapid uptake across the nasal epithelium in NHP, with lead formulations resulting ~15 min time to maximum plasma concentration, comparable to the intramuscular injection of olanzapine. Olanzapine nasal formulations delivered by NHP-POD device were well tolerated and exhibited rapid calming effects, both positive attributes of a potential treatment for acute agitation.

The results have led to the identification of a lead formulation.

5.7.3. Example 3: A Phase 1 Clinical Trial of INP105 (Olanzapine Delivered Intranasally by I231 POD® Device) in Healthy Human Volunteers 5.7.3.1. Study Formulation Based on the results described in Example 2 above, the F-OLZ #2 formulation was chosen for the first human clinical trial. The dry powder formulation contains olanzapine, HPMC and DSPC in the weight ratios of OLZ:HPMC:DSPC (50:42:8 w/w). Further characteristics of the cGMP batch are provided in Table B below. Stability data for the encapsulated cGMP drug product is provided in Table C below.

TABLE B

| Code | Formulation Description | Manufacturing process | Assay % | XRPD (no unit) | Tg (° C.) | Water content (% w/w) |
|---|---|---|---|---|---|---|
| cGMP | OLZ:HPMC:DSPC (50:42:8 w/w) | Hot process, 90:10 (1- | 98.4 | Amorphous (absence of | 67.24 | 0.89 |

TABLE B-continued

| Code | Formulation Description | Manufacturing process | Assay % | XRPD (no unit) | Tg (° C.) | Water content (% w/w) |
|---|---|---|---|---|---|---|
| | | propanol:wather). Required secondary drying | | crystallinity peaks) | | |

TABLE C

| | Limit/ Specification | T = 0 * | T = 1 mon * | T = 3 mon |
|---|---|---|---|---|
| *25° C./60% RH* | | | | |
| Dose Reproducibility (8.5-11.5 mg, N = 20) | 10 mg ± 15% (8.5-11.5 mg) | 10.7 mg Pass | 10.6 mg Pass | 11.3 Pass |
| Assay % (Impurities %) | 80-120% (Report result) | 101.9 (<0.1) | 100.2 (<0.1) | 100.6 (0.41) |
| Water Content (%) by KF | Report result | 1.23 | 1.04 | 1.4 |
| Microbiological testing | TAMC <100 cfu/g TYMC <10 cfu/g Ps. Aeruginosa- absent Staph. Aureus- absent | <100 cfu/g <10 cfu/g absent absent | NA | NA |
| *30° C./65% RH* | | | | |
| Dose Reproducibility (8.5-11.5 mg, N = 20) | 10 mg ± 15% (8.5-11.5 mg) | 10.7 mg Pass | 10.6 mg Pass | 10.9 mg Pass |
| Assay % (Impurities %) | 80-120% (Report result) | 101.9 (<0.1) | 100.3 (0.36) | 98.3 (2.15) |
| Water Content (%) by KF | Report result | 1.23 | 1.02 | 2.3 |
| Microbiological testing | TAMC <100 cfu/g TYMC <10 cfu/g Ps. Aeruginosa- absent Staph. Aureus- absent | <100 cfu/g <10 cfu/g absent absent | NA | NA |

5.7.3.2. Study Design

The powder formulation of olanzapine was tested in a randomized, double-blind, placebo-controlled and active-controlled, ascending-dose, 2-way, 2-period, incomplete block, crossover, Phase 1 trial to compare the safety, tolerability, PK and PD of three single doses of INP105 (olanzapine delivered by I231 POD® Device) with the safety, tolerability, PK and PD of one dose of intramuscular olanzapine (Zyprexa IM, 5 mg) and one dose of olanzapine administered orally using an orally disintegrating tablet (ODT) (Zyprexa Zydis, 10 mg). Randomization for Periods 1 and 2 was performed for each subject on Day 1. The I231 POD® device is a handheld, manually actuated, propellant-driven, metered-dose administration device designed to deliver a powder drug formulation of olanzapine to the nasal cavity.

Period 1: In Period 1, subjects were assigned to 1 of 3 cohorts (n=12 per cohort). Within each cohort, subjects were randomized 6:6 to one of two reference therapy treatment groups receiving a single dose of Zyprexa IM or Zyprexa Zydis, as outlined in Table 11. Dose administration occurred at Visit 2 on Day 1 (relative to each cohort). Each cohort was scheduled to allow time for Period 2 safety assessments to occur prior to dose escalation in the next cohort period 2 dosing. Subjects remained confined to the study site for 72 hours after dosing. Subjects returned to the study site on Days 5 and 6 (Visits 3 and 4) for follow-up assessments.

Period 2: In Period 2, subjects returned to the study site after a washout period of at least 14 days. Subjects from each Period 1 cohort received a single dose of INP105 (5, 10 or 15 mg) or placebo in a 9:3 ratio, as outlined in Table 11. Dose administration occurred on Day 15. (Dosing was permitted to occur later than the calendar Day 15 as required for scheduling (up to 2 days) but not before Day 15.) Ascending-dose levels of INP105 (5, 10 or 15 mg) were administered to ascending cohort numbers as follows:

TABLE 11

Period 1 (n = 38) assignment to 1 of 2 reference therapy treatment group over 3 cohorts Period 2 (n = 38) assignment to 1 of 3 treatment group over 3 cohorts

| Cohort | Period 1 Allocation | Period 2 Allocation |
|---|---|---|
| Cohort 1 (n = 12) | Zyprexa IM 5 mg (n = 6) Zyprexa IM 10 mg (n = 2)[A] Zyprexa Zydis 5 mg (n = 6) | INP105 (5 mg OLZ as 1 actuation) (n = 10) Placebo (I231 POD ® Device as 1 actuation) (n = 4) |
| Cohort 2 (n = 12) | Zyprexa IM 5 mg (n = 6) Zyprexa Zydis 10 mg (n = 6) | INP105 (10 mg OLZ as 2 actuations) (n = 9) Placebo ((I231 POD ® Device as 2 actuations) (n = 3) |
| Cohort 3 (n = 12) | Zyprexa IM 5 mg (n = 6) Zyprexa Zydis 10 mg (n = 6) | INP105 (15 mg OLZ as 3 actuations) (n = 9) Placebo (I231 POD ® Device as 3 actuations) (n = 3) |

[A]Post-Amendment Note: In cohort 1, 2 subjects already received Zyprexa 10 mg IM in the first dosing period based on the original (v1.0) version of the protocol. Subjects originally assigned to this Period 1 dosing arm continue with dosing as already allocated for Period 2.

Dose escalation between cohorts in Period 2 was performed in sequence. After 48 hours of inpatient confinement for the last available subject in each cohort, all available safety data from the preceding dose level of INP105 were reviewed before initiating dosing in the next higher dose cohort. Cohort 3, Period 2 was divided up into a "sentinel" group of 4 subjects with double blind dosing spaced at least 30 minutes apart. If no safety concerns were reported, the remaining 8 subjects were all dosed the next day.

Safety and tolerability: Safety was determined by evaluating physical examination findings, nasal examination findings, ECGs, vital signs, clinical laboratory parameters, concomitant medication usage and adverse events (AEs). If deemed necessary, additional safety measurements were performed at the discretion of the Investigator, SME or LMM.

Pharmacodynamics: The following tests were performed, in sequence, at the specified PD assessment time points:
 1. Subjective sedation by Visual Analogue Scale (VAS)
    Subjects were asked to assess their own level of sedation during the study with the descriptive anchor terms Alert/Drowsy, Foggy/Clear-headed and Energetic/Lethargic.

2. Agitation/Calmness Evaluation Scale (ACES)
   A single-item scale developed to assess the level of agitation-calmness where 1=marked agitation; 2=moderate agitation; 3=mild agitation; 4=normal; 5=mild calmness; 6=moderate calmness; 7=marked calmness; 8=deep sleep; and 9=unable to be aroused.
3. Attention by Digit Symbol Substitution Test (DSST).
   Requires response speed, sustained attention, visual spatial skills and set shifting. Subjects record the symbols that correspond to a series of digits as outlined on the test paper. Completion of the task is timed. Data are summarized by treatment. The relationship between PD variables and PK is analyzed on an exploratory basis.

Pharmacokinetics: Olanzapine (OLZ) concentration-time profiles for each administration method are presented graphically. Plasma OLZ PK parameters: mean time to maximum plasma drug concentration ($T_{max}$), maximum observed drug plasma concentration ($C_{max}$), area under the curve (AUC) from time zero to the time of the last measurable concentration ($AUC_{0-last}$), terminal elimination rate constant ($k_{el}$), AUC from time zero to infinity ($AUC_{0-inf}$), elimination half-life ($t_{1/2}$), total apparent body clearance (CL/F) and apparent volume of distribution at the terminal phase ($V_{z/F}$) (where data are sufficient for parameter determination) were calculated.

5.7.3.3. Results

Pharmacokinetic Assessments: Plasma concentration-time data for olanzapine were used to determine pharmacokinetic (PK) parameters. The following pharmacokinetic parameters were determined: $C_{max}$, $T_{max}$, $T_{last}$, $AUC_{last}$, and $t_{1/2}$ where possible. Results are displayed in Table 12 and FIGS. 8A-C.

istration of a formulation of olanzapine containing HPMC and DSPC increases the rate and extent of uptake and subsequent systemic exposure, as a slightly higher AUC and $C_{max}$ and a significantly shorter $T_{max}$ were demonstrated compared to the IM administered olanzapine (Zyprexa IM) or orally administered olanzapine (Zydis ODT).

Pharmacodynamic assessments: Measurement of a Visual Analogue Scale (VAS) score was conducted for each subject by asking the subject to assess his or her own level of sedation during the study with the descriptive anchor terms: Alert/Drowsy, Foggy/Clear-headed and Energetic/Lethargic. Average VAS scores with respect to the three categories for each subject group treated with the INP105, IM olanzapine (Zyprexa IM), oral olanzapine (Zydis ODT) or placebo are displayed in FIG. 9. The results show that administration of olanzapine provided dose-dependent behavioral effects in all subject groups treated with olanzapine regardless of the routes of administration.

Pharmacodynamic effects were further assessed by Agitation/Calmness Evaluation Scale (ACES). ACES is a single-item scale developed to assess the level of agitation-calmness where 1=marked agitation; 2=moderate agitation; 3=mild agitation; 4=normal; 5=mild calmness; 6=moderate calmness; 7=marked calmness; 8=deep sleep; and 9=unable to be aroused. Maximum ACES changes compared to the baseline are presented in FIG. 10 and ACES-time profiles for each administration method are presented in FIGS. 11A-B. The ACES data confirmed dose-dependent sedation effects in all subject groups treated with olanzapine regardless of the routes of administration. Intranasal olanzapine (INP105) induced similar sedation effects to IM olanzapine (Zyprexa IM) at the same dose. Furthermore, the ACES-time profiles presented in FIGS. 11A-B show that sedation effects of

TABLE 12

|  | $T_{max}$ (median, hr) | $C_{max}$ (mean, ng/mL) | $AUC_{0-last}$ (mean, ng * hr/mL) | $AUC_{0-inf}$ (mean, ng * hr/mL) | $t_{1/2}$ (mean, hr) |
| --- | --- | --- | --- | --- | --- |
| INP105 - 5 mg[A] (N = 9) | 0.17 | 31.5 | 285 | 349 | 41.2 |
| INP105 - 10 mg (N = 9) | 0.17 | 74.5 | 666 | 750 | 44.3 |
| INP105 - 15 mg (N = 8) | 0.16 | 88.8 | 724 | 815 | 38.5 |
| Zyprexa IM 5 mg[A] (N = 19) | 0.33 | 25.9 | 283 | 322 | 41.1 |
| Zyprexa IM 10 mg (N = 2) | 0.35 | 73.1 | 461 | 480 | 33.2 |
| Zydis ODT 10 mg (N = 18) | 2.0 | 17.5 | 502 | 566 | 37.1 |

[A]Excluding Subject 103-011 (Period 2) and 103-054 (Petiod 1) results. Data is under investigation.

Intranasal administration of olanzapine (INP105) using the I231 POD device provides dose-dependent $C_{max}$. All doses provide mean $C_{max}$>30 ng/ml with mean $T_{max}$<0.2 hour.

The PK results show that intranasal delivery using the nhpPOD Device of a formulation of olanzapine containing HPMC and DSPC results in similar or slightly higher plasma exposure (AUC) and maximum $C_{max}$ as compared to the IM administered olanzapine (Zyprexa) at the same dose. The earliest time point drug was measured was 5 minutes, and the median $T_{max}$ was approximately 0.16-0.17 hr after intranasal delivery of a formulation of olanzapine, significantly shorter than the median $T_{max}$ measured for the IM administered olanzapine (0.33-0.36 hr) or orally administered olanzapine (2 hr). The results suggest that intranasal adminolanzapine appear significantly earlier in the subject groups treated with intranasal olanzapine (INP105) or IM olanzapine (Zyprexa IM), compared to the subject group treated with oral olanzapine (Zyprexa Zydis). These results are consistent with the PK study results, where median $T_{max}$ for the intranasally administered olanzapine (0.16-0.17 hr) or the IM administered olanzapine (0.33-0.36 hr) was found to be significantly shorter than for orally administered olanzapine (2 hrs).

Additionally, attention by Digit Symbol Substitution Test (DSST) was conducted to assess response speed, sustained attention, visual spatial skills and set shifting in response to olanzapine administration. Each subject was instructed to record the symbols that correspond to a series of digits as outlined on the test paper. Completion of the task was timed and data are summarized and provided in FIGS. 12 and 13A-B. The maximum DSST changes compared to the baseline presented in FIG. 12 show that administration of olanzapine decreases response speed in a dose dependent manner regardless of the route of administration.

Maximum changes in DSST from baseline are presented in FIG. 12, and DSST-time profiles are presented in FIGS. 13A-B. The DSST-time profiles presented in FIGS. 13A-B show that behavioral effects of olanzapine start significantly earlier in the subject groups treated with intranasal olanzapine (INP105) or IM olanzapine (Zyprexa IM), compared to the subject group treated with oral olanzapine (Zyprexa Zydis). These results are consistent with the PK study results as well as PD study results based on ACES profiles, described above.

PK/PD plots: Olanzapine concentration-time profiles and DSST or ACES-time profiles for each subject group are superimposed and presented in FIGS. 14A-F and 15A-F (DSST) and FIGS. 16A-F and 17A-F (ACES). The graphs show that intranasal administration (INP105) or IM administration of olanzapine (Zyprexa IM) induced rapid increase of olanzapine concentration and rapid behavioral changes as measured by DSST or ACES. On the other hand oral administration of olanzapine (Zyprexa Zydis) induced significantly slower responses, both in the olanzapine concentrations and in the DSST or ACES responses.

Conclusions: The data show that olanzapine delivered by intranasal administration has dose-dependent pharmacokinetics and provides a mean peak plasma olanzapine concentration ($C_{max}$) of at least 30 ng/mL, with a mean time to $C_{max}$ ($T_{max}$) of less than 15 minutes, approaching a $T_{max}$ of 10 minutes. Furthermore, olanzapine administered by the POD device provide a large AUC, a short mean time to $C_{max}$ ($T_{max}$) and rapid behavioral effects, similar to or better than IM olanzapine (Zyprexa) at the same dose, suggesting effective absorption of olanzapine across the nasal epithelium. This shows that intranasal delivery of olanzapine can be an effective method for acute treatment of agitation.

6. INCORPORATION BY REFERENCE

The disclosures of each and every patent, patent application, and publication cited herein are hereby incorporated by reference in their entirety.

7. EQUIVALENTS

While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A method for acutely treating agitation in a human subject, comprising:
   intranasally administering, using an intranasal delivery device, a single dose of a dry pharmaceutical composition comprising 2-20 mg of olanzapine as a single active ingredient to the subject exhibiting agitation, thereby reducing agitation within 30 minutes,
   wherein the intranasal delivery device comprises a compound chamber containing the dry pharmaceutical composition and a separate propellant canister containing propellant;
   wherein the propellant released from the canister contacts and propels dry pharmaceutical composition through a narrow, targeted delivery plume for intranasal delivery;
   wherein the intranasal administration provides a shorter median $T_{max}$ compared to intramuscular or oral administration of the single dose of olanzapine, and
   wherein the intranasal administration provides a mean peak plasma olanzapine concentration ($C_{max}$) of at least 25 ng/ml.

2. The method of claim 1, wherein the dry pharmaceutical composition is a powder.

3. The method of claim 2, wherein the powder comprises olanzapine particles (i) in a crystalline form, (ii) in an amorphous form, optionally wherein the amorphous form is obtained by spray-drying, or (iii) in a partially crystalline and partially amorphous form.

4. The method of claim 3, wherein the median diameter of the olanzapine particle size distribution (D50) in the powder is between 1 μm and 50 μm.

5. The method of claim 1, wherein the dry pharmaceutical composition comprises no more than 70 wt % olanzapine.

6. The method of claim 1, wherein the dry pharmaceutical composition comprises less than 3 wt % water.

7. The method of claim 1, wherein the dry pharmaceutical composition consists essentially of:
   50 wt % olanzapine;
   42 wt % hydroxypropylmethylcellulose (HPMC); and
   8 wt % 1,2-distearoyl-sn-glycero-3-phosphocholine (DSPC).

8. The method of claim 1, wherein the intranasal delivery device is (i) a handheld, manually actuated, metered-dose intranasal administration device or (ii) a handheld, manually actuated, propellant-driven, metered-dose intranasal administration device.

9. The method of claim 1, wherein the dry pharmaceutical composition is, prior to device actuation, (i) encapsulated within a capsule positioned within the device or (ii) stored within a dose container that is removably coupled to the device.

10. The method of claim 1, wherein the single dose of dry pharmaceutical composition comprises 5-15 mg of olanzapine.

11. The method of claim 1, wherein the single dose of dry pharmaceutical composition comprises 5 mg of olanzapine.

12. The method of claim 1, wherein the single dose of dry pharmaceutical composition comprises 10 mg of olanzapine.

13. The method of claim 1, wherein the single dose of dry pharmaceutical composition comprises 15 mg of olanzapine.

14. The method of claim 1, wherein the subject has schizophrenia, bipolar disorder, autism, dementia, post traumatic stress disorder (PTSD), intoxication, or a drug-induced psychotic state.

15. The method of claim 1, wherein the intranasal administration provides a mean peak plasma olanzapine concentration ($C_{max}$) of at least 30 ng/mL.

16. A kit for acutely treating agitation in a human subject, comprising:
   a dry pharmaceutical composition in a unit dosage form suitable for intranasal administration using an intranasal delivery device, thereby reducing agitation within 30 minutes, wherein the dry pharmaceutical composition comprises:
   2-20 mg of olanzapine as a single dose of a single active ingredient, and at least one excipient and, the intranasal delivery device comprising a compound chamber containing the dry pharmaceutical composition, and a propellant canister containing the propellant, wherein the propellant released from the propellant canister propels the dry pharmaceutical composition through a narrow, targeted delivery plume for intranasal delivery, thereby providing (1) a median $T_{max}$ which is shorter compared to intramuscular or oral administration of the unit dose of olanzapine, and (2) a mean peak plasma olanzapine concentration ($C_{max}$) of at least 25 ng/ml.

17. The kit of claim 16, wherein the dry pharmaceutical composition is a powder.

18. The kit of claim 16, wherein the dry pharmaceutical composition comprises olanzapine particles (i) in a crystalline form, (ii) in an amorphous form, optionally wherein the amorphous olanzapine is obtained by spray-drying or (iii) in a partially crystalline and partially amorphous form.

19. The kit of claim 18, wherein the median diameter of the olanzapine particle size distribution (D50) in the powder is between 1 μm and 50 μm.

20. The kit of claim 16, wherein the dry pharmaceutical composition comprises no more than 70 wt % olanzapine.

21. The kit of claim 16, wherein the dry pharmaceutical composition further comprises a stabilizer, wherein the stabilizer is selected from the group consisting of: HPMC, polyvinyl caprolactam-polyvinyl acetate-polyethylene glycol graft co-polymer (Soluplus), vinyl pyrrolinone-vinyl acetate copolymer (Kollidon VA64), polyvinyl pyrrolinone K30 (Kollidon K30), polyvinyl pyrrolidine K90 (Kollidon K90), hydroxypropylcellulose (HPC), hydroxypropyl beta-cyclodextrin (HPBCD), mannitol, and lactose monohydrate.

22. The kit of claim 16, wherein the dry pharmaceutical composition further comprises a permeation enhancer, wherein the permeation enhancer is selected from the group consisting of n-tridecyl-B-D-maltoside, n-dodecyl-β-D-maltoside, 1,2-distearoyl-sn-glycero-3-phosphocholine DS-PC, 1,2-dipalmitoyl-sn-glycero-3-phosphocholine (DPPC), 1,2-dioleoyl-sn-glycero-3-phosphocholine (DOPC), propylene glycol, disodium EDTA, PEG400 monostearate, polysorbate 80, and macrogol (15)-hydroxystearate.

23. The kit of claim 16, wherein the dry pharmaceutical composition further comprises an antioxidant, wherein the antioxidant is selected from the group consisting of alpha tocopherol, ascorbic acid, ascorbyl palmitate, bronopol butylated hydroxyanisole (BHA), butylated hydroxytoluene (BHT), citric acid monohydrate, sodium ascorbate, ethylene diainetetraacetic acid, fumaric acid, malic acid, methionine, propionic acid, sodium metabisulfite, sodium sulfite, sodium thiosulfate, thymol, and vitamin E polyethylene glycol succinate.

24. The kit of claim 16, wherein the dry pharmaceutical composition comprises less than 3 wt % water.

25. The kit of claim 16, wherein the dry pharmaceutical composition consists essentially of:
 50 wt % olanzapine;
 42 wt % hydroxypropylmethylcellulose (HPMC); and
 8 wt % 1,2-distearoyl-sn-glycero-3-phosphocholine (DSPC).

26. The kit of claim 16, wherein the dry pharmaceutical composition contains 5-15 mg of olanzapine.

27. The kit of claim 16, further comprising a capsule that encapsulates the dry pharmaceutical composition or a dose container that stores the dry pharmaceutical composition, wherein the dose container is configured to removably couple to the device.

28. The method of claim 15, wherein the intranasal administration provides a mean peak plasma olanzapine concentration ($C_{max}$) of at least 40 ng/mL.

29. The method of claim 15, wherein the intranasal administration provides a mean peak plasma olanzapine concentration ($C_{max}$) of at least 50 ng/mL.

30. The method of claim 15, wherein the intranasal administration provides a mean peak plasma olanzapine concentration ($C_{max}$) of at least 60 ng/mL.

31. The method of claim 15, wherein the intranasal administration provides a mean peak plasma olanzapine concentration ($C_{max}$) of at least 70 ng/mL.

32. The method of claim 15, wherein the intranasal administration provides a mean peak plasma olanzapine concentration ($C_{max}$) of at least 80 ng/mL.

33. The kit of claim 26, wherein the dry pharmaceutical composition contains 5 mg of olanzapine, 10 mg of olanzapine, or 15 mg of olanzapine.

* * * * *